(12) United States Patent
Lakowicz

(10) Patent No.: US 7,776,528 B2
(45) Date of Patent: Aug. 17, 2010

(54) RADIATIVE DECAY ENGINEERING

(75) Inventor: Joseph R. Lakowicz, Ellicot City, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 378 days.

(21) Appl. No.: 10/990,549

(22) Filed: Nov. 18, 2004

(65) Prior Publication Data

US 2005/0202464 A1  Sep. 15, 2005

Related U.S. Application Data

(62) Division of application No. 10/073,625, filed on Feb. 11, 2002.

(60) Provisional application No. 60/268,326, filed on Feb. 14, 2001.

(51) Int. Cl.
 *C12Q 1/68* (2006.01)
 *G01N 33/53* (2006.01)
 *G01N 21/76* (2006.01)
 *C07H 21/02* (2006.01)
 *C07H 21/04* (2006.01)
 *C07K 14/00* (2006.01)

(52) U.S. Cl. .......................... 435/6; 435/7.1; 436/172; 436/805; 536/23.1; 530/350

(58) Field of Classification Search ................ 436/525; 422/57, 82.11, 82.05, 82.06; 435/287.1; 385/12, 120, 131
See application file for complete search history.

(56) References Cited

U.S. PATENT DOCUMENTS

| 4,774,191 | A |   | 9/1988  | Khanna et al.          |
|-----------|---|---|---------|------------------------|
| 5,442,045 | A | * | 8/1995  | Haugland et al. ........ 530/391.3 |
| 5,827,653 | A |   | 10/1998 | Sammes                 |
| 5,837,552 | A |   | 11/1998 | Cotton et al.          |
| 5,864,397 | A | * | 1/1999  | Vo-Dinh ..................... 356/301 |
| 5,866,433 | A |   | 2/1999  | Schalkhammer et al.    |
| 5,952,236 | A |   | 9/1999  | Thompson               |
| 5,998,135 | A |   | 12/1999 | Rabbani                |
| 6,149,868 | A |   | 11/2000 | Natan                  |

(Continued)

FOREIGN PATENT DOCUMENTS

WO   WO 99/36779   7/1999

(Continued)

OTHER PUBLICATIONS

Vo-Dinh Sensors and Actuators, B 29, 1995 p. 183-189.*

(Continued)

*Primary Examiner*—Teresa E Strzelecka
(74) *Attorney, Agent, or Firm*—Gibb I.P. Law Firm, LLC

(57) ABSTRACT

Compositions and methods for increasing the fluorescence intensity of molecules are provided. In particular, compositions and methods directed to increasing the intrinsic fluorescence of biomolecules and low quantum yield fluorophores are described. The intrinsic fluorescence of biomolecules is increased by positioning a metal particle and a biomolecule at a distance apart sufficient to increase the radiative decay rate of the biomolecule. Methods for the identification of nucleic acids are also provided. The compositions and methods can also be used to increase the emission of any fluorophore, such as the extrinsic probes used to label biomolecules.

12 Claims, 38 Drawing Sheets

U.S. PATENT DOCUMENTS

| | | | |
|---|---|---|---|
| 6,235,535 | B1 | 5/2001 | Keinanen |
| 6,242,264 | B1 | 6/2001 | Natan et al. |
| RE37,412 | E | 10/2001 | Aussenegg et al. |
| 6,342,349 | B1 | 1/2002 | Virtanen |
| 6,417,340 | B1 | 7/2002 | Mirkin et al. |
| 6,485,962 | B1 * | 11/2002 | Tabacco et al. .......... 435/288.7 |
| 6,608,716 | B1 | 8/2003 | Armstrong et al. |
| 6,770,488 | B1 | 8/2004 | Carron et al. |
| 2002/0150938 | A1 * | 10/2002 | Kneipp et al. ................. 435/6 |
| 2002/0160400 | A1 | 10/2002 | Lakowicz |

FOREIGN PATENT DOCUMENTS

| | | |
|---|---|---|
| WO | WO 01/01142 | 1/2001 |
| WO | WO 01/09388 | 2/2001 |
| WO | WO 02/06835 | 1/2002 |

OTHER PUBLICATIONS

Lakowicz, J.R., "Principles of Fluorescence Spectroscopy", Second Edition, Kluwer Academic/Plenum Publishers, New York, pp. 63-65 (1999).*
Lakowicz, J.R. et al., J. Fluorescence, vol. 14(4), pp. 425-441 (2004).*
Vukovic, S. et al., J. Phys. Chem. C., vol. 113, pp. 121-133 (2009).*
Aroca, R. et al., Langmuir, vol. 4, pp. 518-521 (1988).*
Kobayashi, N. et al., Chem. Eur. J., vol. 9, pp. 5123-5134 (2003).*
Mazeres, S. et al., Biophys. J., vol. 71, pp. 327-335 (1996).*
Chen, R.F., "Phosphorescence of Tryptophan and Proteins in the Presence of Silver Ion", Arch. Biochem. Biophys., vol. 166, pp. 584-591 (1975).*
Benson et al, Nucleic Acids Research, 21(24):5720-5726 (1993).
Benson et al, Analytical Biochemistry, 231:247-255 (1995).
Denjin et al, APMIS, 100:669-681 (1992).
Ferea et al, Curr. Opin. Genet. Dev., 9:715-722 (1999).
Kneipp et al, Curr. Science, 77:915-924 (1999).
Prober et al, Science, 238:336-343 (1987).
Smith et al, Nature, 321:674-679 (1986).
Li et al, Bioconjugate Chem., 10:241-245 (1999).
Lipshutz et al, Nat. Genet. Suppl., 21:20-24 (1999).
Michaels et al, J. Am. Chem. Soc., 121:9932-9939 (1999).
Morgan et al, Photochem. Photobiol., 31:101-113 (1980).
Nie et al, Science, 275:1102-1106 (1997).
Vigny et al, Photochem. Photobiol., 20:345-349 (1974).
Wiegant et al, Genome Res., 10:861-865 (2000).
Lala et al, Phys. Chemistry Chem. Physics, 2(10):2461-2466 (2000).
Thiel et al, Analytical Chem., American Chem. Soc., 69(24):4948-4956 (1997).
Goodman et al, "A Review of the Colloidal Gold Maker System", Scanning Electron Microscopy, pp. 133-146 (Jan. 1980).
Lakowicz, Analytical Biochem., 298(1):1-24 (2001).
Stich et al, J. Nanoscience and Nanotechnology, 1(1):397-405 (2001).
Ford et al, Physics Report, 113(4):195-287 (1984).
Ju et al, Nature Medicine, vol. 2(2):246-249 (1996).
Morrison et al, Biochemistry, 32:3095-3104 (1993).
Chance et al, Adv. Chem. Phys., 31:1-65 (1978).
Schalkhammer et al, SPIE, 2976:129-136 (1997).
Knemeyer et al, Analytical Chemistry, 72(16):3717-3724 (2000).
Orden et al, Amer. Chem. Soc., 70(7):1444-1451 (1998).
Selvan et al, J. Phys. Chem. B., 103:7064-7067 (1999).
Barnes et al, J. of Modern Optics, 45(4):661-699 (1998).
Plessow et al, J. Phys. Chem., 104:3695 (2000).
Kümmerlen et al, Mol. Physics, 80(5):1031-1046 (1993).
Wokaun et al, J. Chem. Phys., 79(1):509-514 (1983).
Hua et al, J. Chem. Phys., 83(7):3650-3658 (1985).
Ballini et al, Biophys. Chem., 18:61-65 (1983).
Georghiou et al, Photochem. and Photobiol., 41(2):209-212 (1985).
Georghiou et al, Biophys. Journal., 70:1909-1922 (1996).
Gersten et al, J. Chem. Physcis, 75(3):1139-1152 (1981).
Gersten et al, Chem. Physics Letters, 104(1):31-37 (1984).
Gersten et al, Surface Science, 158:165-189 (1985).
Singer et al, J. Opt. Soc. Am. B., vol. 12, No. 2 (1995).
Turro et al, J. Am. Chem. Soc., 117:9026-9032 (1995).
Kerker et al, J. of Colloid and Interface Science, vol. 105, No. 2 (1985).
Lakowicz et al, Biochem. and Biophys. Res. Comm., vol. 286: 875-879 (2001).
Glass et al, Optics Letters, 5(9):368-370 (1980).
Graham et al, Bioplolymers (Biospectroscopy), 57:8531 (2000).
Leitner et al, Applied Physics B., 36:105-109 (1985).
Rivas et al, Amer. Chem. Soc., 17:574-577 (2001).
Aussenegg et al, Surface Science, 189/190:935-945 (1987).
Benner et al, Optics Communications, vol. 30, No. 2 (1979).
Sokolov et al, Anal. Chem., 70(18):3898-3905 (1998).

* cited by examiner

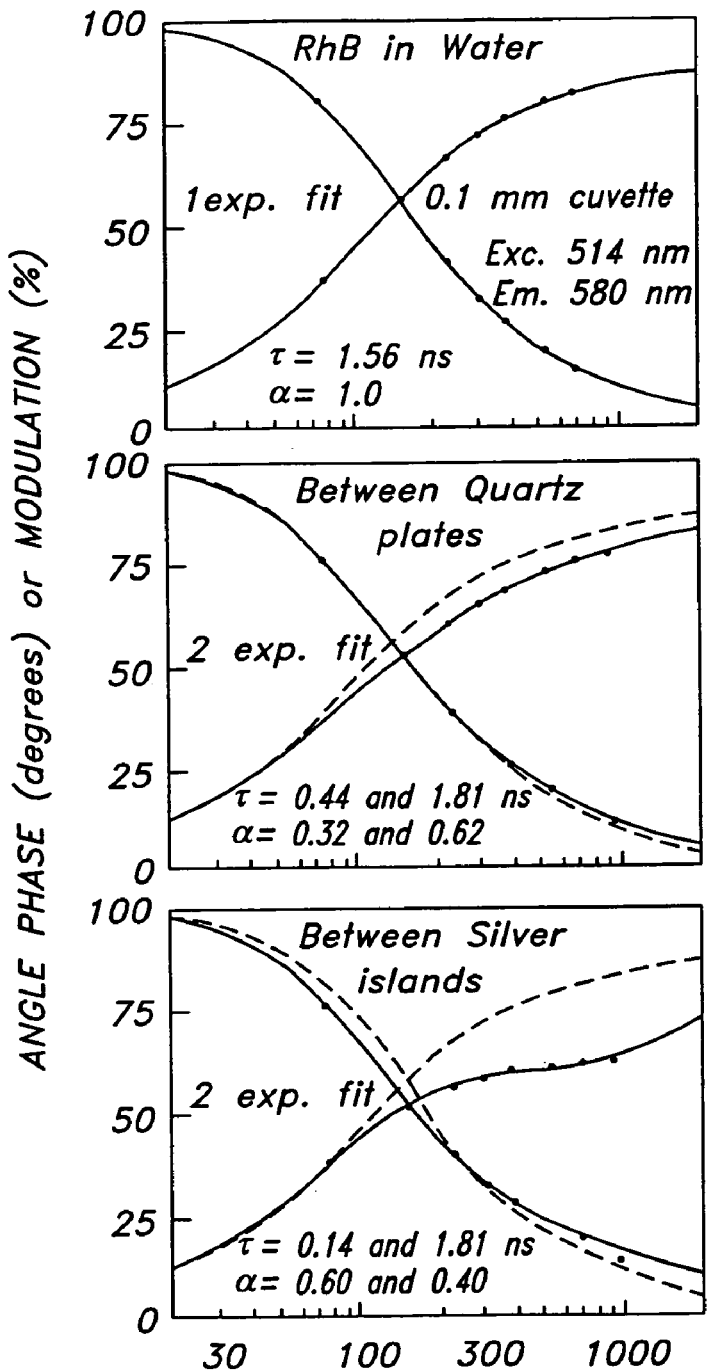

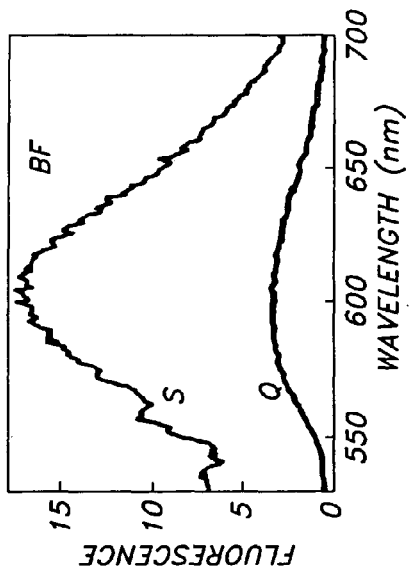
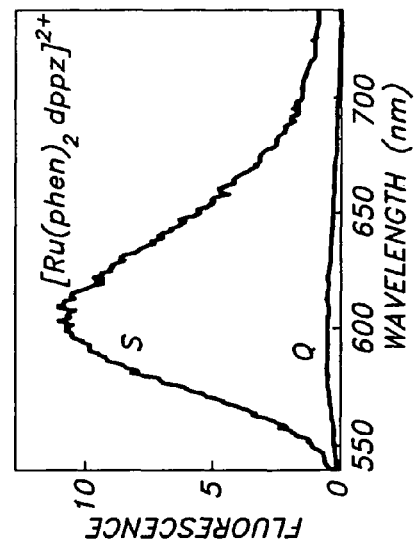
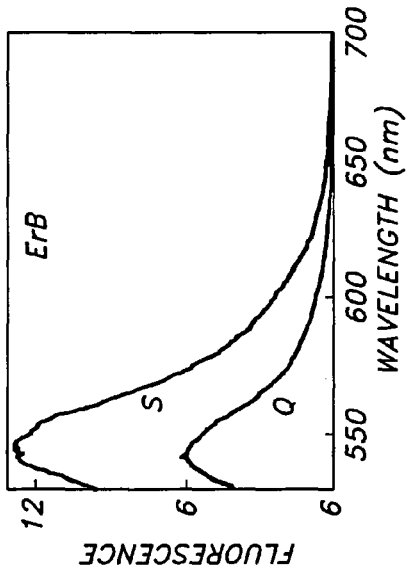
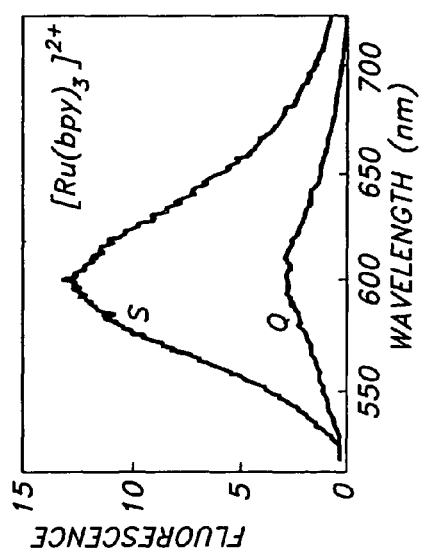

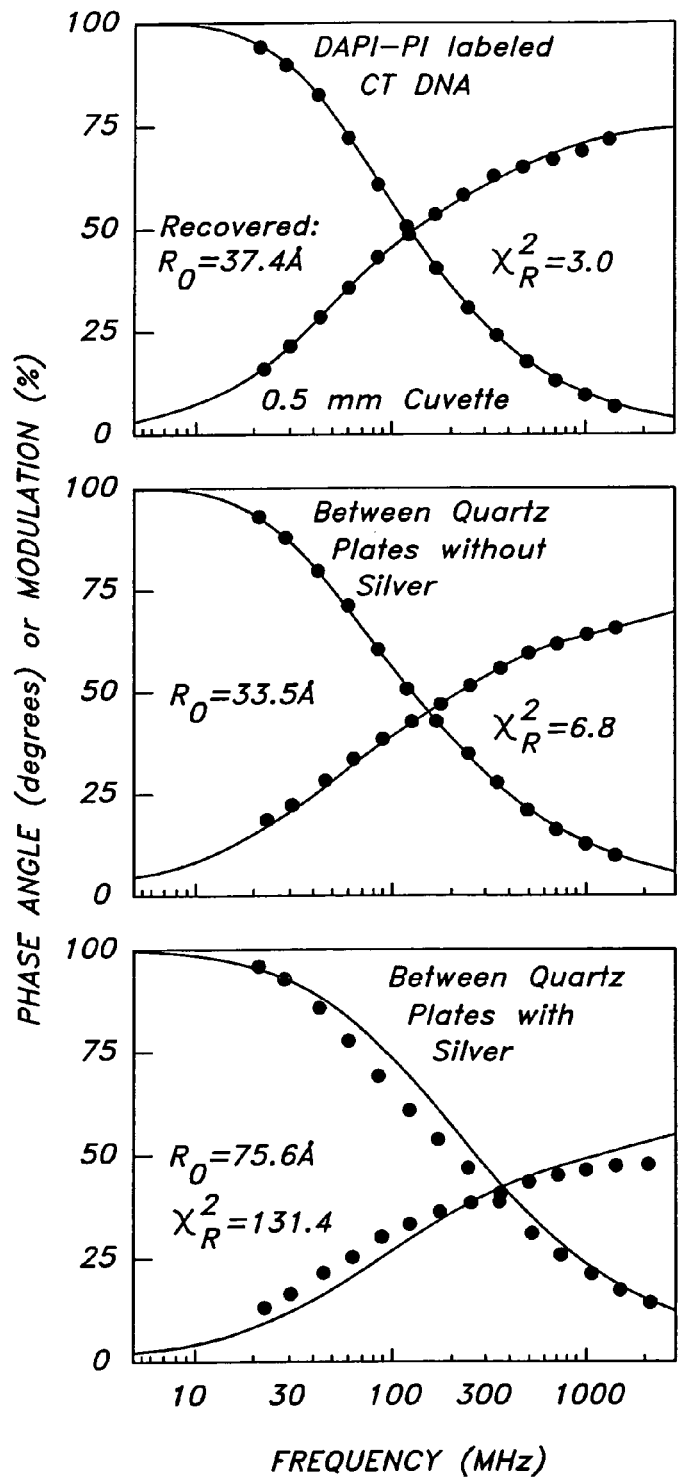

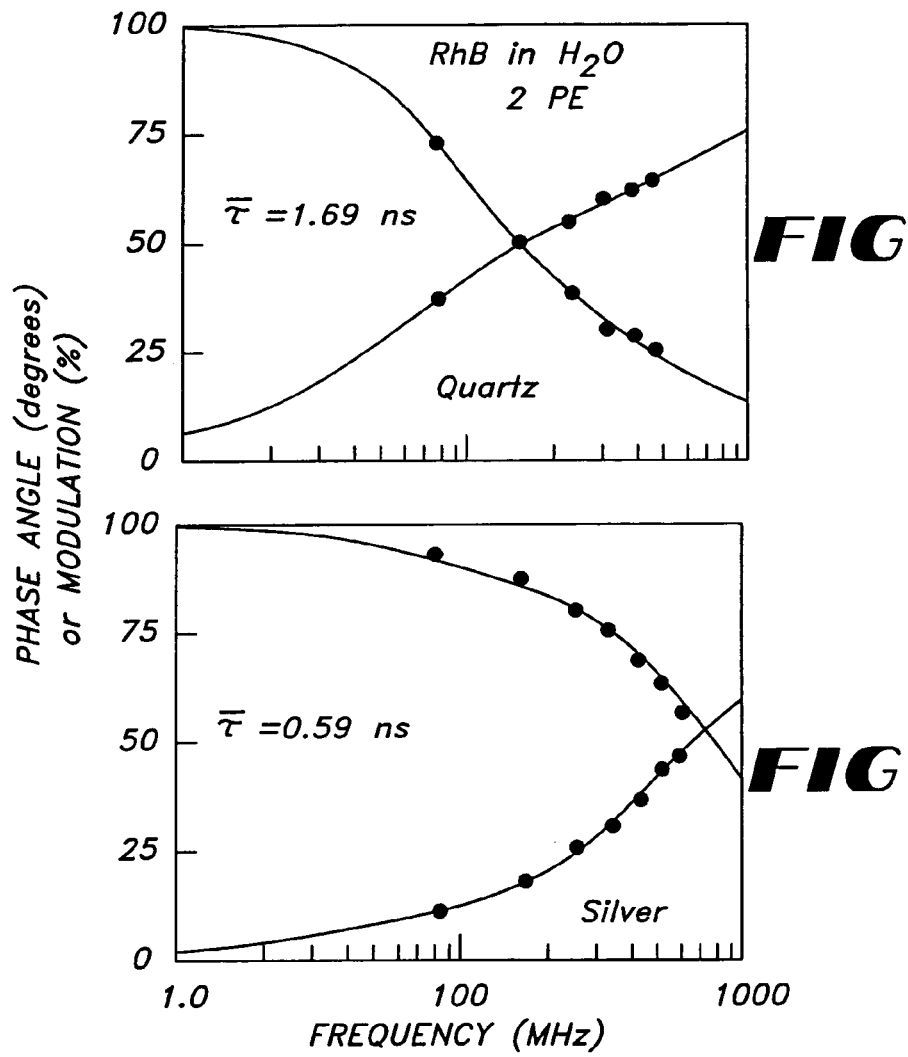

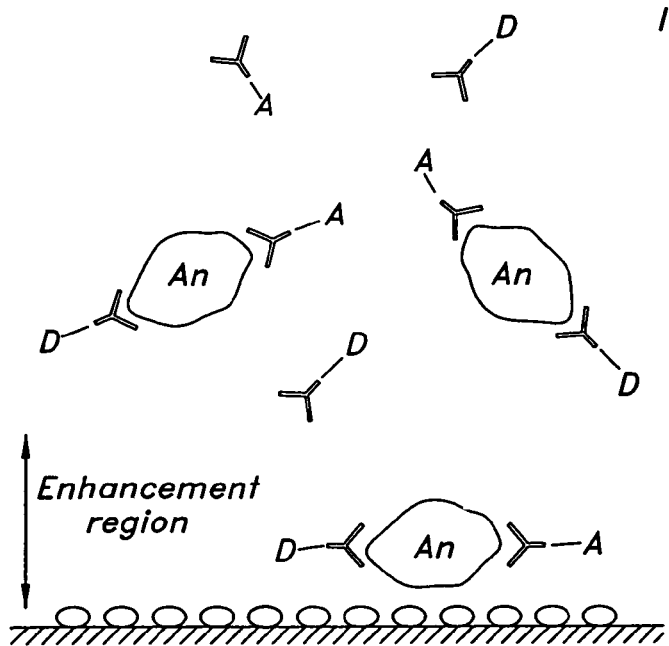
FIG 37A
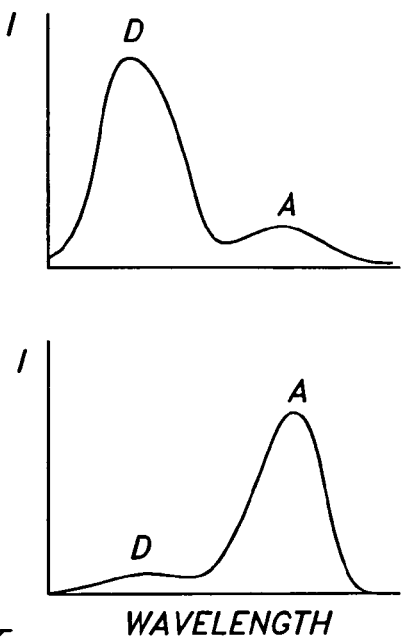
FIG 37B
FIG 37C

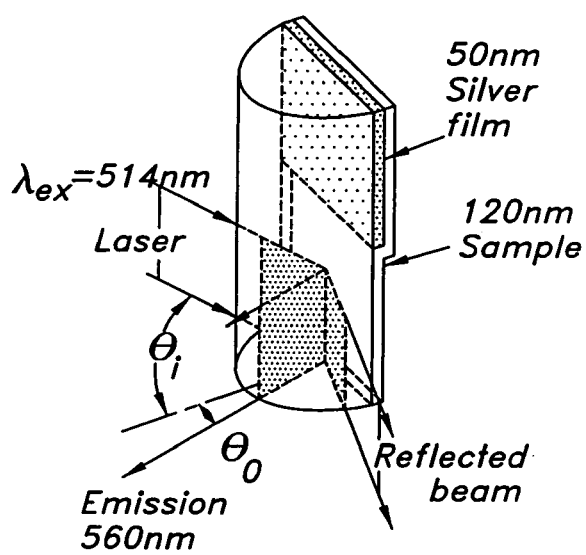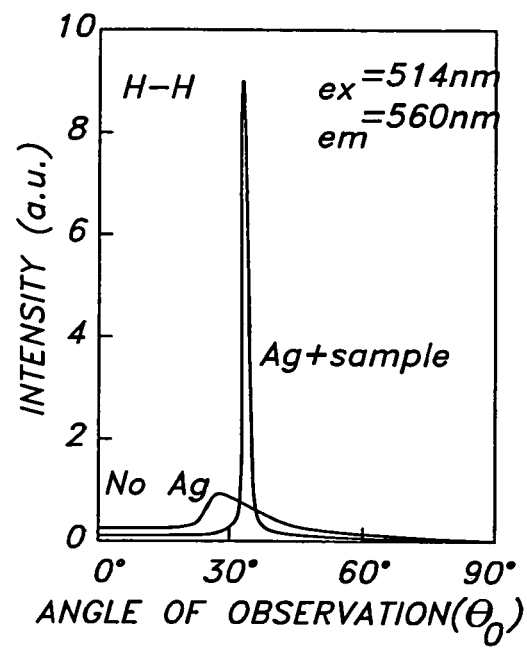
FIG 38A  FIG 38B

RADIATIVE DECAY ENGINEERING

CROSS REFERENCE TO RELATED APPLICATIONS

This application is a Divisional of U.S. application Ser. No. 10/073,625, filed Feb. 11, 2002; which claims benefit of priority under 35 U.S.C. §119(e) to U.S. provisional application No. 60/268,326 entitled "RADIATIVE DECAY ENGINEERING" filed on Feb. 14, 2001, the disclosure of each of which is hereby incorporated by reference in their entireties.

STATEMENT REGARDING FEDERALLY SPONSORED RESEARCH

The work leading to this invention was supported in part by the U.S. Government under grant number RR-08119 awarded by the NIH National Center for Research Resources; Therefore, the U.S. Government may have certain rights in this invention.

BACKGROUND OF THE INVENTION

1. Field of the Invention

The present invention is directed to compositions and methods for increasing, and detecting the fluorescence of a molecule, in particular, compositions and methods for increasing the intrinsic fluorescence of a biomolecule. This invention also is directed to methods and compositions for the detection of biomolecules by increasing and detecting the fluorescence of biomolecules.

2. Description of Related Art

The use of fluorescence technology has greatly enhanced the ability to detect specific molecules leading to rapid advancements in diagnostics. For example, fluorescence detection is widely used in medical testing and DNA analysis because of the high degree of sensitivity obtained using fluorescent techniques. Small numbers of molecules can be detected using fluorescence technology. Typically, extrinsic fluorophores are added covalently or non-covalently to allow molecules that do not ordinarily fluoresce or do not fluoresce at previously commercially useful levels to be detected. Biomolecules such as DNA ordinarily do not fluoresce at detectable levels, and extrinsic fluorophores are added to DNA to facilitate the detection of DNA on gels (Benson et al. (1993) *Nucleic Acids Res.* 21, 5720-5726; Benson et al. (1995) *Ananl. Biochem.* 231, 247-255), in DNA sequencing (Smith et al. (1986) *Nature* 321, 674-679; Prober et al. (1987) *Science* 238, 336-343; Li et al. (1999) *Bioconjugate Chem.* 10, 241-245), in fluorescence in-situ hybridization (Denijn et al. (1992) *APMIS* 100, 669-681; Wiegant et la. (2000) *Genome Res.* 10, 861-865), and for reading of DNA arrays for gene expression (Lipshutz et al. (1999) *Nat. Genet. Suppl.* 0.1, 20-24; Ferea et al. (1999) *Curr. Opin. Genet. Dev.* 9, 715-722). Extrinsic fluorophores are used with DNA because DNA absorbs in the UV region so near 260 nm. The short absorption wavelength is now less of an obstacle because UV solid state lasers have become available. Nonetheless, the intrinsic fluorescence from DNA is of little practical usefulness because of the low quantum yields of $10^{-4}$ to $10^{-5}$ (Vigny et al. (1974) *Photochem. Photobiol.* 20, 345-349; Morgan et al. (1980) *Photochem. Photobiol.* 31, 101-113). Because the intrinsic emission from DNA, nucleotides and nucleic acid bases is very weak (Kneipp et al. (1999) *Curr. Science* 77, 915-924; Nie et al. (1997) *Science* 275, 1102-1106; Michaels et al. (1999) *J. Am. Chem. Soc.* 121, 9932-9939), it is difficult to observe the intrinsic fluorescence even with modern instrumentation (Gersten et al. (1985) *Surface Science* 158, 165-189; Lakowicz (2001) *Anal. Biochem.* 298, 1-24).

Some of the fluorescence techniques used to detect the presence of molecules include Resonance Energy Transfer (RET), immunofluorescent assays, and fluorescence in situ hybridization. Detection of the molecule of interest is generally limited by the properties of the fluorophore used. In some cases, labeling a biomolecule with an extrinsic fluorophore can alter the biological activity of the biomolecule potentially creating experimental artifacts. Problems with current fluorescent techniques stem in part from the low fluorescent intensities of commonly used fluorophores. Additionally, background fluorescence can be significant when using low wavelength excitation radiation required by some fluorophores or when large quantities of fluorophore are required.

DNA sequencing techniques using fluorescent dyes as markers have their maximum emission spectra in the visible range, the DNA is subject to irradiation in the visible spectra, and visible spectra detectors and light sources are used. Generally photomultipliers tubes are used for detection. As a result, these DNA sequencing techniques have several disadvantages including high costs resulting from the high cost of the lasers used to excite the fluorescent markers which typically emit in the visible region of light spectrum and the high noise to signal ratio due to the background interferences by biomolecules.

Thus, there is a need for compositions and methods for increasing the fluorescence intensity of biomolecules.

There is also a need for compositions and methods for increasing the intrinsic fluorescence of biomolecules.

Another need exists for compositions and methods for manipulating the fluorescence emission intensity of a biomolecule in response to an amount of exciting radiation.

Yet another need exists for methods and compositions for manipulating the radiative decay rate of biomolecules.

BRIEF SUMMARY OF THE INVENTION

One aspect of the present invention is directed to a biomolecule in combination with a metal particle, wherein the metal particle and the biomolecule are positioned at a distance apart sufficient to enhance intrinsic emission of electromagnetic radiation from the biomolecule in response to an amount of exciting electromagnetic radiation. Exemplary biomolecules include, but are not limited to, purines, pyrimidines, nucleic acids, oligonucleotides, peptide nucleic acids, RNA, DNA, amino acids, proteins, peptides, vitamins, lipids, carbohydrates, steroids and antibodies. Exemplary metals include, but are not limited to, rhenium, ruthenium, rhodium, palladium, silver, copper, osmium, iridium, platinum, and gold. The present invention is predicated on the surprising discovery that the fluorescence intensity of a biomolecule can be manipulated by varying the distance between the biomolecule and a metal particle. It will be appreciated by one of ordinary skill in the art that the scope of the present invention includes increasing the intrinsic fluorescence of a biomolecule as well as the fluorescence of a biomolecule labeled with extrinsic probes. The extrinsic fluorescence of a biomolecule includes but is not limited to the fluorescence of a fluorophore conjugated to the biomolecule. Such extrinsic fluorophores can be covalently or non-covalently attached to the biomolecule. Other aspects of the present invention describe novel compositions and methods for the detection of biomolecules. The present invention overcomes the problems associated with background fluorescence because the signal to noise ratio is increased when the fluorescence intensity of the biomolecule is increased. Additionally, expensive lasers are not required, thereby reducing costs. Extrinsic fluorophores may not be required making fluorescence assays of biomolecules quicker and less expensive.

Another aspect of the present invention provides a method for increasing the intrinsic fluorescence of a biomolecule including the step of positioning a metal particle and the biomolecule at a distance apart sufficient to increase the electromagnetic emission from the biomolecule in response to an amount of exciting radiation. It will be appreciated that the present invention includes positioning of a biomolecule adjacent to a metal particle or positioning a metal particle adjacent to biomolecule in any of the disclosed embodiments.

Still another aspect of the present invention provides a method for detecting a biomolecule including the steps of positioning a metal particle and a biomolecule at a distance apart sufficient to manipulate the electromagnetic emission from the biomolecule, exposing the biomolecule to an amount of exciting radiation, and detecting the electromagnetic emission from the biomolecule.

Yet another aspect provides a method for manipulating fluorescence intensity of a biomolecule including the steps of increasing the rate of radiative decay of the biomolecule by positioning the biomolecule adjacent to a metal particle, and exposing the biomolecule to an amount of exciting radiation. By increasing the rate of radiative decay, the fluorescence intensity of the biomolecule can be increased.

Another aspect of the present invention discloses a method for detecting the presence of a nucleic acid sequence in a sample including the steps of providing a sample, adding a nucleic sequence linked to a metal particle, exposing the sample to an amount of exciting radiation, detecting the fluorescence, and determining the presence of a nucleic acid sequence based on the detection of the fluorescence.

Still another aspect provides a method for increasing the fluorescence intensity of a fluorescently labeled biomolecule including the steps of labeling a biomolecule with a fluorophore, positioning the labeled biomolecule next to a metallic particle such that in response to an amount of exciting radiation, the fluorophore emits radiation.

Yet another aspect provides a method for increasing fluorescence energy transfer on a fluorescently labeled biomolecule including the steps of labeling a first biomolecule with a donor fluorophore and labeling a second biomolecule with an acceptor fluorophore, positioning both the first labeled biomolecule and the second labeled biomolecule adjacent to a metal particle such that in response to an amount of exciting radiation, the donor fluorophore transfers energy to the acceptor fluorophore causing the acceptor fluorophore to emit electromagnetic radiation.

Another aspect provides a method for increasing fluorescence energy transfer on a fluorescently labeled biomolecule including the steps of labeling a biomolecule with a donor fluorophore and an acceptor fluorophore, positioning the labeled adjacent to a metal particle such that in response to an amount of exciting radiation, the donor fluorophore transfers energy to the acceptor fluorophore causing the acceptor fluorophore to emit electromagnetic radiation.

Another aspect of the present invention provides a method for increasing the fluorescent intensity of a fluorophore including the steps of positioning a fluorophore adjacent to a metal particle, and exciting the fluorophore with a plurality of photons (this process is referred to as multi-photon excitation).

Another aspect of the present invention provides a method for increasing the fluorescent intensity of a biomolecule including the steps of positioning a biomolecule adjacent to a metal particle, and exciting the biomolecule with a plurality of photons.

Yet another aspect of the present invention provides a method for selectively enhancing a region of electromagnetic emission of a sample including the steps of directing a metal particle to a region of interest in the sample, and providing an amount of exciting radiation in the sample.

Another aspect of the invention provides a method for selectively enhancing the region of electromagnetic emission of a sample including the steps of directing a metal particle to a region of interest in the sample, contacting the sample with a fluorophore, and exposing the sample to an amount of exciting radiation.

For a better understanding of the present invention, together with other and further objects thereof, reference is made to the following description, taken in conjunction with the accompanying drawings, and its scope will be pointed out in the appending claims.

BRIEF DESCRIPTION OF THE DRAWINGS

FIGS. 4A-4C are a graphs showing frequency-domain intensity decays of rhodamine B under various conditions.

FIGS. 7A-7D are emission spectra of Erb, BF, [Ru(bpy)$_3$]$^{2+}$, and [Ru(phen)$_2$dppz]$^{2+}$ between silver island films (S) and between uncoated quartz plates (Q).

FIG. 9 shows that silver island particles have a greater enhancement (I$_S$/I$_Q$) on [Ru(phen)$_2$dppz]$^{2+}$ in solutions having more water than DMF. Thus, silver island films have a greater enhancement of fluorescence intensity on weak or quenched fluorophores than on strong or non-quenched fluorophores.

FIGS. 24A-24C are the frequency-domain intensity decays of DAPI in calf thymus DNA labeled with both DAPI and PI in a cuvette (24A), between uncoated quartz plates (24B), and between silver islands (24C).

FIGS. 29A and 29B are frequency-domain intensity decays of rhodamine B with two photon excitation between uncoated quartz plates (29A) and between silver island films (29B).

FIGS. 37A-C are an exemplary embodiment of an energy transfer immunoassay using donor and acceptor-labeled antibodies.

FIG. 38A is an exemplary apparatus for surface plasmon excitation and FIG. 38B is a graph of the angular distribution of the fluorescence from rhodamine 6G.

DETAILED DESCRIPTION OF THE INVENTION

Abbreviations

Figure 1A:
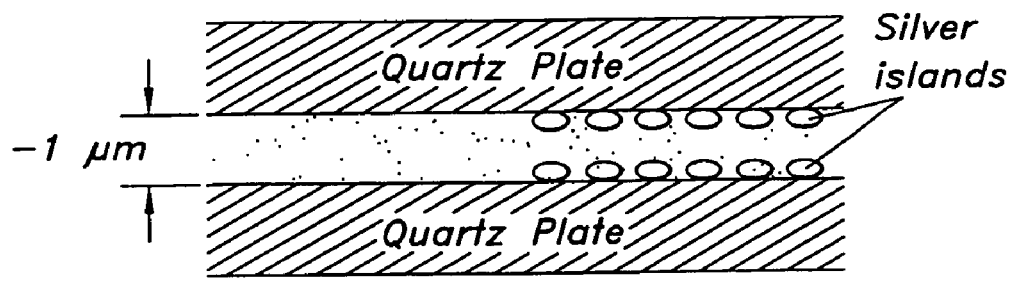
FIGS. 1A and 1B depict silver metal islands on a quartz surface and its absorption spectrum, respectively.

AO acridine orange
BF Basic Fucsin
bpy 2,2'-bipyridine
CT calf thymus
DAPI 4',6-diamidino-2-phenylindole
dppz dipyrido[3,2-a:2',3'-c]phenazine
DMF Dimethylformamide
ErB Erythrosin B
phen 9,10-phenanthroline
prodan 6-Propionyl-2-(dimethylamino)naphthalene
Py2 Pyridine 2
R6G Rhodamine 6G
RhB Rhodamine B
RB Rose Bengal
RET Resonance energy transfer
SERS Surface-enhanced Raman scattering
SIF Silver island films
SR101 Sulforhodamine 101
A acceptor
D donor
DAPI 4',6-diamidino-2-phenylindole
FD frequency-domain
PI propidium iodide
RET resonance energy transfer

DEFINITIONS

The term "fluorophore" means any substance that emits electromagnetic energy such as light at a certain wavelength (emission wavelength) when the substance is illuminated by radiation of a different wavelength (excitation wavelength). Extrinsic fluorophores refers to fluorophores bound to another substance. Intrinsic fluorophores refers to substances that are fluorophores themselves. Exemplary fluorophores include but are not limited to those listed in the Molecular Probes Catalogue which is incorporated by reference herein. Representative fluorophores include but are not limited to Alexa Fluor® 350, Dansyl Chloride (DNS-Cl), 5-(iodoacetamida)fluoroscein (5-IAF); fluoroscein 5-isothiocyanate (FITC), tetramethylrhodamine 5- (and 6-)isothiocyanate (TRITC), 6-acryloyl-2-dimethylaminonaphthalene (acrylodan), 7-nitrobenzo-2-oxa-1,3,-diazol-4-yl chloride (NBD-Cl), ethidium bromide, Lucifer Yellow, 5-carboxyrhodamine 6G hydrochloride, Lissamine rhodamine B sulfonyl chloride, Texas Red™ sulfonyl chloride, BODIPY™, naphthalamine sulfonic acids including but not limited to 1-anilinonaphthalene-8-sulfonic acid (ANS) and 6-β-toluidinyl)naphthalene-2-sulfonic acid (TNS), Anthroyl fatty acid, DPH, Parinaric acid, TMA-DPH, Fluorenyl fatty acid, Fluorescein-phosphatidylethanolamine, Texas red-phosphatidylethanolamine, Pyrenyl-phophatidylcholine, Fluorenyl-phosphotidylcholine, Merocyanine 540,1-(3-sulfonatopropyl)-4-[β-[2[(di-n-butylamino)-6naphthyl]vinyl]pyridinium betaine (Naphtyl Styryl), 3,3'dipropylthiadicarbocyanine (diS-$C_3$-(5)), 4-(p- dipentyl aminostyryl)-1-methylpyridinium (di-5-ASP), Cy-3 Iodo Acetamide, Cy-5-N-Hydroxysuccinimide, Cy-7-Isothiocyanate, rhodamine 800, IR-125, Thiazole Orange, Azure B, Nile Blue, A1 Phthalocyanine, Oxaxine 1, 4',6-diamidino-2-phenylindole (DAPI), Hoechst 33342, TOTO, Acridine Orange, Ethidium Homodimer, N(ethoxycarbonylmethyl)-6-methoxyquinolinium (MQAE), Fura-2, Calcium Green, Carboxy SNARF-6, BAPTA, coumarin, phytofluors, Coronene, and metal-ligand complexes. Representative intrinsic fluorophores include but are not limited to organic compounds having aromatic ring structures including but not limited to NADH, FAD, tyrosine, tryptophan, purines, pyrimidines, lipids, fatty acids, nucleic acids, nucleotides, nucleosides, amino acids, proteins, peptides, DNA, RNA, sugars, and vitamins. Additional suitable fluorophores include enzyme-cofactors; lanthanide, green fluorescent protein, yellow fluorescent protein, red fluorescent protein, or mutants and derivates thereof.

The term "biomolecule" means any carbon based molecule occurring in nature or a derivative of such a molecule. The biomolecule can be in active or inactive form. "Active form" means the biomolecule is in a form that can perform a biological function. "Inactive form" means the biomolecule must be processed either naturally or synthetically before the biomolecule can perform a biological function. Exemplary biomolecules include nucleic acids, aromatic carbon ring structures, NADH, FAD, amino acids, carbohydrates, steroids, flavins, proteins, DNA, RNA, oligonucleotides, peptide nucleic acids, fatty acids, sugar groups such as glucose etc., vitamins, cofactors, purines, pyrimidines, formycin, lipids, phytochrome, phytofluor, and phycobiliproptein.

The term "amount of exciting radiation" means an amount of radiation that causes a molecule to emit radiation.

EXEMPLARY EMBODIMENTS

One embodiment of the present invention is directed to a biomolecule in combination with a metal particle, wherein said metal particle and the biomolecule are positioned at a distance apart sufficient to adjust, preferably enhance, intrinsic emission of electromagnetic radiation from the biomolecule in response to an amount of exciting electromagnetic radiation. Exemplary biomolecules include but are not limited to purines, pyrimidines, nucleic acids, oligonucleotides, peptide nucleic acids, RNA, DNA, amino acids, flavins, proteins, peptides, vitamins, lipids, antibodies, and aromatic carbon ring structures. Preferred biomolecules and fluorophores of the present invention have quantum yields of less than about 0.8, more preferably of less than about 0.5, and most preferably of less than about 0.2. Exemplary metals include copper and noble metals such as rhenium, ruthenium, rhodium, palladium, silver, osmium, iridium, platinum, and gold. Similarly, another embodiment provides a composition of matter including a biomolecule in combination with a metal surface wherein said metal surface and the biomolecule are positioned at a distance apart sufficient to adjust, preferably enhance, intrinsic emission of electromagnetic radiation from the biomolecule in response to an amount of exciting electromagnetic radiation. Still, another embodiment provides that the metal surface can be a periodic metal surface.

The present invention is predicated on the surprising discovery that the fluorescence intensity of a biomolecule can be manipulated by varying the distance between the biomolecule and a metal particle. Indeed, it has been discovered that the intrinsic fluorescence of a biomolecule can be increased by at least about 80 fold to about 140 fold when the biomolecule is positioned adjacent to a metal particle. Preferably the metal particle and biomolecule are separated by a distance of about 0.50 Å to about 2000 Å, most preferably from about 50 Å to about 200 Å. In another embodiment, the metal particle is sub-wavelength in size, typically in the range of about 50 Å to about 300 Å. The metal particles can be spheroid, ellipsoid, or of any other geometry. The metal particles can be suspended in a colloid or combination of colloids, alloys, or combinations of more than one metal. The metal particles can be placed on surfaces as thin films, or deposited on surfaces to form small islands. The surfaces can be metallic or non-metallic. Additionally, the metal particles can be coated with polymers, gels, adhesives, oxides, or biologic material. Exemplary coatings include substances that increase the binding of the metal particle to surfaces or other molecules. In one embodiment, the metal particles can be modified on its surface to facilitate binding to non-metallic molecules and biomolecules. In an exemplary embodiment, metal particles, preferably noble metals, most preferably silver, are chemically reduced on a surface. Chemical reduction can be accomplished using known techniques. Exemplary surfaces include but are not limited to glass or quartz.

In another embodiment, the biomolecule and the metal particle can be attached to each other via an intermediate of a length sufficient to have a desired effect on the intrinsic fluorescence of the biomolecule. The attachment can be covalent or non-covalent. Additionally, the metal and biomolecule can be stably linked or can be linked such that the two can become separated as a result of a chemical reaction, enzymatic reaction, or photoreaction. For example, a biomolecule linked to a metal particle can be internalized within a cell, cellular organelle, or other compartment. Once internalized, the linked biomolecule can be subjected to enzymatic or chemical reaction resulting in the complete separation of the metal particle from the biomolecule. Exemplary enzymatic reactions include, but are not limited to, non-specific esterase reactions, and exemplary chemical reactions include but are not limited to hydrolysis, oxidation, or substitution. Once separated, the biomolecule can become undetectable or less detectable because its intrinsic fluorescence is no longer amplified by the metal particle. If the intrinsic fluorescence of the biomolecule is desired to be quenched, the biomolecule and the metal particle can be separated by a distance of about 0 to less than 50 Å. If the intrinsic fluorescence of the biomolecule is to be increased, the biomolecule and the metal particle can be separated by a distance of about 50 Å to about 2000 Å, more preferably from about 50 Å to about 200 Å. Thus, the fluorescence intensity of a biomolecule can be manipulated by varying the distance separating the metal particle from the biomolecule.

It will be appreciated by one of ordinary skill in the art that the scope of the present invention includes increasing the extrinsic fluorescence of a biomolecule as well as the intrinsic fluorescence of the biomolecule. The extrinsic fluorescence of a biomolecule includes but is not limited to the fluorescence of a fluorophore conjugated to the biomolecule. Such conjugated fluorophores can be covalently or non-covalently attached to the biomolecule. An increase or decrease in fluorescence intensity in the present invention means an increase or decrease in intrinsic or extrinsic fluorescence intensity when the biomolecule or fluorophore is in combination with a metal particle compared to the intrinsic or extrinsic fluorescence intensity of the biomolecule or fluorophore in the absence of a metal particle.

Another embodiment of the present invention provides a method for increasing the intrinsic fluorescence of a biomolecule including the step of positioning the biomolecule and a metal particle at a distance apart sufficient to increase the electromagnetic emission from the biomolecule in response to an amount of exciting radiation. It will be appreciated that the present invention includes positioning of a biomolecule adjacent to a metal particle or positioning a metal particle adjacent to the biomolecule in any of the disclosed embodiments. In an exemplary embodiment, the biomolecule and the metal particle are separated by a distance of about 50 Å to about 2000 Å, preferably from about 50 Å to about 200 Å, to increase the intrinsic fluorescence of the biomolecule or separated by a distance of less than about 50 Å if the intrinsic fluorescence is to be quenched. In other embodiments, the metal particles can be fixed on a surface, and the biomolecule positioned adjacent to such a surface. Such surfaces can form a part of cuvette or can be an insert capable of being placed within a cuvette.

Positioning of the biomolecule or metal particle at a desired distance can be achieved by using a linker that physically links the two. Linkers can be one intervening atom or molecule, preferably carbon chains of at least one carbon atom. Other linkers include but are not limited to at least one amino acid. Additionally, other chemical linkers known in the art can be used. The linkers can be of any length, preferably of up to about 200 Å depending the desired effect on fluorescence. In other embodiments, the metal particle can be positioned adjacent to the biomolecule using electromagnetic forces, charged fields, gravity or other known methods. In one example, voltage can be regulated to manipulate the position of the metal particle, or linked biomolecule and metal particle. Alternatively, the biomolecule can be positioned using electromagnetic fields, electric currents, voltage, or gravity.

Yet another embodiment of the present invention provides a method for detecting a biomolecule including the steps of positioning said biomolecule and a metal particle at a distance apart sufficient to manipulate the electromagnetic emission from the biomolecule, exposing the biomolecule to an amount of exciting radiation, and detecting the electromagnetic emission from the biomolecule. Monitoring, detecting, and quantifying fluorescence is known in the art. See for example Joseph R. Lakowicz. Principles in Fluorescence Spectroscopy, Plenum Publishers 1999 which is incorporated by reference herein in its entirety.

Briefly, fluorescence can be detected using devices including, but not limited to, a spectrofluorometer having a light source and detector. Light sources can include arc lamps and lasers. Detectors can include photomultiplier tubes. Additionally, it is advantageous for the device to have a monochromator so that specific wavelengths of light may be used to excite a molecule or to detect emissions at a specific wavelength. When a sample containing a fluorophore is placed in the spectrofluorometer and exposed to an amount of exciting radiation, the fluorophore emits radiation that is detected by a photomultiplier tube. The fluorescence intensity of a biomolecule can be increased in response to an amount of exciting radiation when the distance between the metal particle and the biomolecule is from about 50 Å to about 2000 Å, preferably from about 50 Å to about 200 Å. Alternatively, the fluorescence intensity of the biomolecule can be reduced when the distance between the biomolecule and the metal particle is less than about 50 Å.

Yet another embodiment provides a method for manipulating fluorescence intensity of a biomolecule including the steps of increasing the rate of radiative decay of the biomolecule by positioning the biomolecule adjacent to a metal particle, and exposing the biomolecule to an amount of exciting radiation. By increasing the rate of radiative decay, the fluorescence intensity of the biomolecule can be increased. It has been discovered that by manipulating the distance separating a biomolecule and a metal particle, the radiative decay of the biomolecule can also be manipulated.

Another embodiment of the present invention discloses a method for detecting the presence of a nucleic acid sequence in a sample including the steps of providing a sample, adding a nucleic sequence linked to a metal particle, exposing the sample to an amount of exciting radiation, detecting the fluorescence, and determining the presence of the nucleic acid sequence based on the detection of the fluorescence. In one embodiment, the nucleic acid sequence linked to a metal particle is single stranded. In other embodiments, the nucleic acid sequence linked to the metal particle is double stranded. In a preferred embodiment, the nucleic acid sequence linked to a metal particle is less than two hundred base pairs in length, more preferably, less than 100 base pairs in length, most preferably less than 50 base pairs in length, even more preferably, about twenty or less nucleic acids in length. The nucleic acids can be deoxyribonucleic acids, ribonucleic acids, or chemically modified nucleic acids such as peptide nucleic acids and the like.

Methods for the hybridization of nucleic acids are known in the art. See for example Nonradioactive In Situ Hybridization Application Manual at biochem.roche.com/prod_inf/manuals/insitu/insi_toc.htm incorporated by reference in its entirety. Historically, the detection of hybridized nucleic acid used labeled nucleic acid probes to hybridize to a nucleic acid sample. For example, in a Southern blot technique, a nucleic acid sample is separated in an agarose gel based on size and affixed to a membrane, denatured, and exposed to the labeled nucleic acid probe under hybridizing conditions. If the labeled nucleic acid probe forms a hybrid with the nucleic acid on the blot, the label is bound to the membrane. Probes used in Southern blots have been labeled with radioactivity, fluorescent dyes, digoxygenin, horseradish peroxidase, alkaline phosphatase and acridinium esters.

The present invention discloses a novel method for the detection of nucleic acid sequences by increasing the intrinsic fluorescence of the nucleic acids. This increase is accomplished by linking the nucleic acid to a metal, preferably a noble metal. The present invention does not require the use of an extrinsic probe. Rather when the nucleic acid sequence linked to a metal particle is added to a sample, this sequence can hybridize to complementary nucleic acid sequences in the sample. In a preferred embodiment the nucleic acid sequence to be detected can be affixed to a solid support. Exemplary solid supports include films, membranes, columns, nitrocellulose, plastic, quartz, glass, or metal. The sample is irradiated with an amount of exciting radiation. Fluorescence detected in the sample or, for example, on the solid support would indicate that the nucleic acid linked to the metal particle has hybridized to a complementary nucleic acid sequence present in the sample. Therefore, the sample contains the nucleic acid sequence of interest. Nucleic acids not linked to a metal particle would not contribute significantly to fluorescence emission because the quantum yield of nucleic acids is too low. It will be appreciated that the nucleic hybridization detected by the present invention can occur in situ. Additionally, it will be appreciated that the detection of the nucleic acid can be based on increasing the fluorescence intensity of an extrinsic fluorophore attached to a nucleic acid by positioning the fluorophore adjacent to a metal particle. Increasing the intrinsic fluorescence of nucleic acids can be useful in DNA arrays or gene chips.

In another embodiment, the present invention provides a method for identifying nucleic acids, the method including the steps of positioning a nucleic acid adjacent to a metal particle, irradiating the nucleic acid, detecting the fluorescence emission from the nucleic acid, and identifying the nucleic acid based on the fluorescence emission. The identification of nucleic acids using the intrinsic fluorescence of the nucleic acid eliminates the requirement for extrinsic probes. In one embodiment, the background fluorescence is not problematic because the intrinsic fluorescence can be increased by about 80 fold thereby reducing the noise to signal ratio. In another embodiment, the nucleic acid can be identified based on the emission spectra obtained from monitoring the fluorescence of the sample. Thus, the sequence of nucleic acids in a sample can be determined by sequentially removing a nucleic acid, positioning the nucleic acid adjacent to metal particle, irradiating the nucleic acid with an amount of exciting radiation, detecting the emitted radiation, and correlating the emitted radiation with the nucleic acid base. Methods for sequentially removing a single nucleic acid form a nucleic acid sequence such as an oligonucleotide are known in the art and include sequential digestion, hydrolysis, and chemical cleavage. The nucleic acids can be positioned adjacent to a metal particle by causing the stream of a fluid sample containing a nucleic acid to pass near a surface containing the metal particle. Such surfaces can be thin films or islands of metal that form part of a sample chamber. The irradiation of the nucleic acid can be timed to coincide with the positioning of the nucleic acid adjacent to the metal. The nucleic acids can be irradiated with one or more wavelengths. In a preferred embodiment, the nucleic acids are excited at wavelengths below 300 nm, preferably from 280 to about 295 nm. In another embodiment, the excitation wavelength is near 520 nm for multi-photon excitation.

It will be appreciated by those of ordinary skill in the art, that the methods and compositions of the present invention can be used in polymerase chain reaction techniques. Polymerase chain reaction techniques are will known in the art. Nucleic acids coupled to metal particles, preferably noble metal particles, can be added to the polymerase chain reaction mixtures. The coupled nucleic acids can be incorporated into the growing oligonucleotide chain, and in response to an amount of exciting radiation, the fluorescence of the coupled nucleic acid will be detectable enabling the detection of the polymerase chain reaction product.

Still another embodiment provides a method for increasing the fluorescence intensity of a fluorescently labeled biomolecule including the steps of labeling a biomolecule with a fluorophore, positioning the labeled biomolecule adjacent to a metallic particle such that in response to an amount of exciting radiation, the fluorophore emits radiation, preferably detectable amounts of radiation. In a preferred embodiment, the fluorophore has a quantum yield of less than 0.8, preferably less than 0.5, more preferably less than 0.2, and most preferably less than 0.1. In this embodiment, the fluorescence intensity of an extrinsic fluorophore can be used to detect the biomolecule.

Yet another embodiment provides a method for increasing fluorescence energy transfer on a fluorescently labeled biomolecule including the steps of labeling a first biomolecule with a donor fluorophore and labeling a second biomolecule with an acceptor fluorophore, positioning the labeled biomolecules adjacent to a metal particle such that in response to an amount of exciting radiation, the donor fluorophore transfers energy to the acceptor fluorophore causing the acceptor fluorophore to emit electromagnetic radiation.

Another embodiment provides a method for increasing fluorescence energy transfer on a fluorescently labeled biomolecule including the steps of labeling a biomolecule with a donor fluorophore and an acceptor fluorophore, positioning the labeled adjacent to a metal particle such that in response to an amount of exciting radiation, the donor fluorophore transfers energy to the acceptor fluorophore causing the acceptor fluorophore to emit electromagnetic radiation.

Increases in energy transfer due to metallic particles can be used in immunoassays. Thus, in one embodiment, the compositions of the present invention can use fluorescence energy transfer to measure an affinity reaction, preferably an antibody-antigen reaction or a protein-carbohydrate interaction. Additionally, assay chambers coated with or containing metallic particles can be used to increase the efficiency or RET even between donor and acceptors to span distances over 100 Å apart. Metal enhanced energy transfer is also useful with DNA arrays or gene chips. In another embodiment, the compositions and methods of the present invention can utilize fluorescence energy transfer to measure DNA hybridization or the amount of double helical DNA. At present the arrays are read by measuring the amount of two fluorophores hybridized to the target DNA (Ferea et al. (1999) *Curr. Opin. Genetics Dev.*, 9, 715-722; Lipshutz et al. (1999). *Nature Gen. Suppl.* 1, 20-24; Hacia et al. (1998) *Molec. Psychiatry* 3, 483-492). Even though the two dyes are probably a good donor-acceptor pair, energy transfer does not normally occur. The use of DNA arrays on metallic surfaces provides a new type of DNA array analysis based on RET between donors and acceptors positioned at long distances.

Methods and procedures for producing biochips, gene chips or microarrays are known in the art. For example, U.S. Pat. No. 6,174,683 discloses methods and compositions relating to "biochips' and the formation of "biochips" and is incorporated herein in its entirety. Nucleic acid probes are affixed to a microarray surface. In the present invention, the microarray surface is a metal surface, preferably a noble metal, most preferably a silver surface. The surface can be coated with metal islands as describe above. Generally, total RNA is prepared from a sample or samples to determine the pattern of gene expression. These samples can be different cell lines, tumor samples, normal vs. disease, control or drug-treated, etc. In most cases, a minimum of about 1 µg of polyA+ RNA or about 5 µg of total RNA is required. However, as little as 0.2 µg of "good quality" polyA+ RNA can be used. As a general rule, $1 \times 10^6$ tissue culture cells should yield 10-15 µg of total RNA.

Using Reverse Transcriptase, the RNA is converted into cDNA. At this point the cDNA can be labeled directly by incorporation of fluorescently-tagged dNTPs. More commonly, the cDNA is prepared using an oligo-dT primer that incorporates a T7 RNA polymerase promoter. The cDNA is then used in a subsequent step to make fluorescently-tagged copy RNA, using T7 RNA polymerase. In general, at least about 5 µg of labeled cRNA or cDNA is required for hybridizing to each microarray. However, the probes can be reused. For example, one labeled probe can be used sequentially to hybridize to five separate arrays.

The fluorescently-labeled probes are hybridized to the microarrays, much as radioactive probes are hybridized to conventional dot-blots. The fluorescence of the labeled probe will increase in response to an amount of exciting radiation when the probe hybridizes to a complementary sequence because it is positioned near the metal microarray surface, preferably from about 50 Å to about 2000 Å, more preferably from about 50 Å to about 200 Å, from the metal surface. In another embodiment, the probe can be labeled with a donor and an acceptor fluorophore. When the labeled probe hybridizes to its complement on the microarray surface, it is positioned near the metal microarray surface, preferably from about 50 Å to about 2000 Å, more preferably from about 50 Å to about 200 Å, from the metal surface. In this position, the fluorescence energy transfer from the donor to the acceptor molecule is increased in response to an amount of exciting radiation enabling detection of the labeled probe. Detection of the labeled probe on the microarray indicates that the probe has hybridized to a complementary sequence further indicating expression of the corresponding gene. In still another embodiment, the nucleic acid sequence affixed to the metal coated microarray surface can be labeled with a donor or acceptor molecule, and the nucleic acid probe can be labeled with acceptor or donor molecule respectively such that when the nucleic acid probe hybridizes with a labeled nucleic acid sequence on the microarray surface, the fluorescence energy transfer from the donor molecule to the acceptor molecule is increased in response to an amount of exciting radiation.

After washing, the microarrays are analyzed using a fluorescent scanner: a cross between a typical flat-bed scanner and a confocal microscope. The data is an image of the fluorescent spots on the microarray. The image can be analyzed using software that identifies the spots and calculates the intensity of the fluorescence in each one. By comparing the intensities obtained with two different probes (e.g. control vs. drug-treated), one can determine how the expression of each gene in the array changes.

In other embodiment, proteins can be arrayed on metal surfaces, preferably noble metal surfaces, most preferably silver coated surfaces. Generally, to array proteins on a surface, a GMS 417 Arrayer (Affymetrix, Santa Clara, Calif.) or other suitable device can be used. The arrayer picks up about a microliter of sample from four wells of a 96- or 384-well plate and deposits about 1 nanoliter of each sample at defined locations on a series of glass microscope slides. The arrayer can use a pin and ring system: the samples are picked up in small rings that each hold about 1 microliter and a solid pin (150 μm diameter) then punches repeatedly through the ring to deposit the proteins on the slides. To prevent evaporation of the nanodroplets, 40% glycerol is included in the protein samples. Nanoliter droplets of 40% glycerol remain hydrated, even when left exposed to the atmosphere overnight.

To study protein function, it is necessary to immobilize the proteins in a way that preserves their folded conformations. In addition, it is preferred to minimize nonspecific binding of other proteins to the surface in subsequent steps. To accomplish these goals, chemically derivatized slides can be used. For most applications, slides that have been treated with an aldehyde-containing silane reagent are used. These slides can also be purchased from TeleChem International under the trade name SuperAldehyde Substrates. The aldehydes react readily with primary amines on the proteins to form a Schiff's base linkage. Because typical proteins display many lysines on their surface as well as the generally more reactive alpha-amine at their amino termini, they can attach to the slide in a variety of orientations, permitting different sides of the protein to interact with other proteins or small molecules in solution. Following attachment of the proteins to these slides, the unreacted aldehydes are quenched and nonspecific binding minimized by immersing the slides in a buffer containing bovine serum albumin (BSA).

Although appropriate for most applications, aldehyde slides cannot be used when peptides or very small proteins are printed, presumably because the BSA obscures the molecules of interest. For such applications, BSA-NHS slides that are fabricated by first attaching a molecular layer of BSA to the surface of glass slides and then activating the BSA with N,N'-disuccinimidyl carbonate are used. The activated lysine, aspartate, and glutamate residues on the BSA react readily with surface amines on the proteins to form covalent urea or amide linkages. The slides are then quenched with glycine.

Aldehyde slides can be purchased from TeleChem International (Cupertino, Calif.). BSA-NHS slides, displaying activated amino and carboxyl groups on the surface of an immobilized layer of bovine serum albumin (BSA), can be fabricated as follows. 10.24 g N,N'-disuccinimidyl carbonate (100 mM) and 6.96 ml N,N-diisopropylethylamine (100 mM) were dissolved in 400 ml anhydrous N,N-dimethylformamide (DMF). 30 CMT-GAP slides (Corning Incorporated, Corning, N.Y.), displaying amino groups on their surface, were immersed in this solution for 3 hours at room temperature. The slides are rinsed twice with 95% ethanol and then immersed in 400 ml of phosphate buffered saline (PBS), pH 7.5 containing 1% BSA (w/v) for 12 hour at room temperature. The slides are rinsed twice with ddH$_2$O, twice with 95% ethanol, and centrifuged at 200 g for 1 min to remove excess solvent. The slides are then immersed in 400 ml DMF containing 100 mM N,N'-disuccinimidyl carbonate and 100 mM N,N-diisopropylethylamine for 3 hour at room temperature. The slides are rinsed four times with 95% ethanol and centrifuged as above to yield BSA-NHS slides. The slides are stored in a desiccator under vacuum at room temperature for up to two months without noticeable loss of activity.

Proteins are dissolved in 40% glycerol, 60% PBS, pH 7.5 at a concentration of 100 μg/ml unless indicated otherwise. The proteins are spotted on aldehyde slides using a GMS 417 Arrayer (Affymetrix, Santa Clara, Calif.). Following a 3 hours incubation in a humid chamber at room temperature, the slides are inverted and dropped onto a solution of PBS, pH 7.5 containing 1% BSA (w/v). After 1 minute, the slides were turned right side up and immersed in the BSA solution for 1 hour at room temperature with gentle agitation. Following a brief rinse in PBS, the slides are ready for further processing.

Proteins of interest can be labeled with a fluorophore and hybridized to the array. The fluorescence of the fluorophore will increase in response to an amount of exciting radiation when the labeled protein is near the metal surface, preferably form about 50 Å to about 2000 Å, more preferably from about 50 Å to about 200 Å, from the metal surface. In another embodiment, the protein probe of interest can be labeled with an acceptor and donor fluorophore such that when the protein probe binds to a protein on the microarray, the protein probe is positioned near the metal surface such that fluorescence energy transfer is increased from the donor to the acceptor molecule. In still another embodiment, the protein affixed to the metal coated microarray surface can be labeled with a donor or acceptor molecule, and the protein probe can be labeled with acceptor or donor molecule respectively such that when the protein probe hybridizes with a labeled protein on the microarray surface, the fluorescence energy transfer from the donor molecule to the acceptor molecule is increased in response to an amount of exciting radiation.

Thus, another embodiment of the present invention provides a microarray system including a solid support, wherein the solid support is coated with metal particles, preferably noble metal particles, most preferably with silver particles; and a matrix having an array of biomolecules, preferably nucleic acids or amino acids, at desired lengths attached to the support such that when a labeled probe hybridizes to a sequence of the biomolecules, preferably such that the label is positioned about 50 Å to about 2000 Å, preferably from about 50 Å to about 200 Å from a metal particle, the fluorescence of the labeled probe is increased in response to an amount of exciting radiation. The term "probe" includes proteins, nucleic acids, amino acids, oligonucleotide, peptide nucleic acids, peptides, or other molecules that hybridize, bind, or are complementary to the molecules of the matrix attached to the metal coated surface of the microarray.

The efficiency of light harvesting assemblies based on RET (Adronov et al. (2000) *J. Am. Chem. Soc.* 122, 1175-1185; Swallen et al. (1999) *J. Molec. Structure* 485486: 585-597) can be increased or the extent of RET between donors and acceptors within cells (González et al. (1995). *Biophys. J* 69, 1272-1280; (Ng et al. (1999) *Science* 283, 2085-2089) but close to metallic particles can be increased. The phenomenon of metal-enhanced RET provides a unique opportunity of using the proximity of donor-acceptor pairs to metallic particles to modify the rates of transfer. Such effects are unique because the metal particles or surfaces, rather than the solution composition, can be used to modify the spectral properties of the probes.

Another embodiment of the present invention provides a method for increasing the fluorescent intensity of a fluorophore including the steps of positioning a fluorophore adjacent to a metal particle, and exciting the fluorophore with a plurality of photons, commonly referred to as multi-photon excitation. Typically, the fluorophore is excited with short picosecond or fentosecond laser pulses with a wavelength approximately twice the longest single photon absorption maximum. Multi-photon excitation instrumentation and methodology are known in the art, and can be found, for example, in *Topics in Fluorescence Spectroscopy*, Volume 5, *Nonlinear and Two-Photon-Induced Fluorescence*, Edited by Joseph R. Lakowicz. Plenum Press, New York, 1997, which is incorporated by reference herein in its entirety. Generally, multi-photon excitation is typically performed with a strongly focused laser light source, such as, a mode-locked titanium sapphire laser, providing pulses approximately 100 fentoseconds long, repetition rate near 80 MHz, with a wavelength range from 700 to 900 nm. Multi-photon excitation can also be accomplished with picosecond dye lasers.

Another embodiment of the present invention provides a method for increasing multi-photonic fluorescent intensity of a biomolecule including the steps of positioning a biomolecule adjacent to a metal particle, and exciting the biomolecule with a plurality of photons.

Yet another embodiment of the present invention provides a method for selectively enhancing the region of electromagnetic emission of a sample including the steps of directing a metal particle to a region of interest in the sample, and providing an amount of exciting radiation in the sample.

Another embodiment of the invention provides a method for selectively enhancing the region of electromagnetic emission of a sample including the steps of directing a metal particle to a region of interest in the sample, contacting the sample with a fluorophore, exposing the sample to an amount of exciting radiation. Exemplary metals are noble metals. The metal particle can be positioned using electric potential, magnetism, or gravity.

Still another embodiment provides a method for selectively enhancing the region of electromagnetic emission of a sample, the method including the steps of directing a metal particle to a region of interest in the sample, providing an amount of exciting radiation in the region of interest. Samples can be living cells, tissues, organs, or fluid samples in containers. The metal particle can be positioned using electromagnetic fields, or the metal particle can be linked to a protein, antibody, nucleic acid or the like. An antibody linked to a metal particle can be used to bring the metal adjacent to molecules recognized by the antibody. Thus, if the antibody recognizes a particular biomolecule, the metal can be positioned next to such biomolecule such that the fluorescence intensity of the biomolecule will increase in response to an amount of exciting radiation.

Another embodiment discloses a method for selectively enhancing the region of electromagnetic emission of a sample, said method including the steps of directing a metal particle to a region of interest in the sample, contacting the sample with a fluorophore, and exposing the sample to an amount of exciting radiation. In a preferred embodiment, the fluorophore has a quantum yield of less than 0.8, preferably less than 0.5, more preferably less than 0.2, and most preferably less than 0.1. Fluorophores with low quantum yields will not fluoresce detectably unless they are adjacent to a metal particle. Thus, when the sample is exposed to an amount of exciting radiation, only the fluorophores adjacent to a metal particle will fluoresce enough to be detectable. Still another embodiment discloses a kit for detecting the presence of an analyte comprising an antibody capable of binding to said analyte, the antibody linked to a fluorophore having a quantum yield of less than about 0.5, preferably less than about 0.2, most preferably less than about 0.1, and at least one quartz surface having metal islands deposited thereon. Exemplary antibodies are directed to proteins, peptides, and other biomolecules.

Another embodiment discloses a method for detecting an analyte, the method including the steps of labeling a first antibody with a donor, labeling a second antibody with an acceptor, contacting a sample with the first and second antibodies to form a complex with the analyte, positioning the analyte about 50 to about 2000 Å, preferably from about 50 Å to about 200 Å, from a metal particle, preferably a noble metal, providing an amount of exciting radiation, and detecting the analyte based on the increase in energy transfer from donor to acceptor. Exemplary donors are fluorophores with wavelengths which overlap the absorption spectra of the acceptor. Exemplary acceptors have absorption spectra which overlap with the emission spectra of the donors. Acceptors may also be fluorescent. Exemplary donor-acceptor pairs include fluorescein-rhodimine, DAPI-propidium iodide, and Cy3-Cy5. The antibodies can be labeled using standard techniques. In one embodiment, the complex can be positioned using gravity, electric potential, or other known force.

Example 1

Procedure for Making Metal Nanoparticle Films

Metal particles or metal particle films are known and can be produced using known methods. The following example uses silver but it will be appreciated that any metal can be used, preferably noble metals. Chemicals used to generate silver particles, silver nitrate (99+%), sodium hydroxide (pellets, 97%), ammonium hydroxide ($NH_3$ content 28-39%), and D-glucose (99.5%) were purchased from commercial suppliers and used without further purification. All procedures were performed using distilled water which was further purified by Millipore filtration. Silver islands were formed on quartz microscope slides. Quartz provided UV transmission and less autofluorescence. The quartz slides used to deposit silver particles were soaked in a 10:1 (v/v) mixture of $H_2SO_4$ (95-98%) and $H_2O_2$ (30%) overnight before the deposition. They were washed with water and air-dried prior to use.

Silver deposition was carried out in a clean 30-ml beaker equipped with a Teflon-coated stir bar. To a fast stirring silver nitrate solution (0.22 g in 26 ml of Millipore filtered water), eight drops of fresh 5% NaOH solution was added. Dark-brownish precipitates were formed immediately. Less than 1 ml of ammonium hydroxide was then added drop by drop to redissolve the precipitates. The clear solution was cooled to 5° C. by placing the beaker in an ice bath, followed by soaking the cleaned and dried quartz slides in the solution. At 5° C., a fresh solution of glucose (0.35 g in 4 ml of water) was added. The mixture was stirred for 2 min at that temperature. Subsequently, the beaker was removed from the ice bat % The temperature of the mixture was allowed to warm up to 30° C. As the color of the mixture turning from yellow-greenish to yellow, the color of the slides become greenish, the slides were removed and washed with water and bath sonicated for 1 min at room temperature. After being rinsed with water several times, the slides were stored in water for several hours prior to the experiments.

Emission spectra were obtained using a SLM 8000 spectrofluorometer. Intensity decays were measured in the frequency-domain using instrumentation described previously (Lakowicz et al. (1985) *Biophys. Chem.* 21, 61-78; Laczko et al. (1990) *Rev. Sci. Instrum.* 61, 2331-2337). For rhodamine 6G (R6G) and rose bengal (RB) the excitation was at 514 nm from the approximate 78 MHz output of a mode-locked argon ion laser. For the frequency-domain measurements the emission was observed through a 580 interference filter. For all steady state and frequency-domain measurements the excitation was vertically polarized and the emission observed through a horizontally oriented polarizer to minimize scattered light. The FD intensity decay data were analyzed in terms of the multi-exponential model $$I(t) = \sum_i \alpha_i \exp(-t/\tau_i) \quad (1)$$

where $\tau_i$ are the lifetimes with amplitudes $\alpha_i$ and $\Sigma \alpha_i = 1.0$. Fitting to the multi-exponential model was performed as described previously (Lakowicz et al. (1994) *Biophys. J.* 46, 463-477). The contribution of each component to the steady state intensity is given by $$f_i = \frac{\alpha_i \tau_i}{\sum_j \alpha_j \tau_j} \quad (2)$$

Figure 1B:
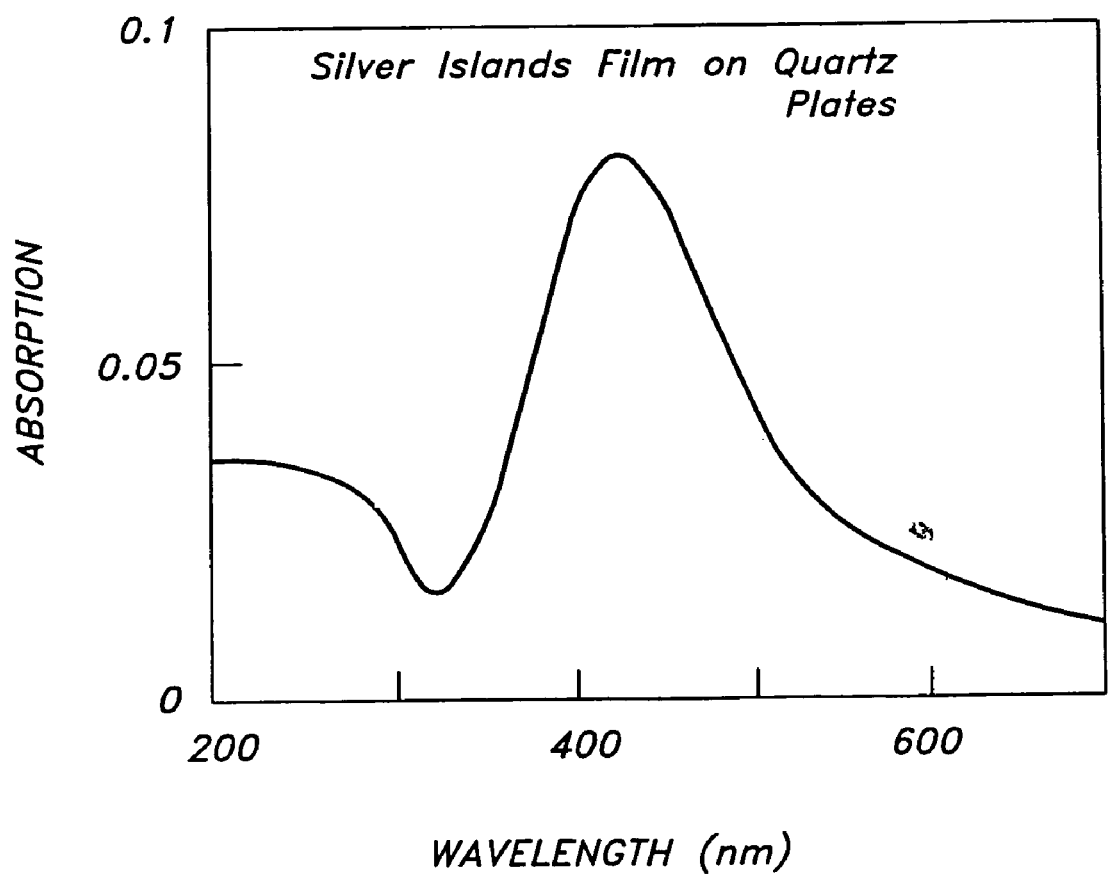

FIG. 1A shows the experimental geometry of the silver islands on quartz slides, and FIG. 1B shows the absorption spectra of silver island films. This spectrum indicates that the particles are sub-wavelength in size. In the small-particle limit the absorption maximum due to this plasmon resonance is expected to be near 380 nm (Kerker, M. (1985) *J. Colloid Interface Sci.* 105, 297-314; Mulvaney, P. (1996) *Langmuir,* 12, 788-800). The absorption maximum above 400 nm can be due to an asymmetric effective shape of the particles with an axial ratio near 1.5 to 1.0 (Kerker, M. (1985) *J. Colloid Interface Sci.* 105, 297-314) and is also consistent with silver particles with spherical dimensions near 40-50 nm (Rivas et al. (2001) *Langmuir* 17, 574-577; Jensen, et al. (2000) *J. Phys. Chem. B* 104, 10549-10556; Singer et al. (1995) *J. Opt. Soc. Am. B*, 12, 220-228). The shape and size distribution of the particles is almost certainly heterogeneous, but it is clear the particles are sub-wavelength in size.

Figures 2A, 2B, 2C:
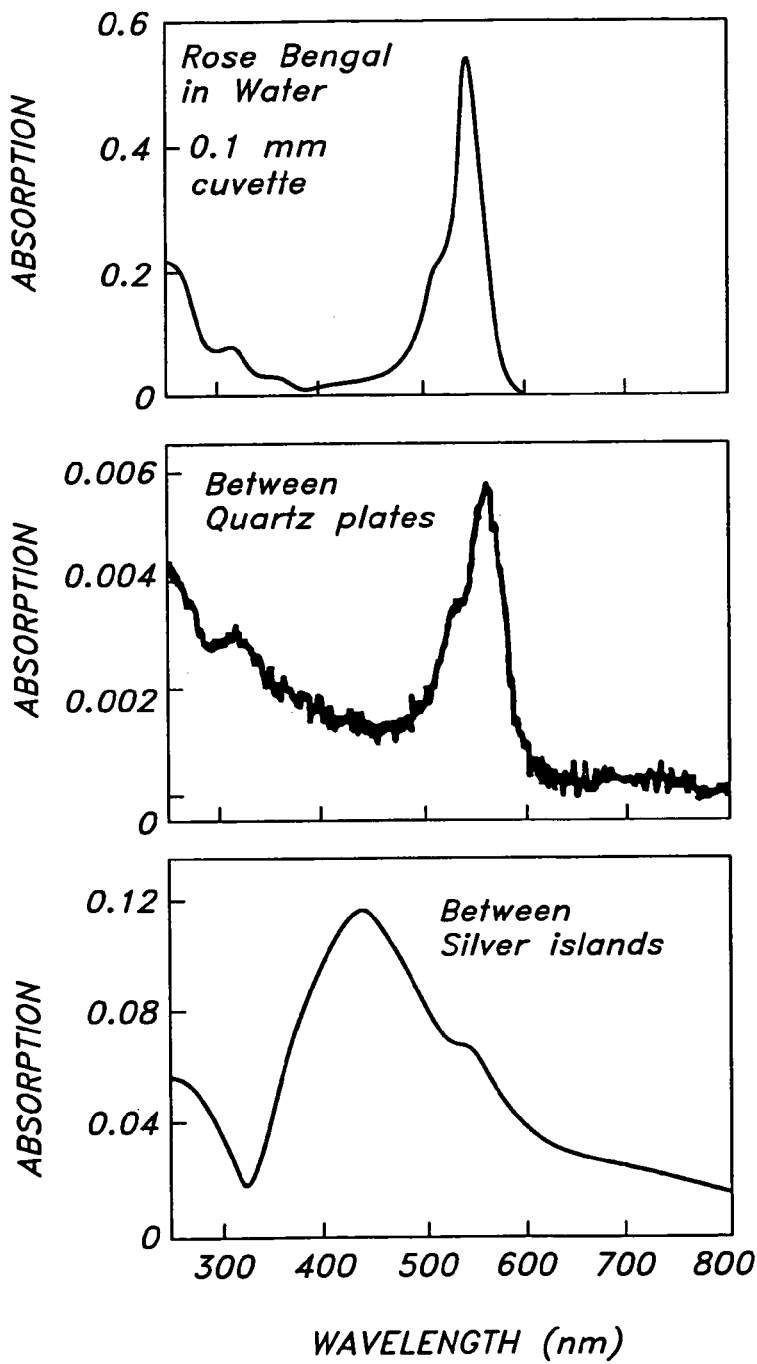
FIGS. 2A-C are absorption spectra of rose bengal in a cuvette, between quartz plates, and between quartz slides with silver islands respectively.

To determine the effects of silver islands on fluorescence, samples containing fluorophores were placed between two such silver island plates. From the absorption spectra of rose bengal, between two quartz plates, or two silver island coated plates (FIGS. 2A-2C). The distance between the plates is about 1 to 1.5 μm.

Example 2

Effects of Silver Island Films on Emission Spectra and Lifetimes

Figure 3A:
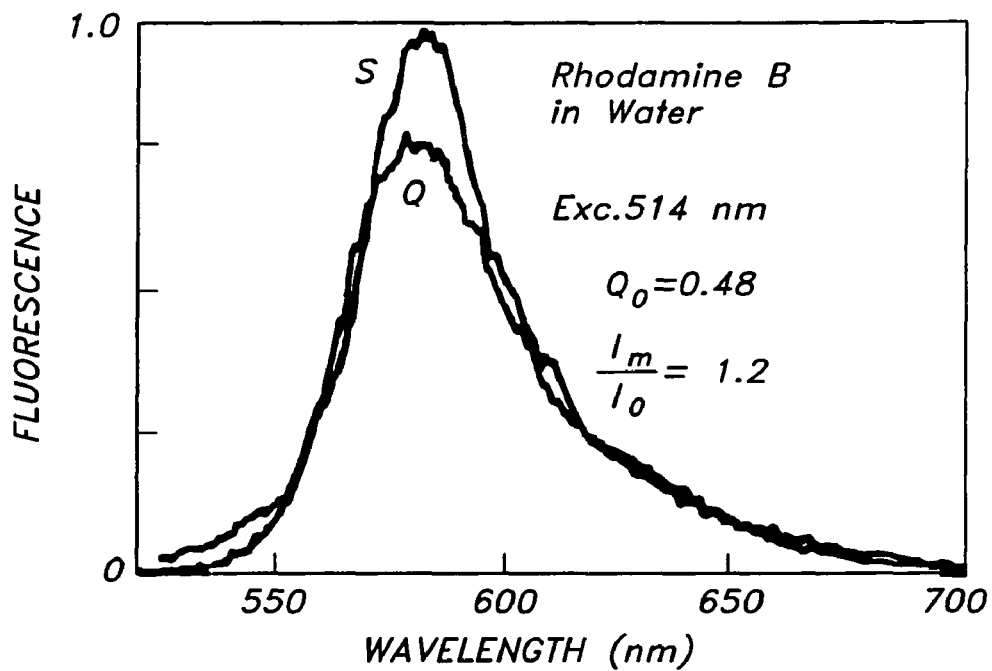
FIGS. 3A, 3B are emission spectra of rhodamine B and rose bengal between silver island films.

As an initial experiment, the emission spectra of rhodamine B (RhB) and rose bengal (RB) between uncoated quartz plates (Q) or silver island films (S) were examined. These two fluorophores were selected because of their similar absorption and emission spectra but different quantum yields of 0.48 and 0.02 for RhB and RB, respectively. In the case of RhB the intensities are similar in the absence and presence of these silver islands (FIG. 3A). There may be a small decrease in the RhB intensity due to the silver islands, which may be due to the quenching effects of metals at short distances.

Figure 3B:
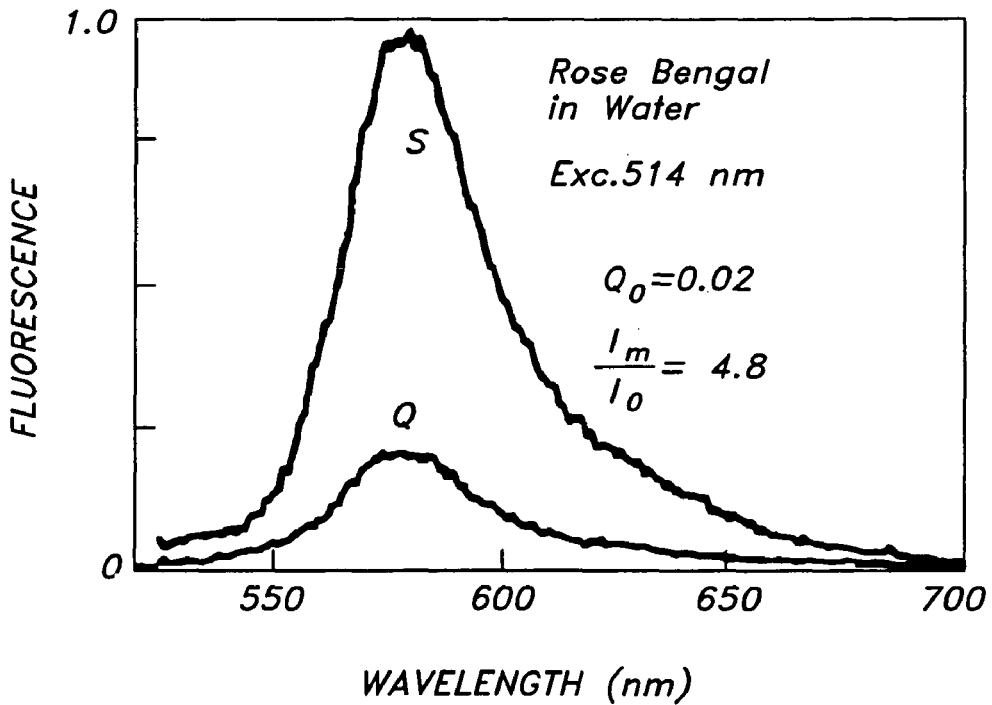

Contrasting results were obtained for rose bengal (FIG. 3B). In this case the intensity increased about 5-fold in the presence of silver islands. It is important to recognize that the increased intensity observed for RB represents an underestimation of the quantum yield of RB near the silver islands. This is because only a small fraction of the RB molecules are within the distance over which metallic surfaces can exert effects. The region of enhanced fluorescence extends about 200 Å to about 2000 Å into the solution. Hence only about 4% of the liquid volume between the plates is within the active volume. The low percentage of active volume suggests that the quantum yield of RB within 200 Å of the islands is increased 125-fold. This increase is larger than possible if the quantum yield of 0.02 is correct and reflects an increased incident field because of the metal particles. Nonetheless, the spectra for RB in FIG. 3 indicates a substantial increased in quantum yield for the molecule within 200 Å of the silver islands.

The effect of a concentrated electric field is not the dominant cause of the intensity increase for rose bengal in FIG. 3B. The emission occurs for RhB molecules both near to and distant from the silver islands. The field concentration effects could be masked by a dominant emission from the RhB molecules distant from the silver islands.

The effects of an increased radiative rate and concentrated electric field can be distinguished by lifetime measurements. An increase in the radiative rate will decrease the lifetime; whereas, an increased rate of excitation will not change the lifetime. The intensity decays of RhB and rose bengal in the absence and presence of silver islands were measured (FIGS. 4A-4C and FIGS. 5A-5C). In a standard cuvette the intensity decay of RhB was found to be a single exponential with a lifetime $\tau = 1.56$ ns (FIG. 4A). In the presence of silver islands the intensity decay becomes strongly heterogeneous (FIG. 4C).

The data could fit two decay times with the long lifetime of 1.81 ns being comparable to that found in a cuvette. Between silver islands, a short lifetime of 0.14 ns appeared which is attributed to RhB molecules in close proximity to the silver islands. The fractional steady state intensity of this short component is about 10%. Control measurements showed that this component was not due to scattered light. Measurements were also performed for RhB between quartz plates without silver islands. In this case the decay was also double exponential, but less heterogeneous than in the presence of islands. Nonetheless, it is clear that a short lifetime component appears for RhB between silver islands (FIG. 4B). Control measurements showed there was no significant intensity for the quartz slides alone without RhB. This result suggests that scattered light is not the origin of the short component seen for RhB between uncoated slides.

Figures 5A, 5B, 5C:
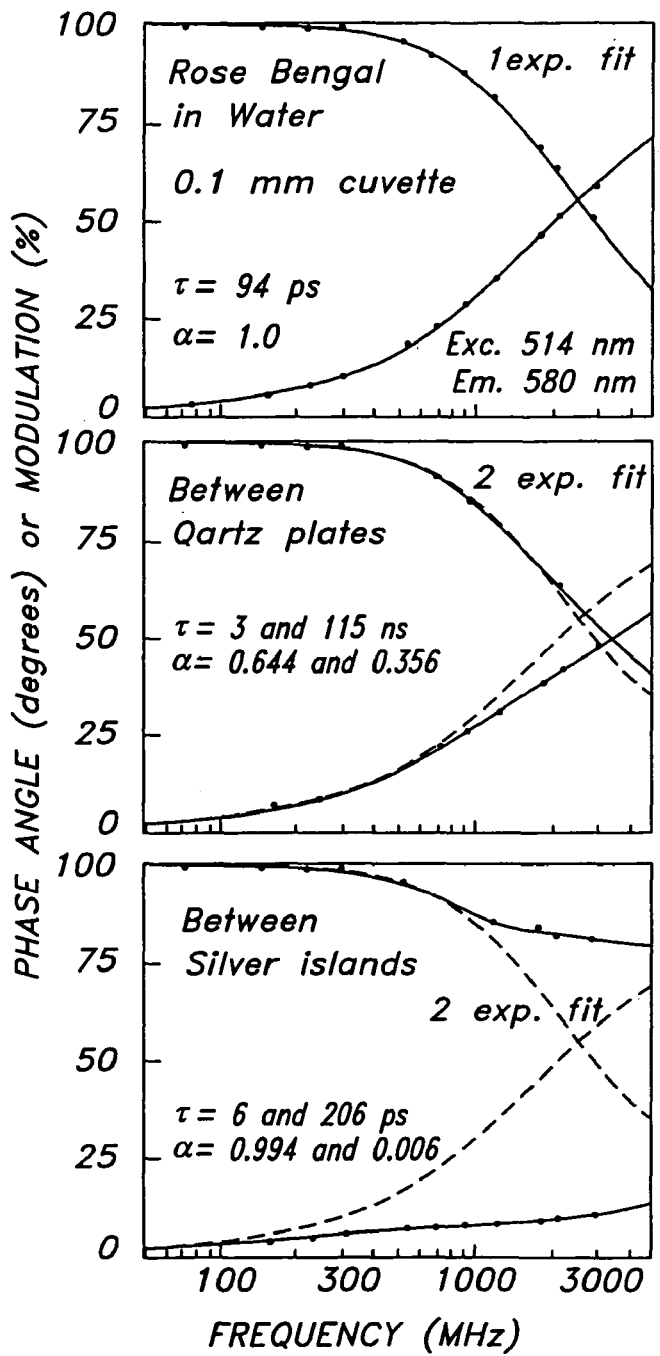
FIGS. 5A-5C are graphs showing frequency-domain intensity decays of rose bengal under various conditions.

Frequency-domain (FD) intensity decays for rose bengal are shown in FIGS. 5A-5C. In a cuvette the decay in a single exponential with τ=94 ps. The decay become slightly heterogeneous for rose bengal between uncoated quartz plates. However, the intensity decay of rose bengal changed dramatically when between silver islands. In this case the dominant lifetime became a 6 ps component, which corresponds to rose bengal molecules adjacent to the silver islands.

Figure 6A:
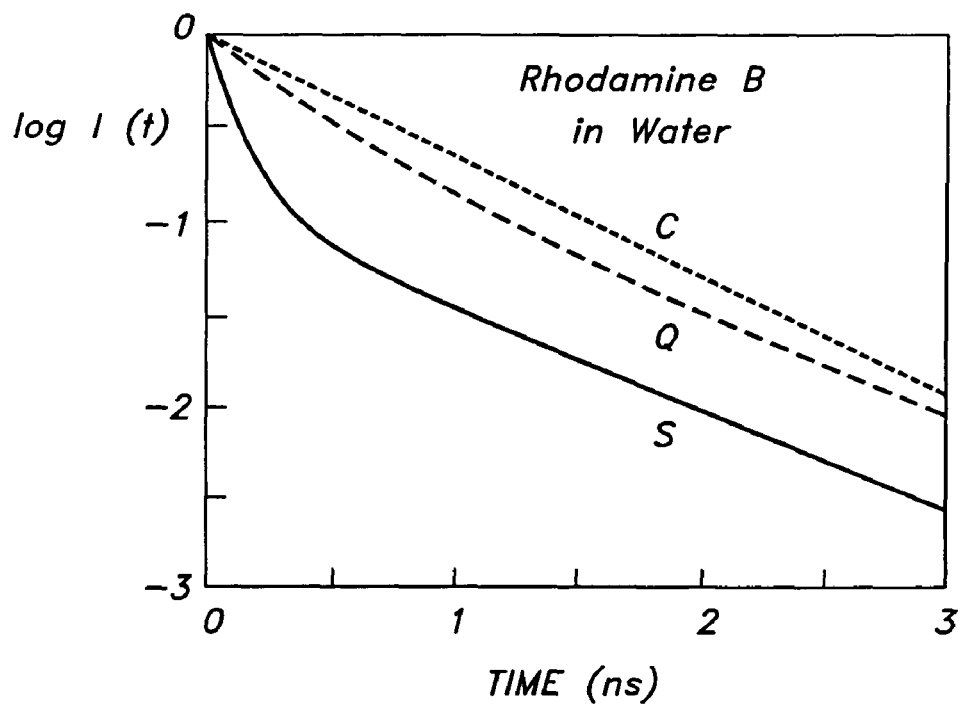
FIGS. 6A-6B are reconstructed time-domain intensity decays of rhodamine B and rose bengal.
Figure 6B:
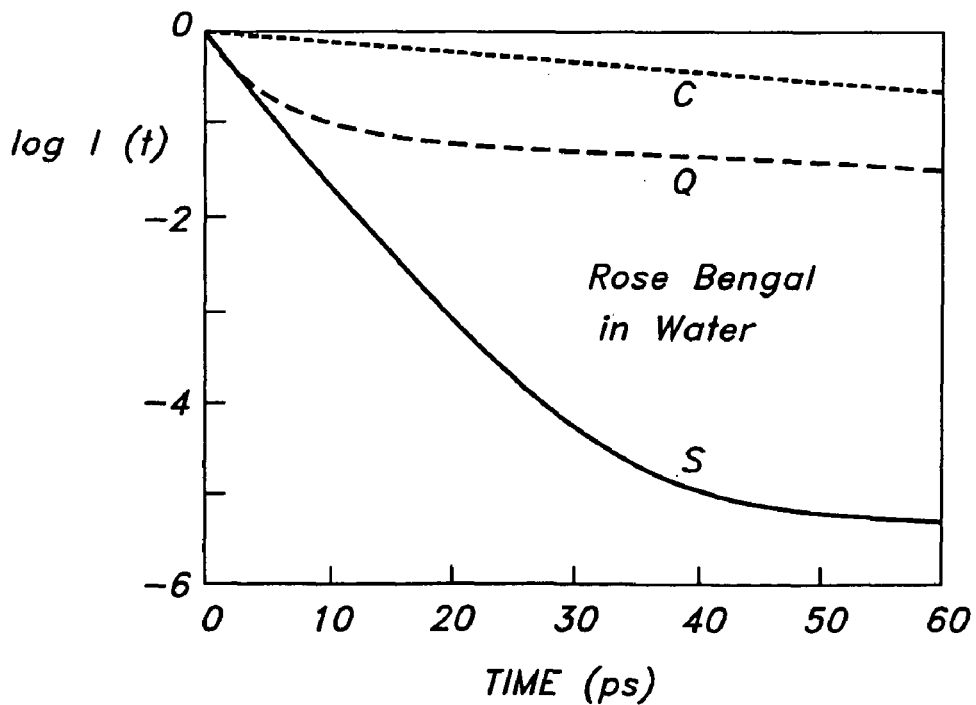

The effects of silver islands on the intensity decays of RhB and rose bengal can be seen in the time-resolved decays reconstructed from the frequency-domain data (FIGS. 6A and 6B). For both fluorophores the intensity decay shows long decay time components essentially identical to the values observed in cuvettes. Silver islands result in the appearance of short decay times. The larger contribution of the short decay times for rose bengal can be understood from its lower quantum yield in bulk solution. RhB has a higher quantum yield so that its emission is detected from molecules throughout the 1 μm thick sample. Rose bengal has a low quantum yield in solution so the observed emission is mostly due to rose bengal molecules near the silver islands. The results from RhB and rose bengal were consistent with expectations.

A number of additional fluorophores between uncoated quartz plates and between silver island films were examined to account for the contributions of artifacts. Emission spectra of four fluorophores (Erb, BF, $[Ru(bpy)_3]^{2+}$, and $[Ru(phen)_2 dppz]^{2+}$) are shown in FIGS. 7A-7D. In all cases the emission was more intense for the solutions between the silver islands. For example, $[Ru(bpy)_3]^{2+}$ and $[Ru(phen)_2 dppz]^{2+}$ have quantum yields near zero, respectively (Van Houten et al. (1975) *J. Am. Chem. Soc.* 97, 3843-3844; Harriman, A. (1977) *J. Chem. Soc., Chem. Commun.* 777-778; Nair et al. (1997) *Inorg. Chem.* 36, 962-965; Turro et al. (1995) *J. Am. Chem. Soc.* 117: 9026-9032). A larger enhancement was found for $[Ru(phen)_2 dppz]^{2+}$ than for $[Ru(bpy)_3]^{2+}$.

Figure 8:
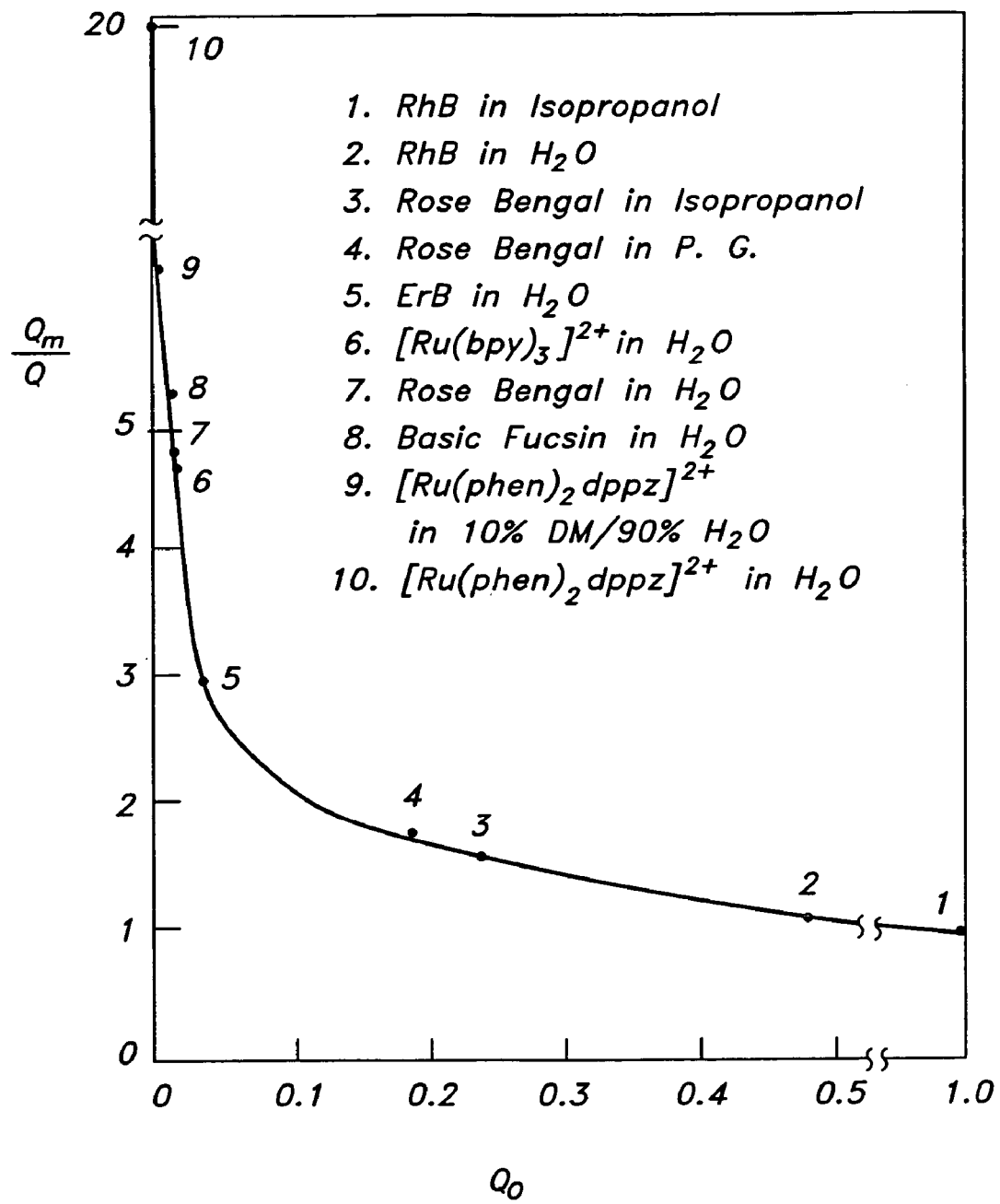
FIG. 8 is a graphical depiction of the enhancement of the emission of fluorophores having different quantum yields when placed between silver island films.
Figure 9:
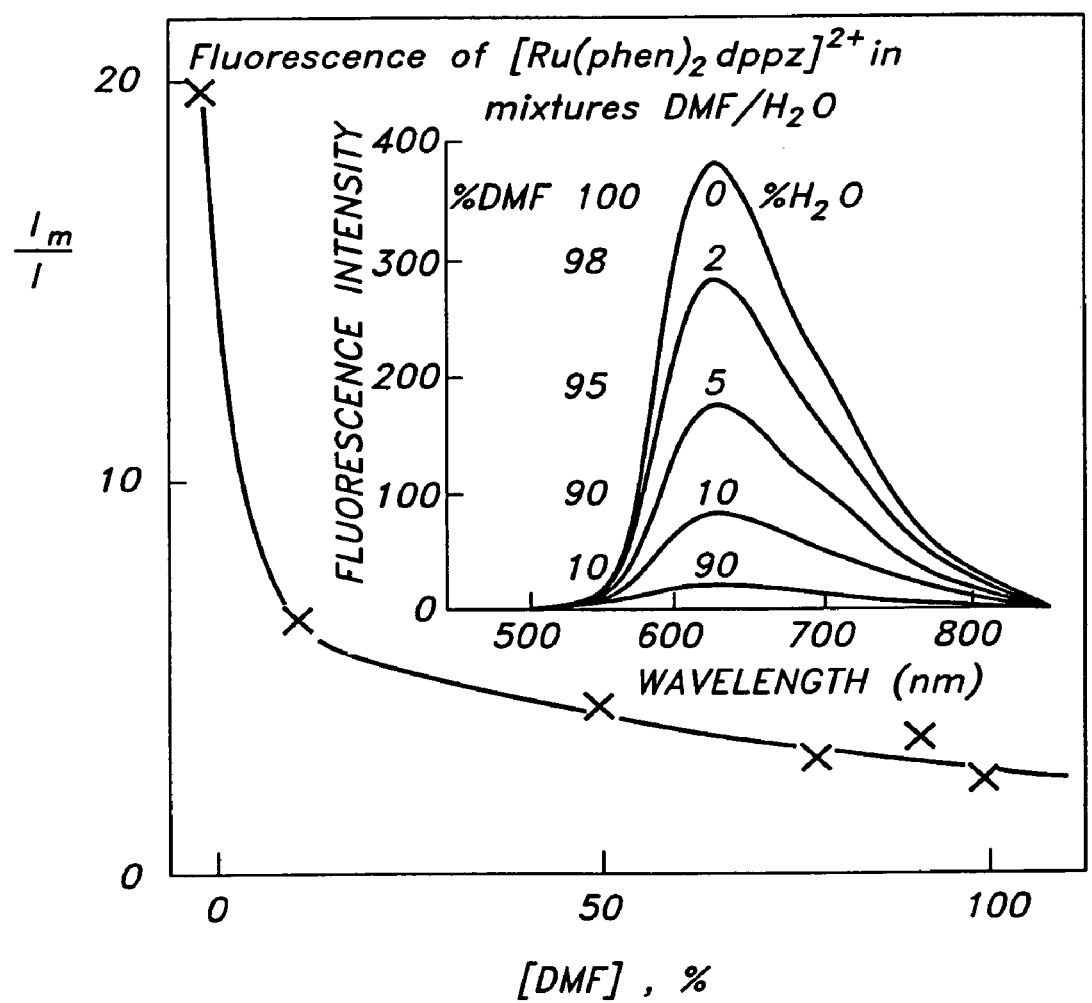
FIG. 9 is a graphical depiction of the fluorescence intensity of [Ru(phen)$_2$dppz]$^{2+}$ between silver island films (Is) compared to the fluorescence intensity between quartz plates (I$_Q$) in solutions of DMF and water. [Ru{phen}$_2$dppx]$^{2+}$ decreases in fluorescence intensity in the presence of water (inset).

The enhancements for 10 different fluorophore solutions are shown in FIG. 8. In all cases lower bulk-phase quantum yields result in larger enhancements for samples between silver island films. Additionally, $[Ru(phen)_2dppz]^{2+}$ in water-dimethylformamide (DMF) mixtures were examined (FIG. 9). This compound is quenched by water and the largest enhancements were observed for the most-quenched solution (FIG. 9). The results in FIGS. 7-9 provide strong support for the assertion that proximity of the fluorophore to the metal islands resulted in increased quantum yields. It is unlikely that these diverse fluorophores would all bind to the silver islands or display other unknown effect results which resulted in enhancements with increased monotonically with decreased quantum yields.

Example 3

Spectral Shifts in the Presence of Silver Islands

Figure 10A:
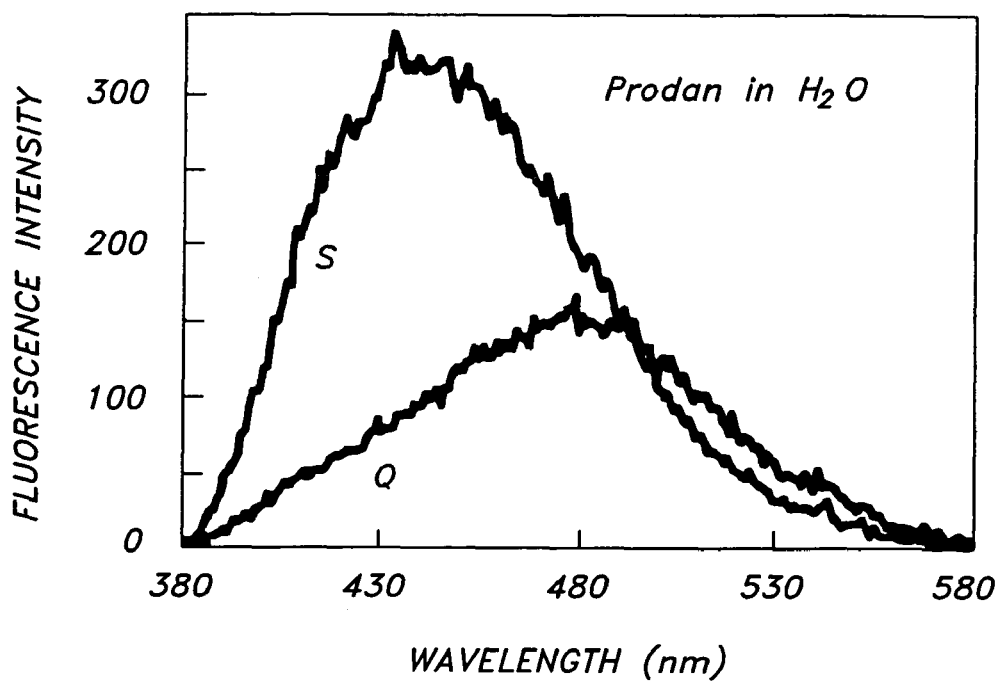
FIGS. 10A and 10B are emission spectra of solvent-sensitive fluorophores between silver island films (S) and between uncoated quartz plates (Q).
Figure 10B:
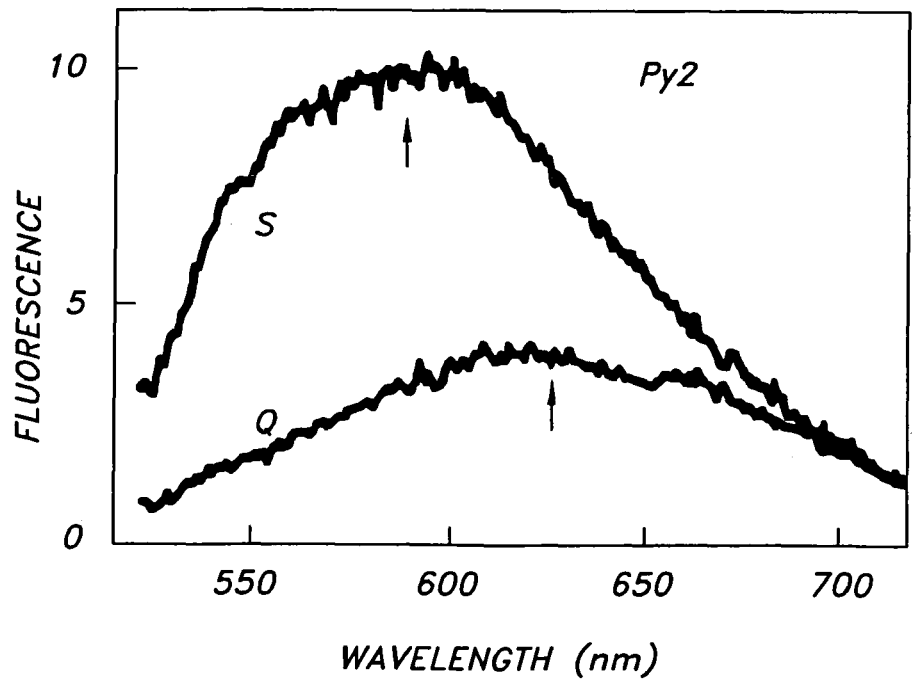

FIGS. 10A and 10B show the emission spectra of two solvent sensitive fluorophores between quartz plates (Q) and silver islands (S). In both cases blue shifts in the emission, which are consistent with a decreased lifetime of fluorophores near the islands were observed. Because fluorophores within 50 Å of the metal are likely to be quenched, it is unlikely that the blue shifts seen in FIG. 10A and FIG. 10B are due to fluorophores bound to the silver islands. Binding of fluorophores to the uncoated quartz surface is also unlikely because uncoated quartz is present for both emission spectra.

Example 4

Effects of Silver Islands on Intrinsic Protein Fluorescence

Figure 11A:
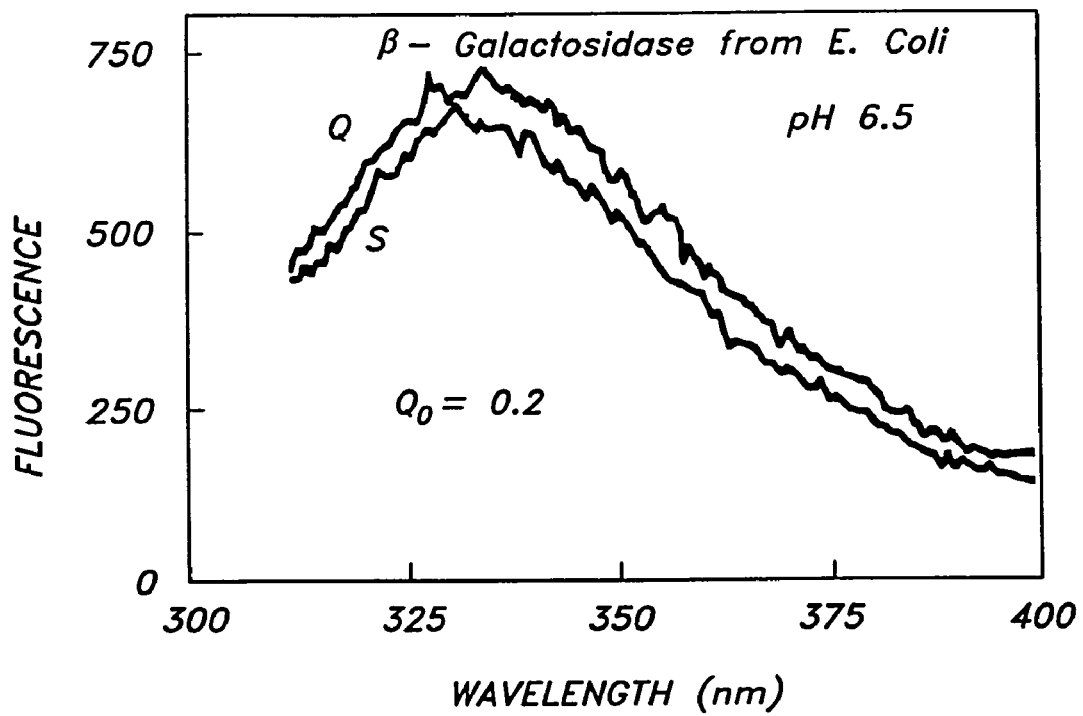
FIGS. 11A and 11B are emission spectra of β-galactosidase and human glyoxalase between silver island films (S) and between uncoated quartz plates (Q).
Figure 11B:
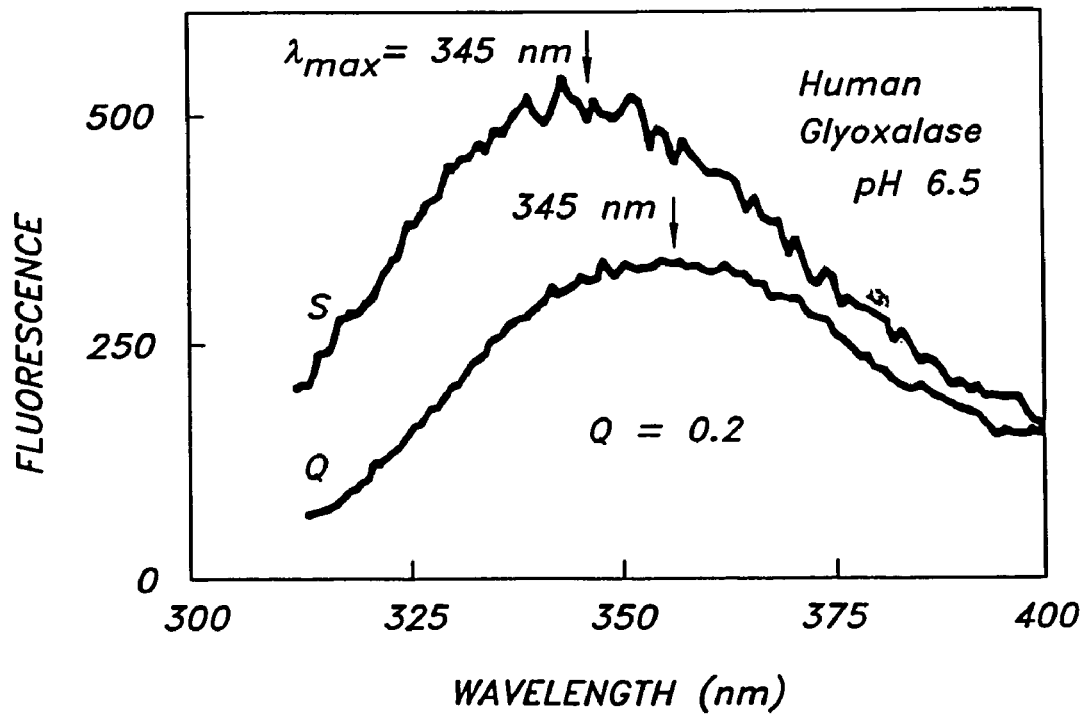

The protein *E. coli* β-galactosidase and human glycoxidase were obtained from commercial suppliers. The proteins were dissolved in 10 mM phosphate buffer, pH 6.5. The concentrations of β-galactosidase and human glyoxylase were 0.05 and 0.15 mg/ml, respectively. For studies of intrinsic protein fluorescence the excitation wavelength was 295 nm. The emission spectra of two proteins in the presence and absence of silver islands were examined (FIGS. 11A and 11B). The proteins β-galactosidase and human glyoxylase were selected for their modest and low quantum yields. β-galactosidase has a quantum yield approximately equal to that of N-acetyl-L-tryptophamide (NATA) (D'Auria et al. (2001) *J. Biochem.*, in press) which is reported to be 0.13 (Demchenko, A. P. (1981). Ultraviolet Spectroscopy of Proteins, Springer-Verlag, New York.). The quantum yield of human glyoxylase was found to be about 10-fold less, and thus near 0.013. For the higher quantum yield P-galactosidase there was no significant effect of the silver islands on the emission spectra. For the lower quantum yield human glyoxylase are observed both a blue shift and an increase in emission intensity. β-galactosidase is a tetrameric protein, 480,000 molecular weight, which contains 26 tryptophan residues in each 120,000 dalton subunit (Jacobson et al. (1994) *Nature* 369, 761-766). Human glyoxylase is a 66,000 dalton monomer which contains two tryptophan residues (D'Auria, S., unpublished results). The spectra changes in FIG. 11B are due to increased emission from a highly quenched tryptophan residue in glyoxyalase which is shielded from the solvent. The absence of a spectral shift or enhancement in β-galactosidase is understandable given its large number of tryptophan residues and it being unlikely that a significant fraction was highly quenched. Thus, silver islands can result in increased emission from quenched aromatic amino acid residues in proteins.

Example 5

Effects of Silver Islands on Nucleic Acid Bases and DNA

Figure 12A:
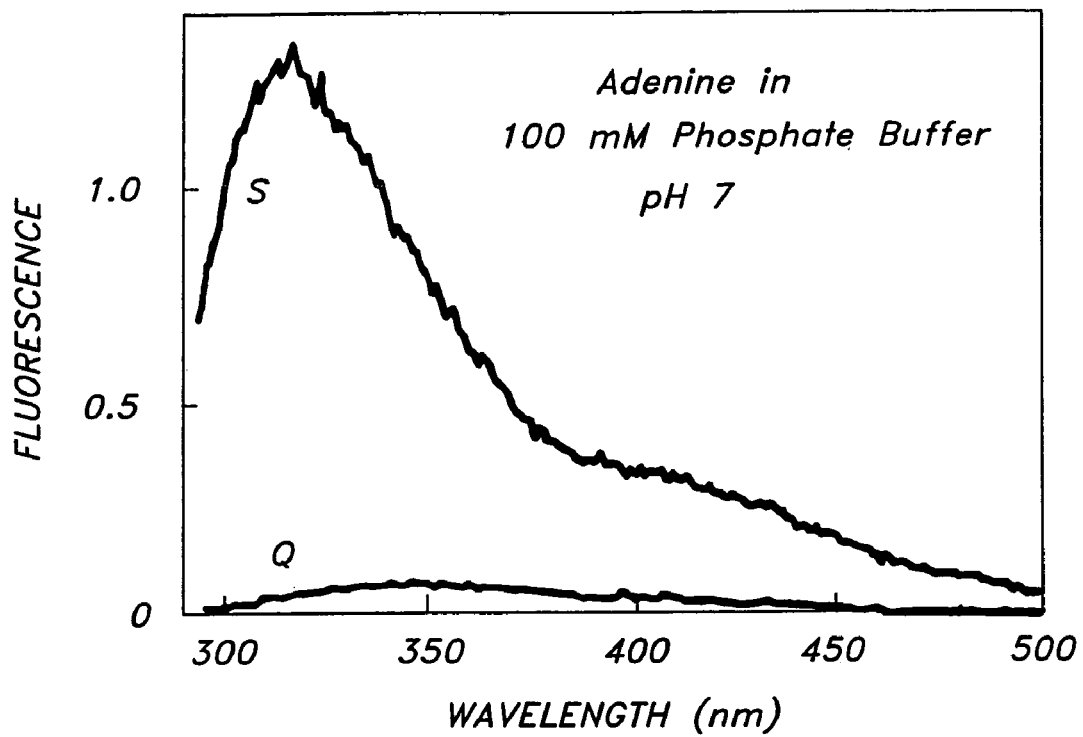
FIGS. 12A and 12B are emission spectra of nucleic acid bases between silver island films (S) and between uncoated quartz plates (Q).
Figure 12B:
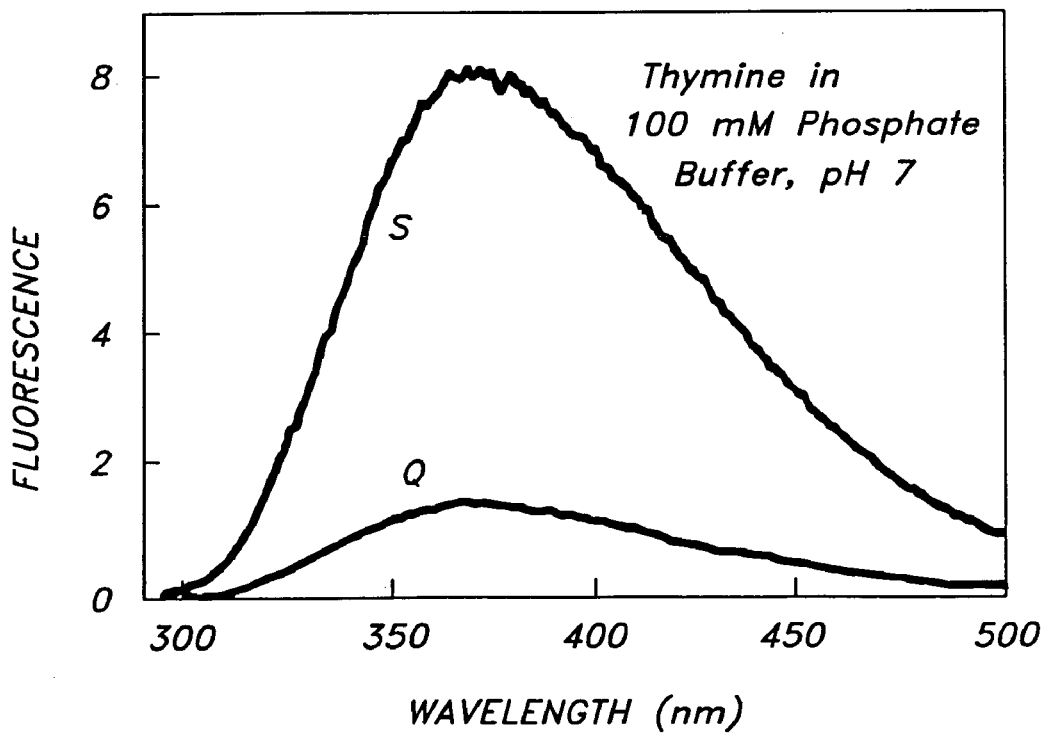
Figure 13A:
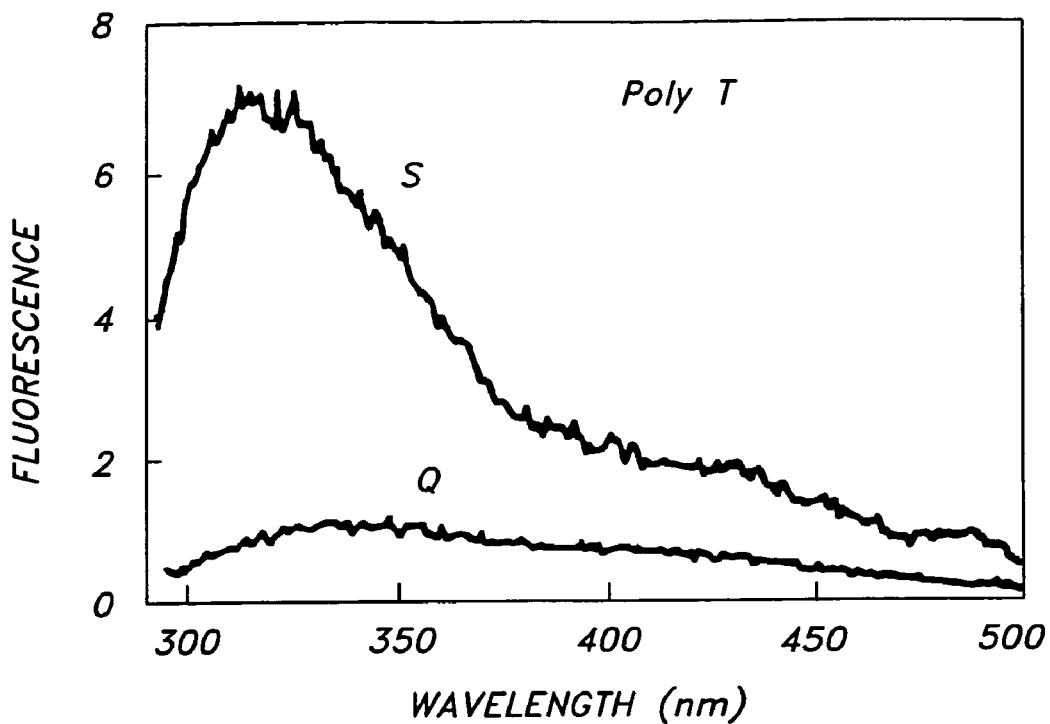
FIGS. 13A and 13B are emission spectra of single stranded nucleic acids between silver island films (S) and between uncoated quartz plates (Q).
Figure 13B:
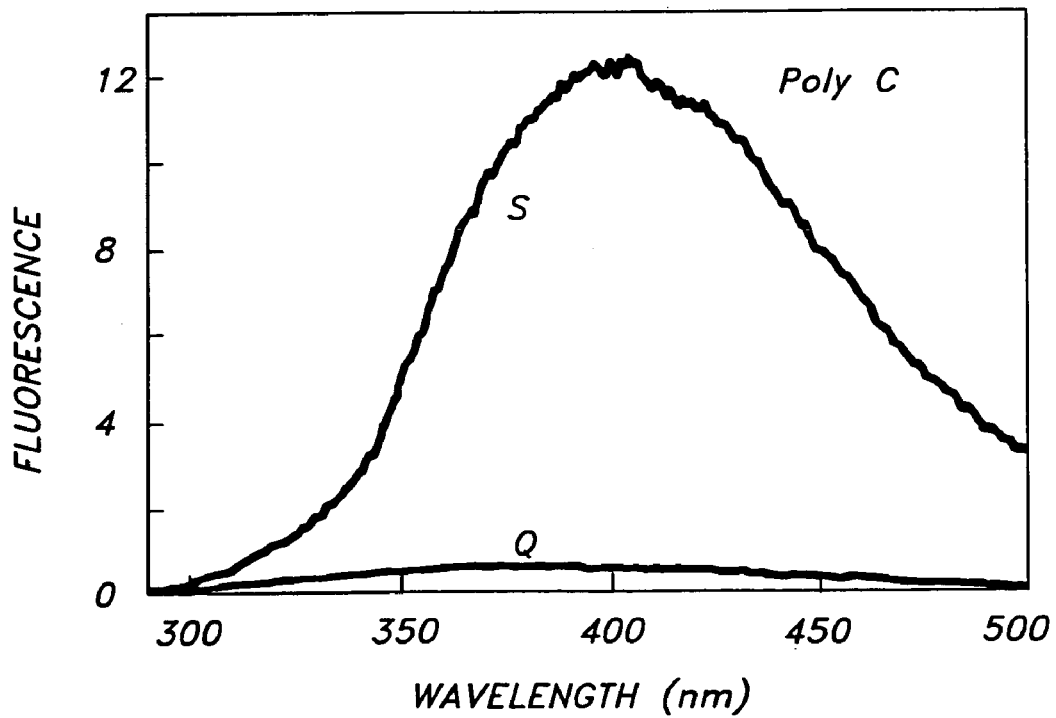

Adenine, thymine and calf thymus DNA were obtained from commercial suppliers. Poly T and poly C, each 15 bases long, were obtained from the Biopolymer Core facility at the University of Maryland, Baltimore School of Medicine. Emission spectra of the bases adenine and thymine are shown in FIGS. 12A and 12B, showing increased emission in the presence of the silver islands. Similar results were obtained for the single stranded nucleotides poly T and poly C (FIGS. 13A and 13B). The long wavelength emission maxima of poly C is in agreement with that reported previously (Plessow et al. (2000) *J. Phys. Chem. B* 104, 3695-3704).

Calf-thymus DNA was dissolved in 50 mM Tris, pH=7. The DNA concentration was 5 mM as base pairs. Emission spectra were measured on a SLM 8000 spectrofluorometer with 287 nm excitation. Frequency-domain lifetime measurements were obtained on a 10 GHz instrument (Laczko et al. (1990) *Rev. Sci. Instrum.* 61, 2331-2337; Lakowicz et al. (1994) *Biophys. J.* 46, 463-477). The excitation source was a cavity-dumped rhodamine 6G dye laser providing approximately 100 ps pulses which were frequency-doubled at 287 nm. Intensity decays were measured through a combination 344 nm interference filter plus a WG 335 long pass filter, which provided transmission from about 330 to 355 nm.

Emission spectra and lifetimes were measured with vertically polarized excitation and horizontally polarized emission. This optical configuration reduced scattered light of the excitation wavelength without significant distortion of the spectra or lifetimes. The frequency-domain data were fit to the multi-exponential model where the intensity decay is given by equation (1) above where $\alpha_i$ are amplitude factors associated with each decay time $\tau_i$. The sum of the $\alpha_i$ values are normalized to unity, $\Sigma \alpha_i = 1.0$.

Figure 14A:
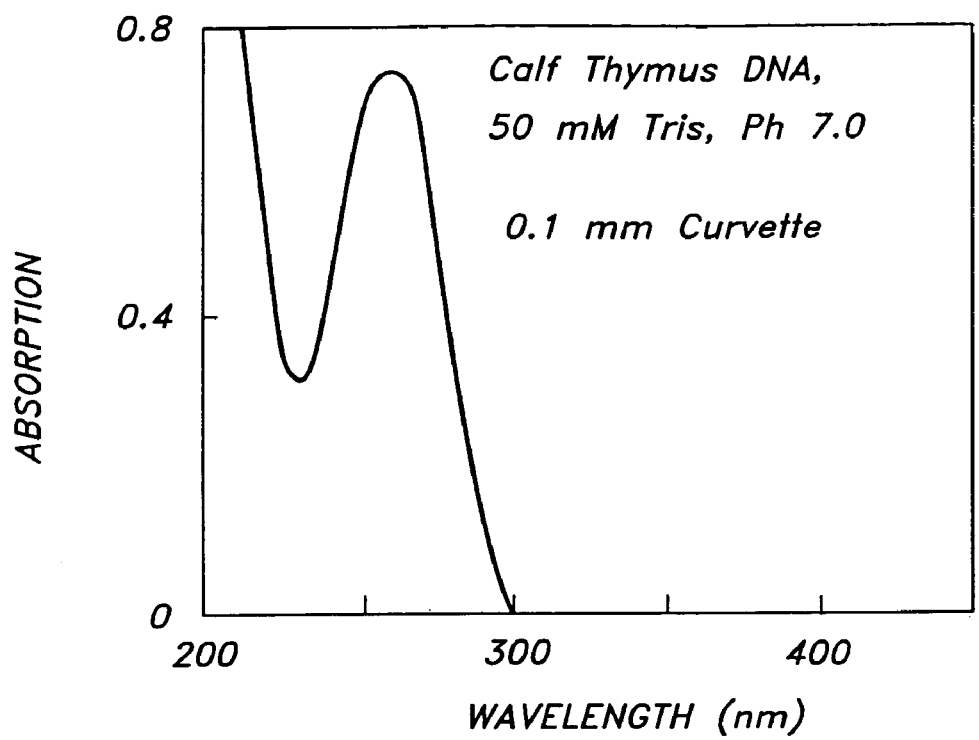
FIGS. 14A and 14B are absorption spectra of calf thymus DNA in a cuvette (14A) and between silver island films or uncoated quartz plates (14B).
Figure 14B:
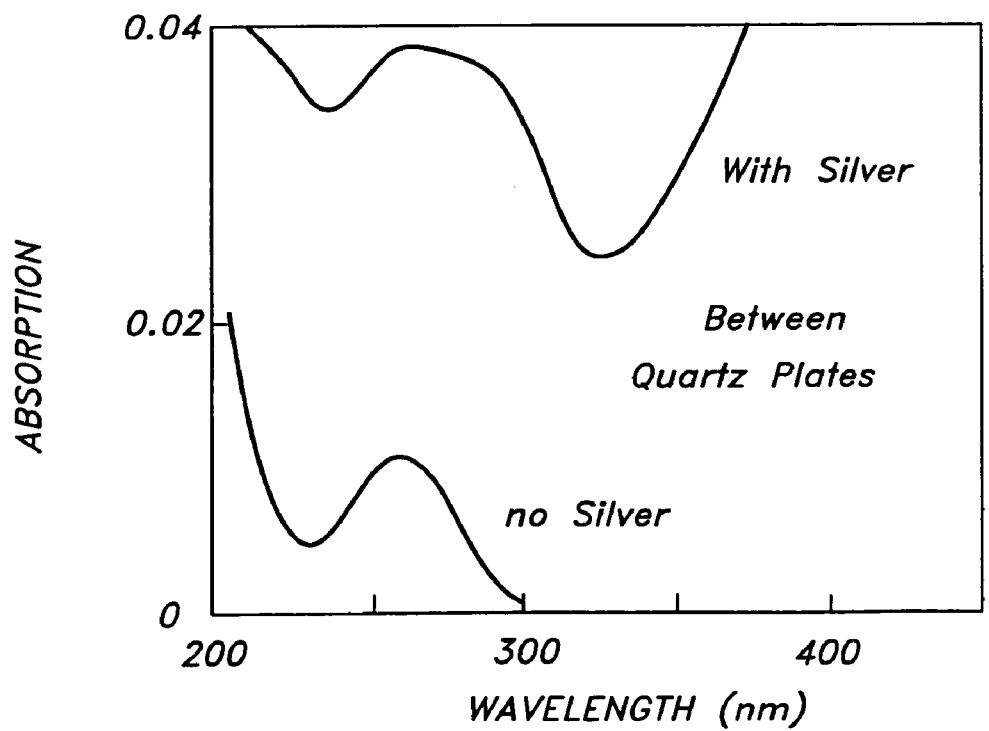

If the mass thickness is restricted to near 40 Å, one obtains particles on the surface with sub-wavelength dimensions, as can be seen from the characteristic surface plasmon absorption spectrum which are close to the small wavelength limit (FIG. 1B). The DNA samples were placed between two such silver islands plates with a separation near 1-1.5 μm. The absorption spectrum for DNA between the plates is approximately the sum of the DNA and silver island absorption (FIGS. 14A and 14B), which suggests that the islands did not significantly change the extinction coefficient of the DNA.

Figure 15A:
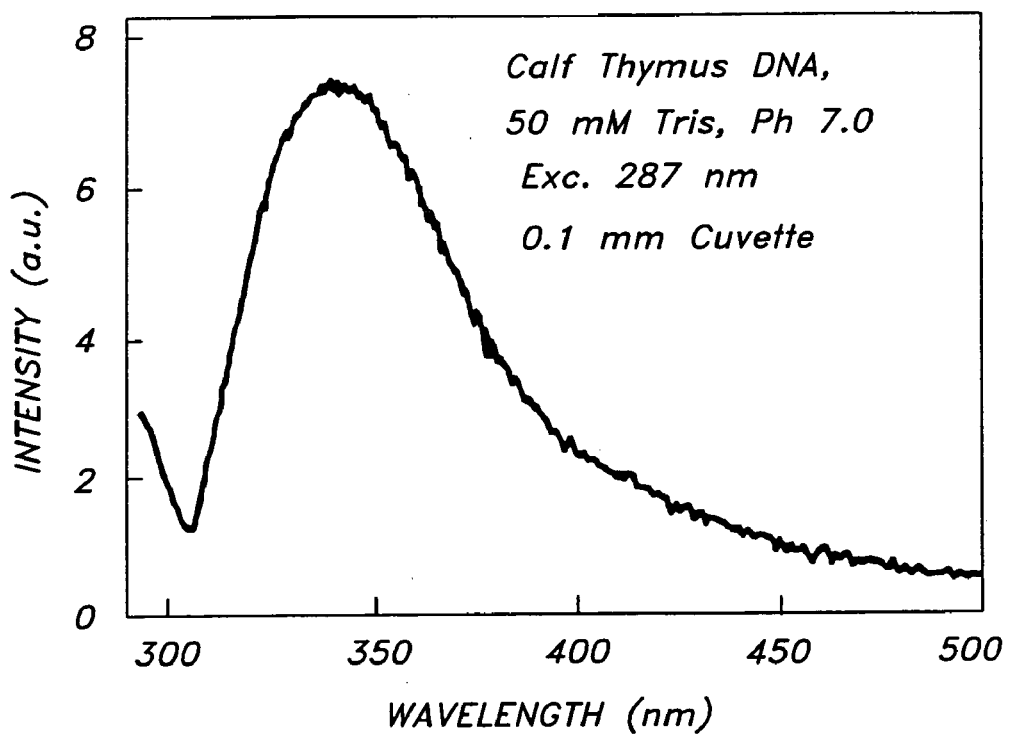
FIGS. 15A and 15B are the emission spectra of DNA in a cuvette (15A) and between silver island films or uncoated quartz plates (15B).
Figure 15B:
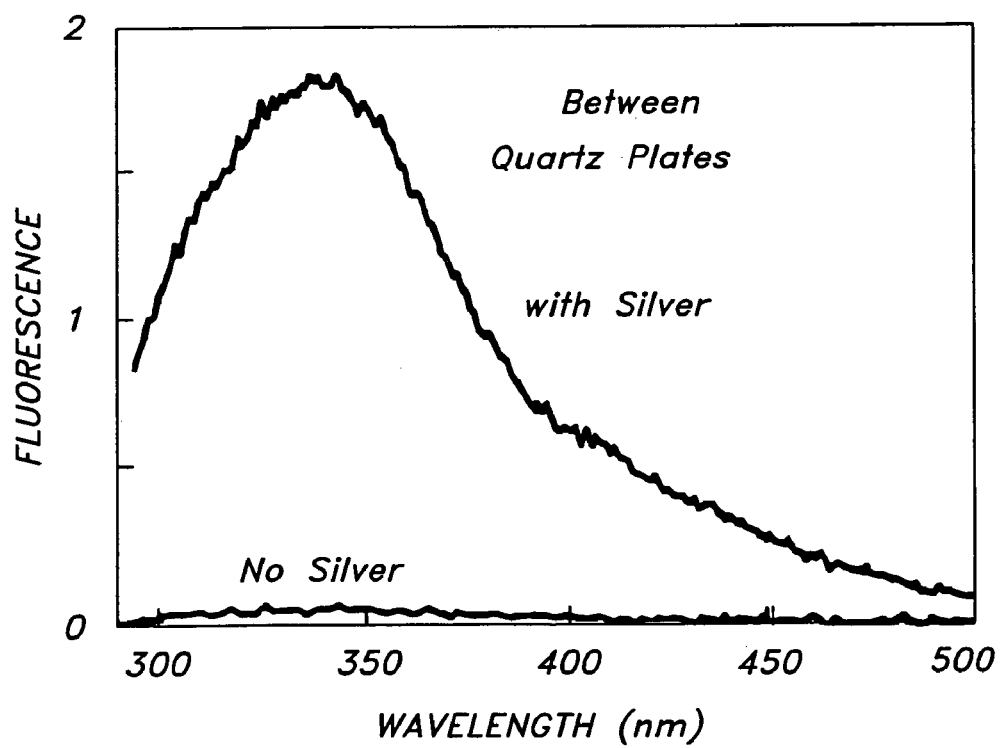

The emission spectrum of DNA was examined in a thin 0.1 mm cuvette and between the two island films (FIGS. 15A and 15B). Excitation at 287 nm probably resulted in partially selective excitation of the adenine and guanine residues (Wilson et al. (1980) *Photochem. & Photobiol.* 31, 323-327; Georghiou et al. (1996) *Biophys. J.* 70, 1909-1922). Surprisingly, the emission is about 80-fold more intense near the metal islands. It is important to note that this 80-fold increase is a considerable underestimate of the increase displayed by DNA near the particles. The region of enhancement is expected to extend about 200 Å to about 2000 Å into the solution. Taking into account the two island film surfaces, only about ½s of the DNA is near the silver. This suggests that the emission of DNA near the silver is enhanced 2000-fold. This is near the maximum enhancement predicted for a molecule at the optimal distance from an ellipsoid of appropriate size and shape. Amplified field effect can result in a maximum of 140-fold enhancement (Gersten et al. (1981) *J. Chem. Phys.* 75, 1139-1152) suggesting a minimum of a 15-fold increase in the quantum yield of the DNA near the island films. It is unlikely that the field enhancement is maximal. The actual increased quantum yield of DNA is between about 15-fold and less than about 2000-fold.

tial, which can be seen from the range of decay time from 60 ps to 4.56 ns. The individual lifetimes of DNA are uncertain because of its weak intrinsic fluorescence, but the mean lifetimes ($\bar{\tau}$) are reliable. Such a wide range of lifetimes are in agreement with other published reports (Ballini et al. (1983) *Biophys. Chem.* 18, 61-65; Georghiou et al. (1985) *Photochem. & Photobiol.* 41, 209-212; Plessow et al. (2000) *J. Phys. Chem. B* 104, 3695-3704). The important conclusion from these experiments is that the mean lifetime ($\bar{\tau}$) of DNA decreased under the same conditions which we observed on 80-fold increase in intensity (FIG. 15B). Such a decreased lifetime cannot be explained by a decrease in $k_{nr}$ or increased rate of excitation. However, the decreased lifetime can be explained by an increase in the radiative decay rate. Let $\Gamma_m$ represent the rate of the radiative decay due to presence of the metal particles. This new rate changes the quantum in the presence of metal (m) to $$Q_m = \frac{\Gamma + \Gamma_m}{\Gamma + \Gamma_m + k_{nr}} \quad (3)$$

which will be larger than in the presence of the metal. The lifetime in the presence of the metal ($\tau_m$) will be decreased to $$\tau_m = \frac{1}{\Gamma + \Gamma_m + k_{nr}} \quad (4)$$

The quantum yields and lifetimes in the absence of metals are given by the equations 1 and 2 with $\Gamma_m = 0.0$. Hence an increase in the radiative decay rate of DNA by the metal can explain both the increased intensity and decreased lifetime in the presence of the silver islands. There is no quantitation agreement between the 80-fold increase in intensity and the 3-fold decrease in lifetime. There are numerous possible reasons, including different spatial averaging across the sample by the intensity and lifetime measurements. Nonetheless, the intrinsic DNA lifetime decreased while the intensity increased, demonstrating an increase in the rate of radiative decay.

TABLE 1

Fluorescence intensity decay parameters of calf thymus DNA in 50 mM TRIS, pH 7.0, 20° C.

| CONDITIONS | $\bar{\tau}(\text{ps})^{a)}$ | $\alpha_1$ | $\tau_1$ (ps) | $\alpha_2$ | $\tau_2$ (ns) | $\alpha_3$ | $\tau_3$ (ns) | $\chi_R^{2b)}$ |
|---|---|---|---|---|---|---|---|---|
| 0.1 mm cuvette | 60 | 0.974 | 12 | 0.021 | 1.17 | 0.005 | 4.56 | 2.7 |
| on silver islands | 19 | 0.989 | 5 | 0.007 | 0.59 | 0.004 | 2.38 | 3.2 |

$^{a)}\bar{\tau} = \Sigma_i \alpha_i \tau_i$
$^{b)}\chi_R^2$ is the goodness-of-fit parameter calculated with estimated uncertainties in the phase angle and modulation values of 0.3° and 0.007, respectively.

Figure 16A:
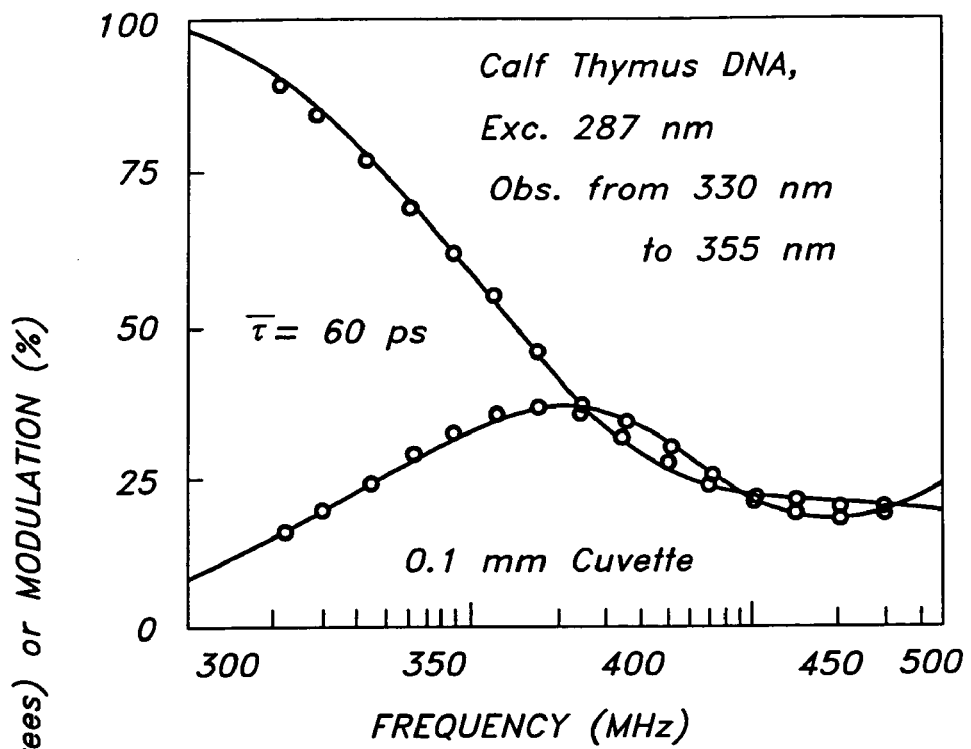
FIGS. 16A and 16B are frequency-domain intensity decays of calf thymus DNA in a cuvette (16A) and between silver island films (16B).
Figure 16B:
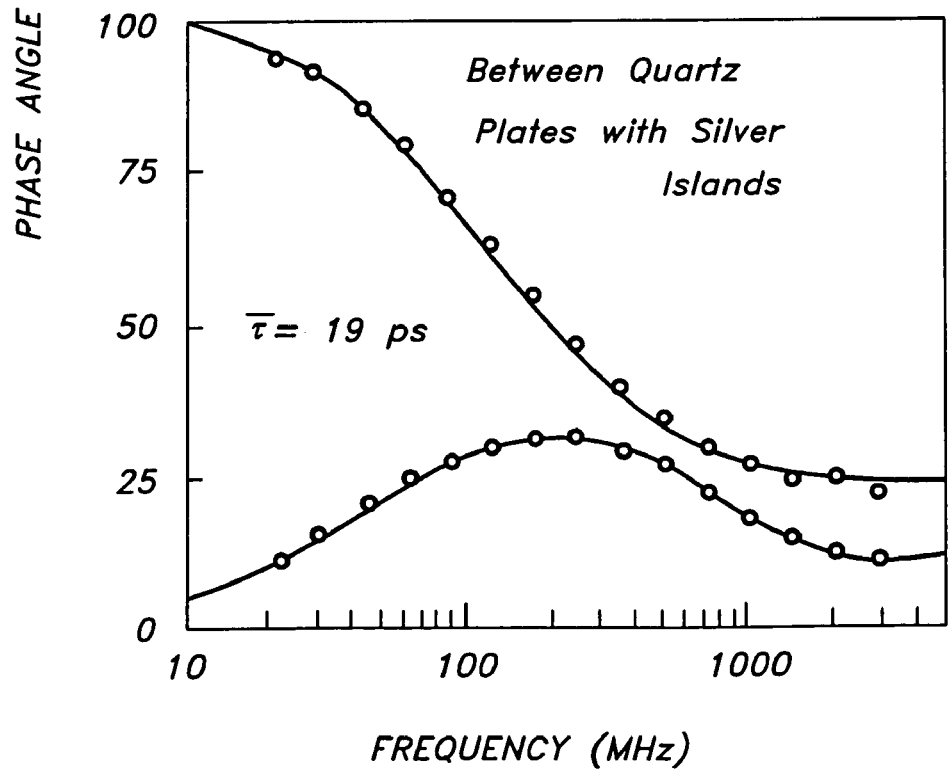
Figure 17:
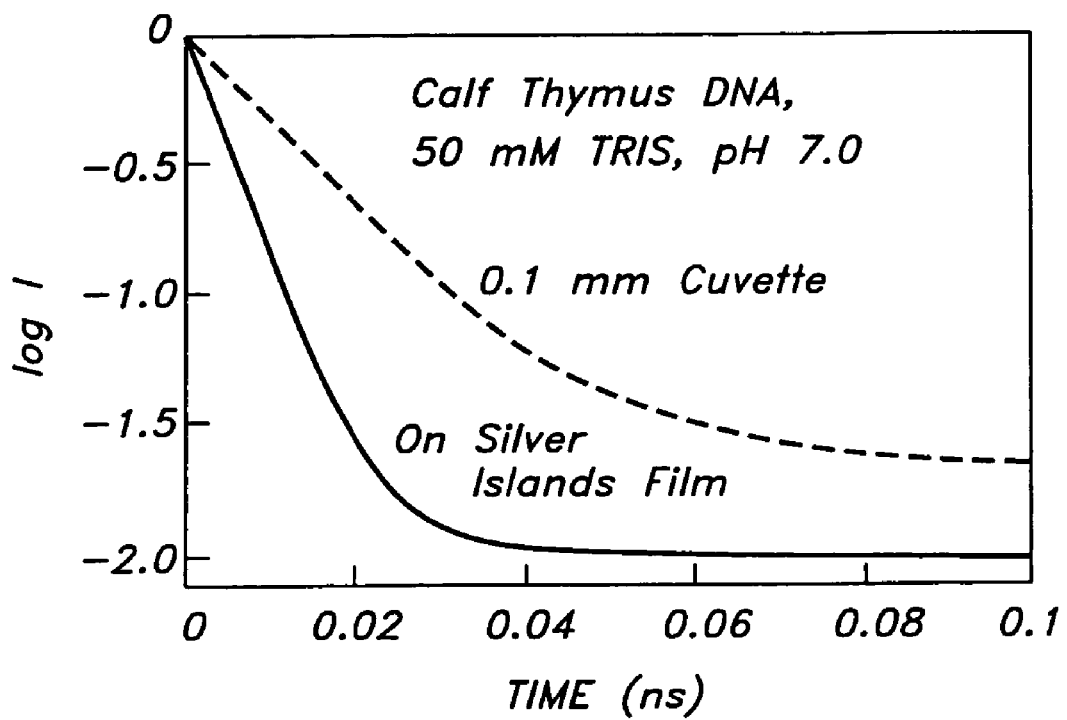
FIG. 17 is time dependent intensity decays of calf thymus DNA between silver island films and in a cuvette.

One explanation of the increased intensity seen in FIG. 15B could be a decrease in the non-radiative decay rate $k_{nr}$, which would result in a longer lifetime. Another reason for the increased emission could be an amplified incident light field. This effect would result in increased intensity, but is the lifetime would be unchanged. Frequency-domain intensity decays are shown in FIGS. 16A and 16B. These measurements were used to reconstruct the more intuitive time-domain decays (FIG. 17). The decays are multi-exponential in the absence or presence of metal islands (Table 1). The intensity decays were strongly heterogeneous or multi-exponen- Example 6

Effects of Silver Islands on Resonance Energy Transfer

Figure 18:
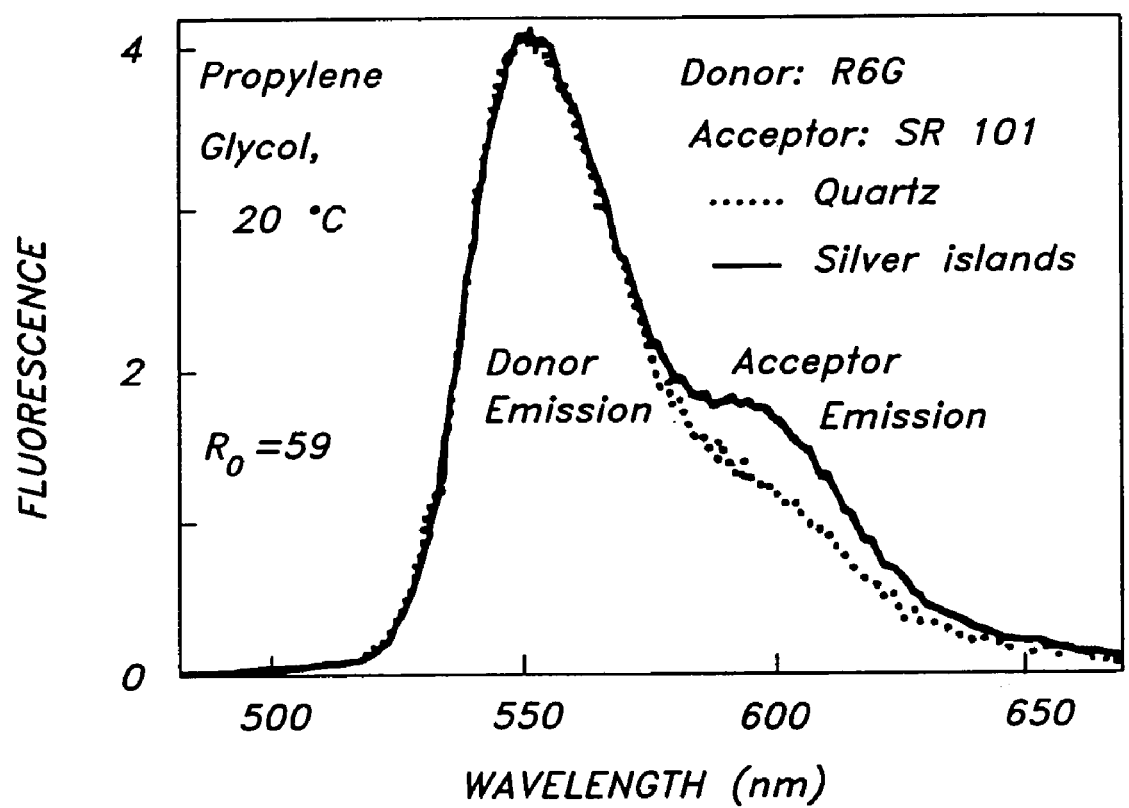
FIG. 18 is emission spectra of R6G as donor and SR101 as acceptor between uncoated quartz plates and between silver island films.

Resonance energy transfer (RET) is widely used in biochemical and biomedical research (Morrison et al. (1993) *Biochemistry* 32, 3095-3104; Ju et al. (1996). *Nat. Med,* 292, 246-249). RET occurs whenever fluorophores with suitable spectral properties come within the Förster distance $R_0$. Förster distances range from 20-40 Å, and are rarely larger than 50 Å. The effects of silver island films on RET between rhodamine 6G (R6G) and sulforhodamine 101 (SR101) when dissolved in homogeneous solution were examined. Emission spectra of this mixture are shown in FIG. 18, normalized to the donor emission. Silver islands result in an increase in the acceptor emission near 590 μm. While this increase may appear modest, it is substantial for a mixture of fluorophores in which the acceptors are present at a concentration of 0.2 mM resulting in significant direct excitation of the acceptor.

Figure 19:
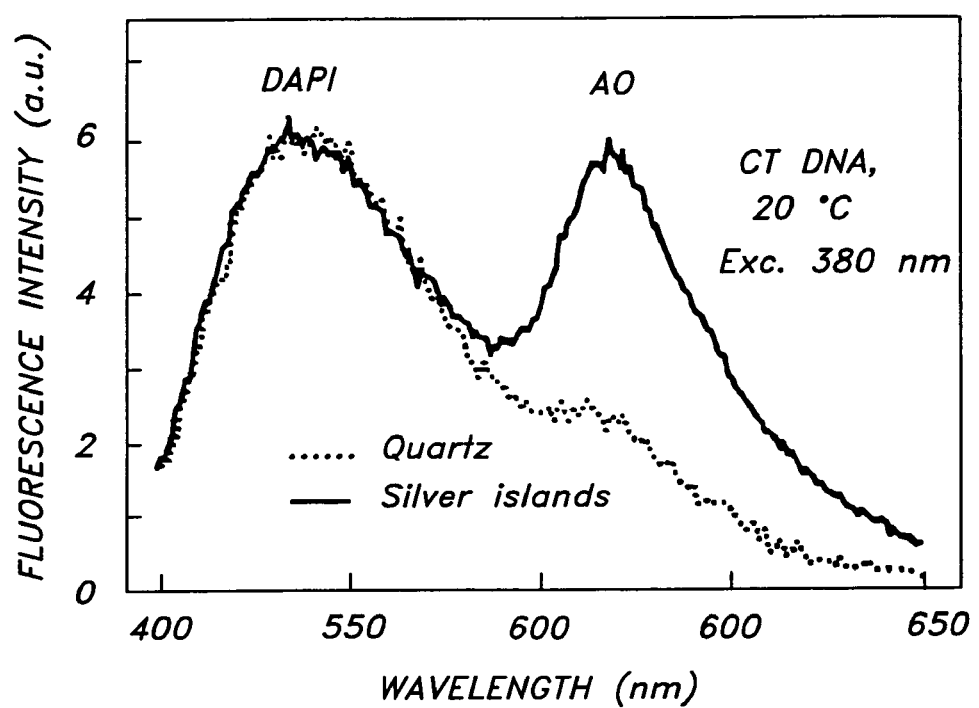
FIG. 19 is emission spectra of DNA labeled with DAPI and acridine orange between silver island films and between uncoated quartz plates.

Additionally, RET of DAPI to acridine orange (AO) when bound to double helical calf thymus DNA was examined (FIG. 19). In this case the bulk concentration of the donor and acceptor are lower because they are held in close proximity by the DNA. There is a dramatic increase in the acceptor emission near 520 nm which we believe is due to a metal-enhanced increase in the extent of energy transfer.

Calf thymus DNA was obtained from commercial suppliers and dissolved in 50 mM tris buffer, pH 7 to a concentration of 2 mM in base pairs using 13,300 $M^{-1}$ $cm^{-1}$ per base pair. DAPI and propidium iodide (PI) were obtained commercially. For the energy transfer measurements the DAPI and PI concentrations were $1.5 \times 10^{-5}$ M and $1.5 \times 10^{-4}$ M, respectively. These concentrations result in 133 base pairs per DAPI molecule and 13 base pairs per PI molecule.

Emission spectra were obtained using a SLM 8000 spectrofluorometer using 360 nm excitation. Intensity decays were measured in the frequency-domain using instrumentation described previously (Laczko et al. (1990) *Rev. Sci. Instrum.* 61, 2331-2337; Lakowicz et al. (1994) *Biophys. J* 46, 463-477). The excitation wavelength of 360 nm was obtained from the frequency-doubled output of a 3.80 MHz cavity dumped Pyridine 2 dye laser with a 10 ps or less pulse width.

For the frequency-domain measurements the emission was observed through a 460 nm interference filter. For steady state and frequency-domain measurements the excitation was vertically polarized and the emission observed through a horizontally oriented polarizer to minimize scattered light. The FD intensity decay were analyzed in terms of the multi-exponential model using equation (1) above where $\tau_i$ are the lifetimes with amplitudes $\alpha_i$ and $\Sigma\alpha_i = 1.0$. Fitting to the multi-exponential model was performed as described previously (Lakowicz et al. (1994) *Biophys. J* 46, 463-477). The contribution of each component to the steady state intensity is given by equation (2) above.

The mean decay time is given by $$\bar{\tau} = \sum_i f_i \tau_i \quad (5)$$

The amplitude-weighted lifetime is given by $$\langle \tau \rangle = \sum_i \alpha_i \tau_i \quad (6)$$

The base pair length 3.4 Å and $r_{min}=12$ Å were fixed parameters.

Silver particles were obtained by chemical reduction of silver onto quartz slides as above. If the mass thickness of the deposition silver is kept near 40 Å the silver particles have sub-wavelengths dimensions and display the characteristics of surface plasmon absorption (FIG. 1). From studies of the absorption spectra of dyes between two such silver island films the sample thickness was found to be near 1 to 1.5 μm.

Figure 20:
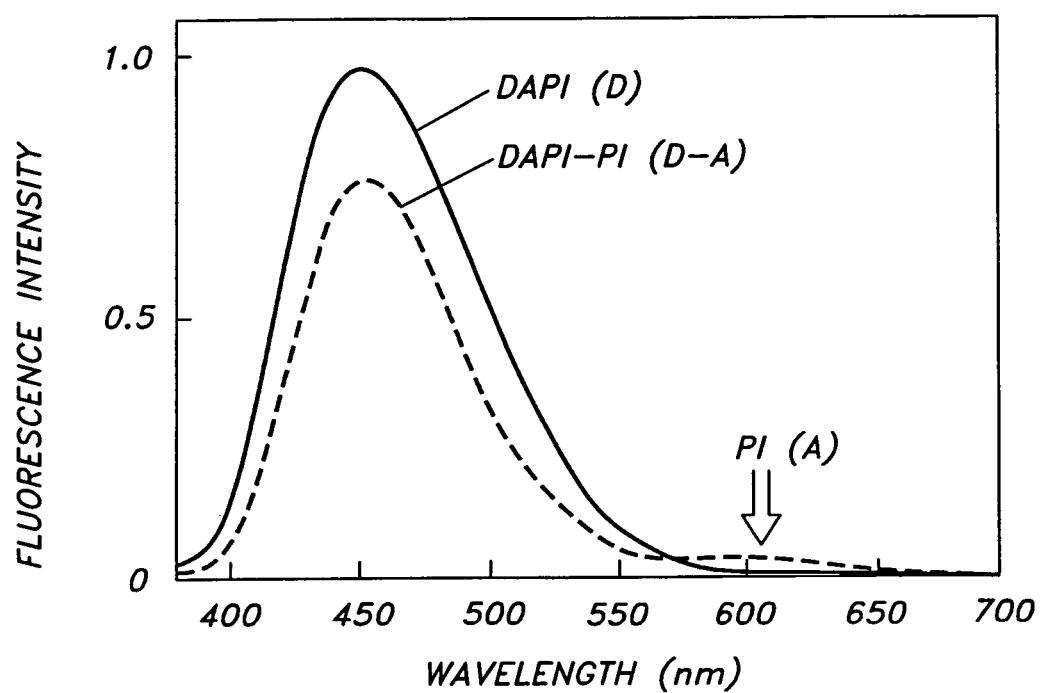
FIG. 20 is emission spectra of DNA labeled with DAPI alone; with propidium iodide (PI) alone; or with DAPI and PI between uncoated quartz plates.

To examine the effect of silver islands on resonance energy transfer double helical calf thymus DNA which was labeled with DAPI as the donor and/or PI as the acceptor was used. Emission spectra of DAPI-DNA and DNA labeled with both DAPI and PI in a cuvette are shown in FIG. 20. The extent of energy transfer is about 20%, as can be seen from the decrease in the DAPI donor intensity near 460 nm. The PI acceptor makes only a small contribution to the emission seen at 610 nm. The extent of energy transfer near 20% is consistent with the $R_0$ value of 35.7 Å for this D-A pair (Murata et al. (2000) *Biopolymers (Biospectrosc)* 57, 306-315). Based on the extent of acceptor labeling of one per 13 base pairs, and 3.4 Å per base pair in the DNA helix, the acceptor molecules are on average 45 Å apart.

Figure 21:
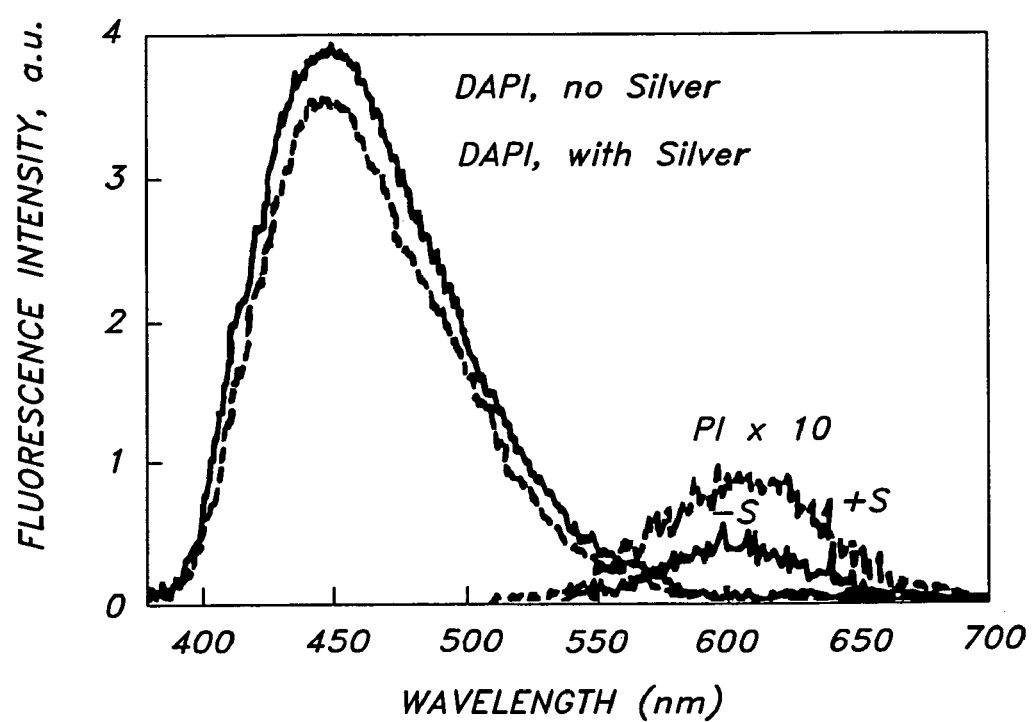
FIG. 21 is emission spectra of DAPI-labeled DNA and PI-labeled DNA between silver island films and between uncoated quartz plates.

Next, the effects of the silver island films on DNA labeled with only the DAPI donor or only the PI acceptor were examined (FIG. 21). In the case of DAPI-DNA the intensity is essentially unchanged when placed between quartz plates or between silver island film. In the case of PI-DNA there is an approximate 2-fold increase in the PI intensity. The larger effect of the silver island film on PI-DNA is consistent with its lower quantum yield near 0.15 as compared to 0.53 for DAPI-DNA (Murata et al. (2000) *Biopolymers (Biospectrosc.)* 57, 306-315).

Figure 22:
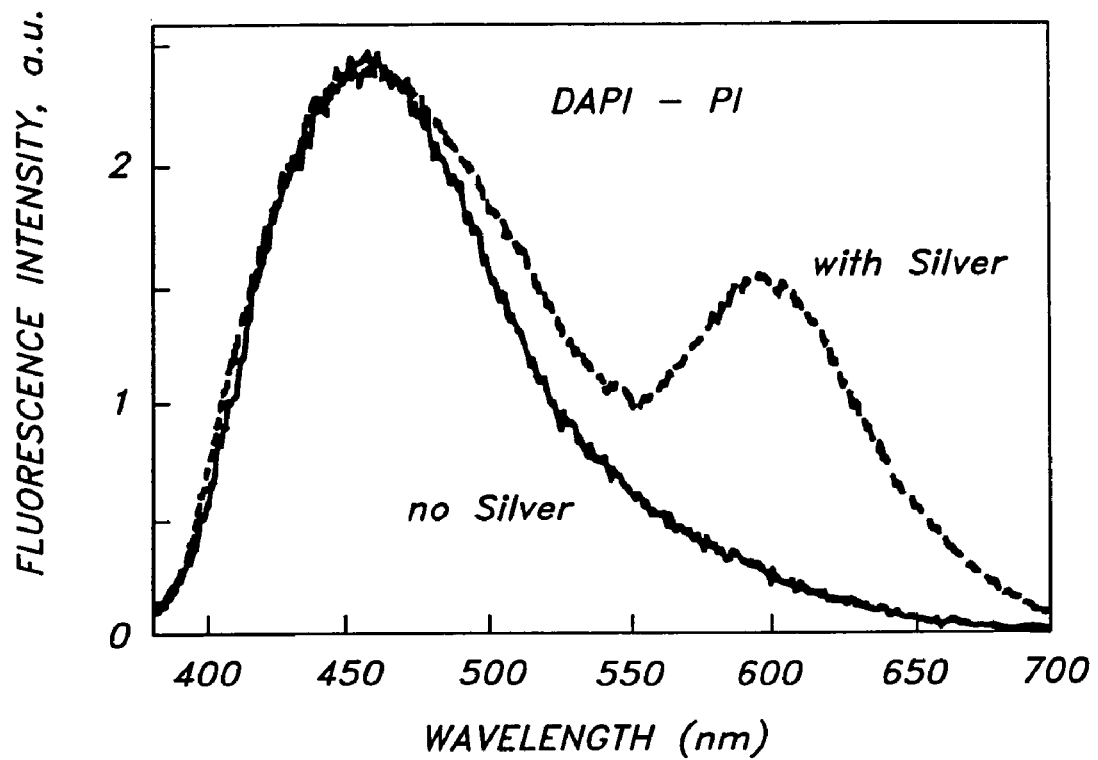
FIG. 22 is emission spectra of DNA labeled with both DAPI and PI between silver island films and between uncoated quartz plates.

The emission spectra of donor and acceptor-labeled DNA are shown in FIG. 22. A remarkable increase in the PI acceptor emission was found for the DNA sample between the two silver island films as compared to between two unsilvered quartz plates. The silver island film had only a modest effect on acceptor-only DNA (PI-DNA). These results show an increase in the efficiency of RET from DAPI to PI due to proximity to the silver islands.

Figure 23A:
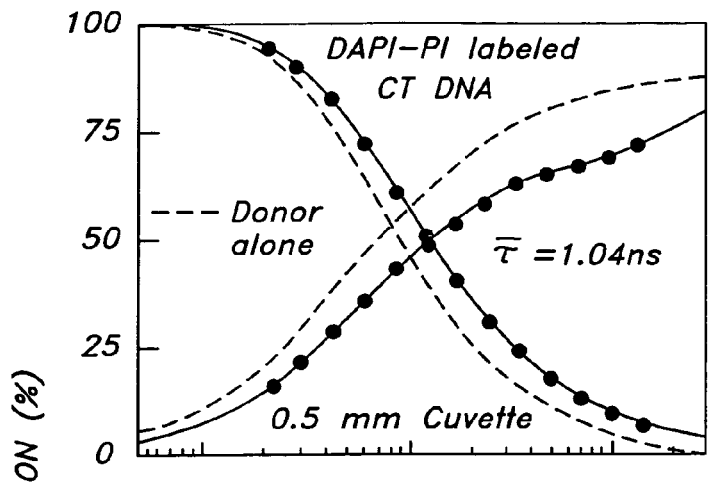
FIGS. 23A-23C are frequency-domain intensity decays of the DAPI donor decay for calf thymus DNA labeled with both DAPI and PI in a cuvette (23A), between uncoated quartz plates (23B), and between silver islands (23C). The frequency-domain intensity decay of DAPI alone is also shown.
Figure 23B:
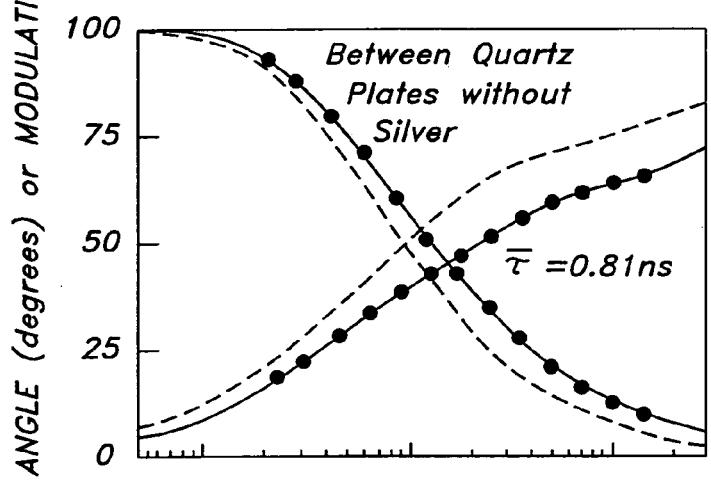
Figure 23C:
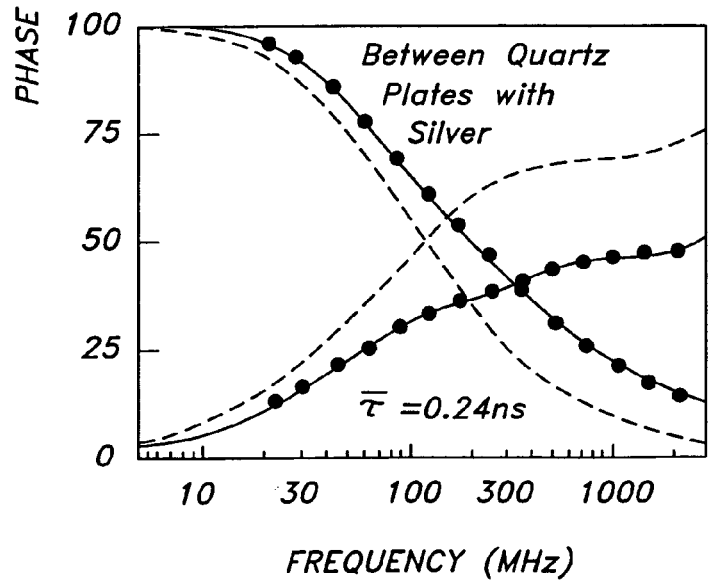

An increase in energy transfer from DAPI to PI is expected to result in a decrease in the DAPI decay time. Frequency-domain intensity decay of DAPI are shown in FIG. 23. The dashed lines in each panel show the DAPI decays in the absence of the PI acceptor. In all cases the mean DAPI lifetimes decreased in the presence of PI (Table 2). The mean DAPI decay time ($\bar{\tau}=2.93$ ns without acceptor) was reduced about 20% to $\bar{\tau}=2.39$ ns in the presence of the silver island, while the steady state intensity was essentially unchanged (FIG. 21). This result suggests an increase in the rate of radiative decay due to the silver islands. Control measurements showed the absence of scattered light in all these measurements.

TABLE 2

Multi-exponential analysis of DAPI donor intensity decay in the presence and absence of acceptor and silver islands

| Sample[1] | $\bar{\tau}$ (ns)[2] | $\tau$(ns)[3] | $\alpha_1$ | $\tau_1$(ns) | $\alpha_2$ | $\tau_2$(ns) | $\alpha_3$ | $\tau_3$(ns) | $\chi_R^2$ |
|---|---|---|---|---|---|---|---|---|---|
| DAPI-DNA, C | 2.93 | 2.42 | 0.278 | 0.63 | 0.722 | 3.11 | — | — | 2.1 |
| DAPI-DNA, Q | 2.80 | 1.58 | 0.311 | 0.16 | 0.391 | 1.15 | 0.298 | 3.62 | 2.2 |
| DAPI-DNA, S | 2.39 | 1.10 | 0.447 | 0.09 | 0.414 | 1.29 | 0.139 | 3.70 | 2.1 |
| DAPI-PI-DNA, C | 2.16 | 1.04 | 0.427 | 0.11 | 0.308 | 0.84 | 0.265 | 2.77 | 1.0 |
| DAPI-PI-DNA, Q | 2.26 | 0.80 | 0.467 | 0.08 | 0.367 | 0.66 | 0.166 | 3.15 | 1.7 |
| DAPI-PI-DNA, S | 1.67 | 0.24 | 0.769 | 0.04 | 0.172 | 0.40 | 0.059 | 2.44 | 3.2 |

[1] C - in 0.5 mm cuvette, Q - between quartz plates without silver, S - between quartz plates with silver
[2] $\bar{\tau} = \Sigma f_i \tau_i$
[3] $\langle \tau \rangle = \Sigma \alpha_i \tau_i$ DAPI donor decay was examined when the donor and acceptor-labeled DNA is in a 0.5 mm cuvette, between plain quartz plates, and between silver island films (Table 2). The mean DAPI lifetime was not changed going from the cuvette to the unsilvered quartz plates, r=2.16 and 2.26 ns, respectively. A dramatic decrease in the DAPI decay time to r=1.67 ns was found for DAPI-DNA between the silver island films (FIG. 23A C). This decrease in lifetime is attributable to the increased in RET seen in the emission spectra (FIG. 22).

The frequency-domain donor decays in terms of the apparent Förster distance were analyzed. This was accomplished by analyzing the donor decay. The acceptor concentration was held constant at 0.075 acceptors per base pair and the values of $R_0$ were allowed to vary to obtain the best fit to the data (FIG. 24A-C). The value of $R_0$=37.4 Å is close to that calculated for the D-A pair, $R_0$=35.7 Å. The apparent value of $R_0$ decreased to 33.5 Å between the quartz plates. Importantly, the apparent value of $R_0$ increased 2-fold to 75.6 Å for the sample between the silver island films. This is an apparent $R_0$ value. Examination of this fit (FIG. 24C) reveals that the frequency-domain intensity decay could not be fit to a single $R_0$ value. This lack of fit suggests the presence of at least two populations of D-A pairs, with the pairs close to the silver islands displaying a larger $R_0$ value.

It is important to recognize that the 2-fold increase in the apparent value of $R_0$ represents a minimum estimate of the effect of the silver islands on RET. The active space near the silver islands extend approximately 200 Å to about 2000 Å into the solution. Assuming a sample thickness of 1 µm only about 1/25 of the sample is within the active value. This suggests that the actual effect on RET is greater than a 2-fold increase in $R_0$.

Example 7

Figure 25:
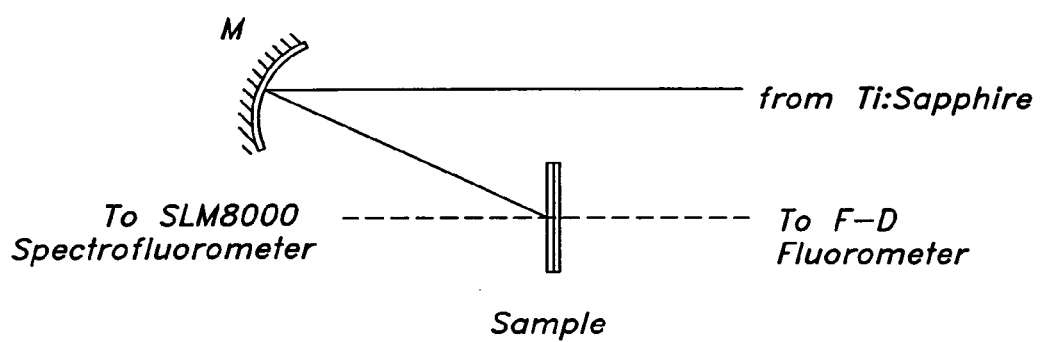
FIG. 25 is an exemplary geometry for detecting fluorophores between silver island films.

Localized Enhancement of Fluorescence Near Metallic Particles With Multi-Photon Excitation RhB, Eosin sodium salt, rose bengal and coumarin 152 were obtained from commercial suppliers. The experimental sample geometry is shown in FIG. 25. Two-photon excitation of RhB, eosin and rose bengal was accomplished with the 852 nm output of a Tsunami mode-locked Ti:Sapphire laser, 80 MHz repetition rate, 90 fs pulse, about 0.5 W average power. For C152 and ANS the multi-photon excitation wavelength was near 800 nm. The excitation was focused on the sample with a 15 cm radius concave mirror. The solution was placed between two high quality quartz plates, λ/4 flatness. The plates were half uncoated and half coated with silver islands as described above. From absorption measurements the thickness of the samples between the plates was about 1 µm. This sandwich sample was mounted on a x-y positioner. The focused spot of the laser was about 4 mm in length and 30 µm in diameter. The x-y positioner was used to move the sample so the laser illuminated regions with or without silver islands. This position change was accomplished without any change in the experimental geometry. Scattered excitation was eliminated with a combination of a heat filter and BG-38 glass filter for the emission spectra and a BG-38 and a 580 nm interference filter for time-resolved measurements.

Intensity decays were measured in the frequency-domain using instrumentation described previously (Lakowicz et al. (1985) *Biophys. Chem.* 21, 61-78; Laczko et al. (1990) *Rev. Sci. Instrum.* 61, 2331-2337). For the frequency-domain measurements the emission was observed through a 580 interference filter. For all steady state and frequency-domain measurements the excitation was vertically polarized and the emission observed through a horizontally oriented polarizer to minimize scattered light. The FD intensity decay were analyzed in terms of the multi-exponential model using equation (1) above where $\tau_i$ are the lifetimes with amplitudes $\alpha_i$ and $\Sigma\alpha_i$=1.0. Fitting to the multi-exponential model was performed as described previously (Lakowicz et al. (1994) *Biophys. J* 46, 463-477). The contribution of each component to the steady state intensity is given by equation (2) above. The mean decay time is given by equation (5) above.

Figure 26A:
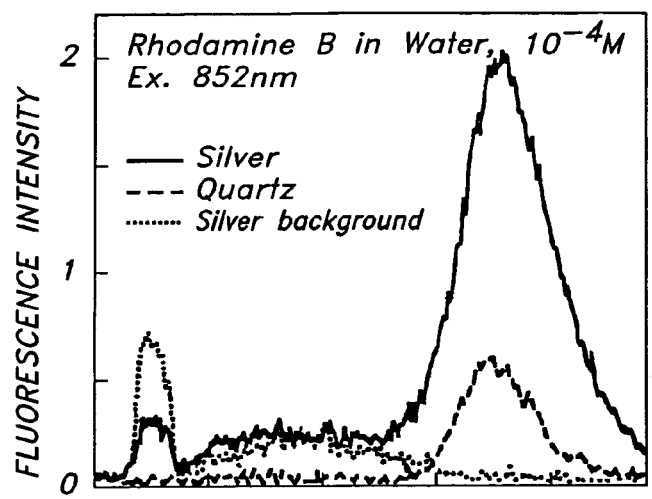
FIGS. 26A and 26B are emission spectra of rhodamine B between silver island films and uncoated quartz plates using one-photon excitation and two photon excitation.
Figure 26B:
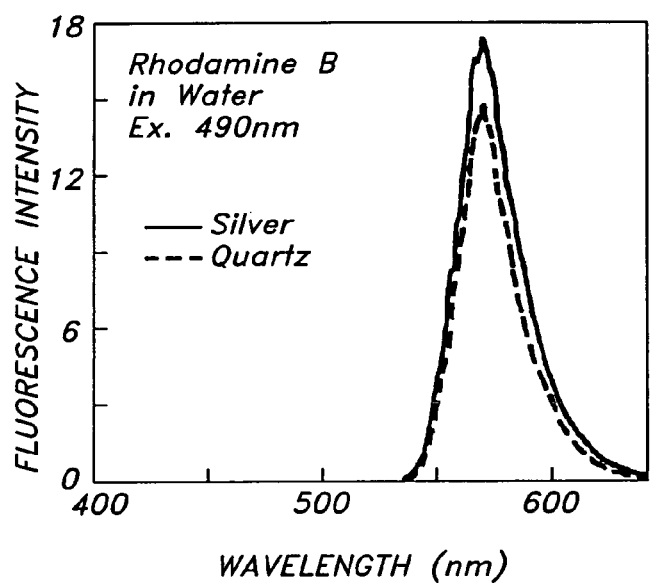

The emission spectra of RhB between silver island films with two-photon excitation at 852 nm was examined (FIG. 26A). The emission intensity for RhB between the metal particles (indicated as ———— in FIG. 26A) was increased about 4-fold relative to RhB between uncoated quartz plates (indicated as - - - in FIG. 26A). When the sample was first exposed to the focused 852 nm light, white light from the illuminated region was visibly detected. This "spark" decayed in less than one second, but some white light background remained. This white light was also seen from the silver islands alone without RhB (indicated as . . . in FIG. 26A). Such a white continuum emission for illuminated metal probes in near-field microscopy has been reported previously (Sanchez et al. (1999) *Phys. Rev. Letts.* 82, 4014-4017). Importantly, the RhB signal remained stable following the initial white light transient. RhB was also examined with one-photon excitation of 490 nm (FIG. 26, bottom). In this case there was almost no effect of the silver islands as compared to the uncoated quartz plates.

Figure 27:
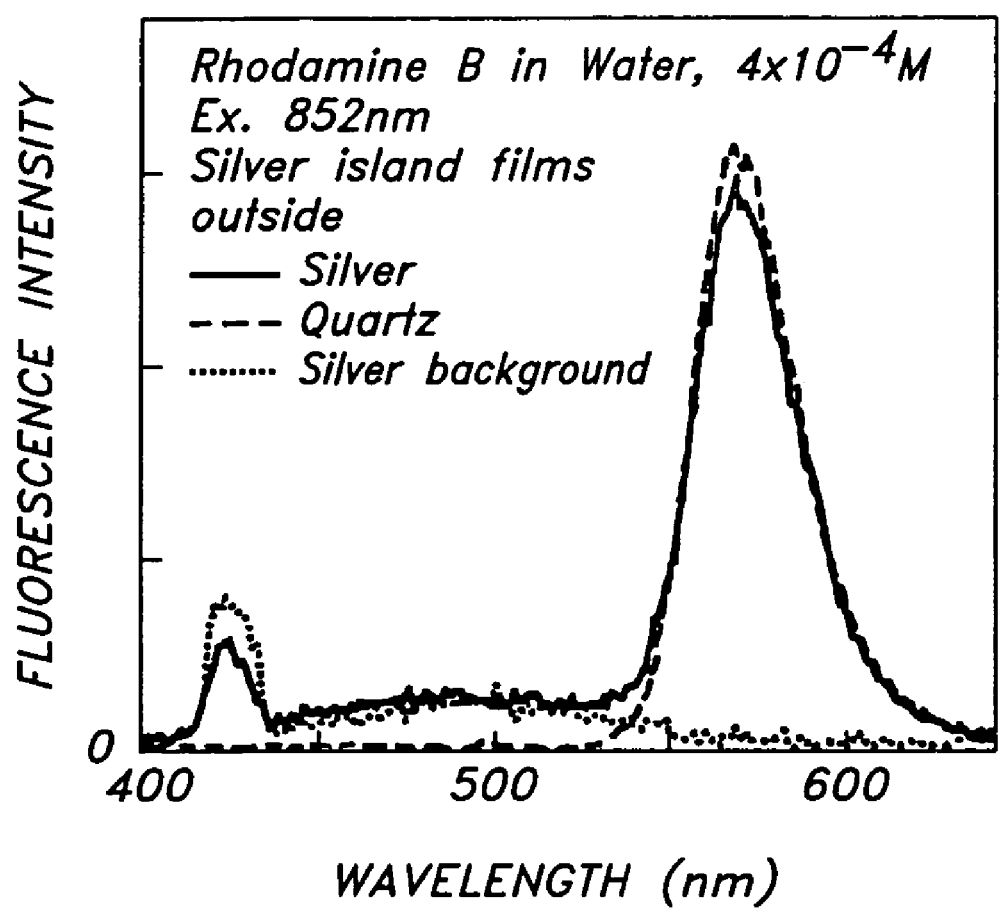
FIG. 27 emission spectra of rhodamine B with two photon excitation between uncoated quartz plates and between quartz plates with silver islands on the outer surface of the quartz plates.

As a control experiment, RhB with two-photon excitation in the presence of silver islands was examined, but with the plates rotated so that the islands were on the outer surface not in contact with RhB (FIG. 27). In this case no difference between the silvered and unsilvered plates were found. The white continuum emission was still observed from the silver islands. This result demonstrated that the enhanced emission of RhB seen by FIG. 26 is due to two-photon excitation of RhB, and not due to second harmonic generation by the metal particles which in turn excites RhB.

The results in FIG. 26 can be understood by considering the nature of our layered sample (see FIG. 1). The fluorophore is uniformly distributed in the 1μ thick sample. The region affected by the metal islands is expected to extend about 250 Å in the solution. Recalling that there were two silver island surfaces, we estimated that only about 5% of the solution is within the active area. In fact, even this percentage is probably too high because the fluorophores within 50 Å of the metal surface are typically quenched. Assuming 5% of the sample is affected by the metal, the 4-fold enhancement for RhB (FIG. 26, top) suggests an 80-fold enhancement of two-photon excitation due to the metal particles. The small fraction of fluorophores near the metal particles explains the absence of a significant effect with one-photon (FIG. 26, bottom) because the majority of the emission occurs from RhB molecules distant from the silver islands.

Figures 28A, 28B:
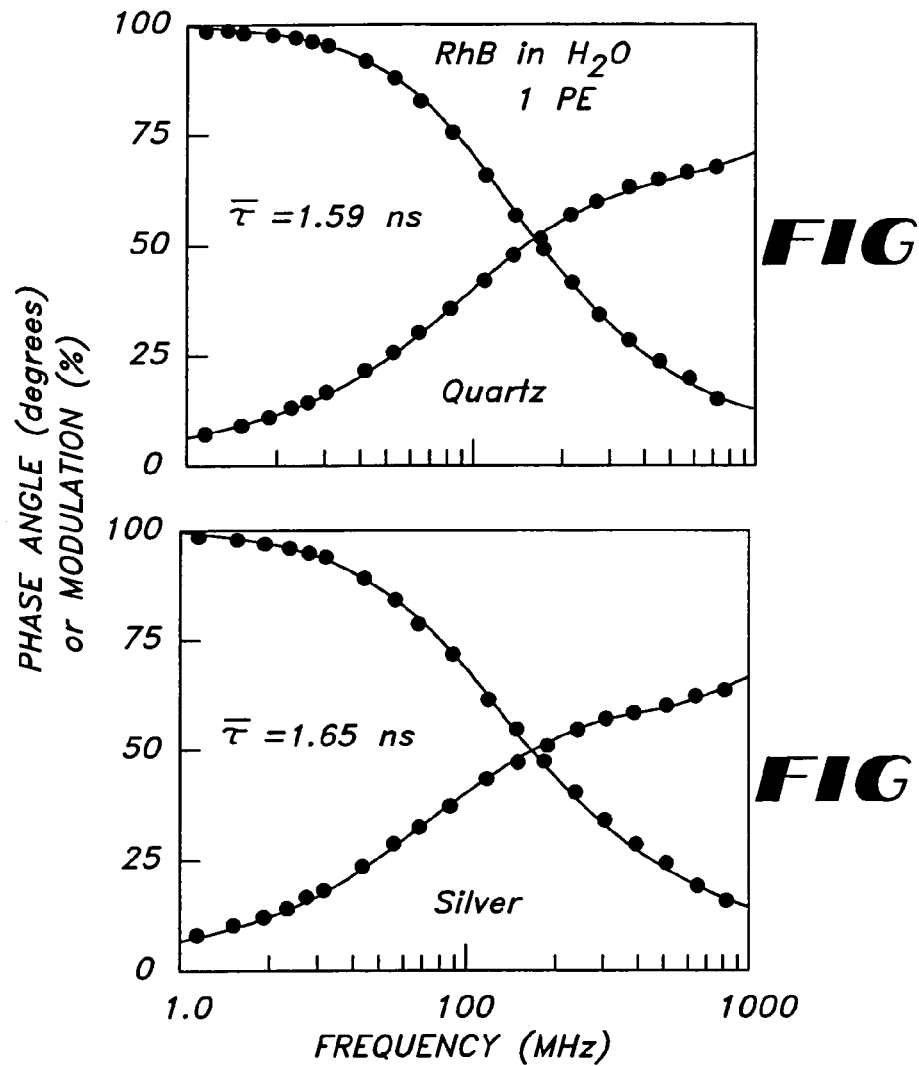
FIGS. 28A and 28B are frequency-domain intensity decays of rhodamine B with one photon excitation between uncoated quartz plates (28A) and between silver island films (28B).

The frequency-domain intensity decays of RhB between coated and uncoated quartz plates with one and two-photon excitation were examined. The excitation wavelength for FIG. 29A was 852 nm, and the observation wavelength was 580 nm. For one-photon excitation the mean lifetime was essentially unchanged between the coated or uncoated plates (FIGS. 28A-B). This result is consisted with FIG. 26B, which showed that most of the one-photon individual emission of RhB occurred from the bulk sample. Contrasting results were found for the intensity decay of RhB with two-photon excitation (FIGS. 29A-B). In this case the mean lifetime is dramatically shortened by the silver island films. The reduced RhB lifetime with 852 nm excitation is the result of localized two-photon excitation of RhB molecules near the metal particles. The reduced RhB lifetime also demonstrated that the excitation is not due to second harmonic generation by the metal islands. The lifetime of RhB resulting from excitation by the harmonic would be the same as that found in the bulk solution.

Figure 30A:
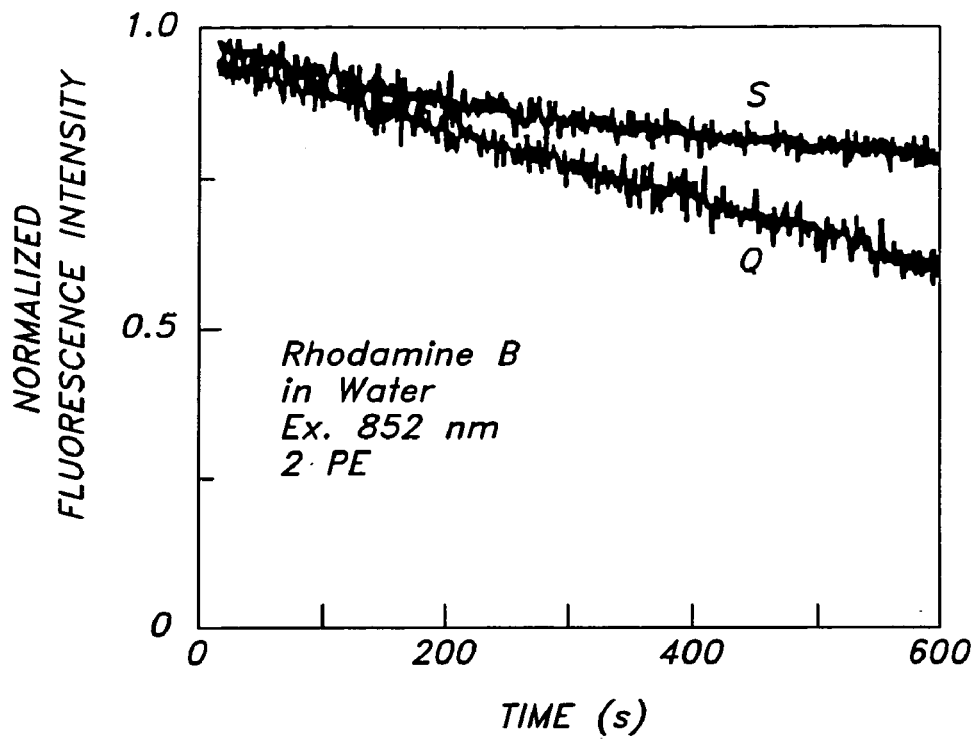
FIGS. 30A and 30B are graphs depicting the photostability of rhodamine B between uncoated quartz plates (Q) and between silver island films (S).
Figure 30B:
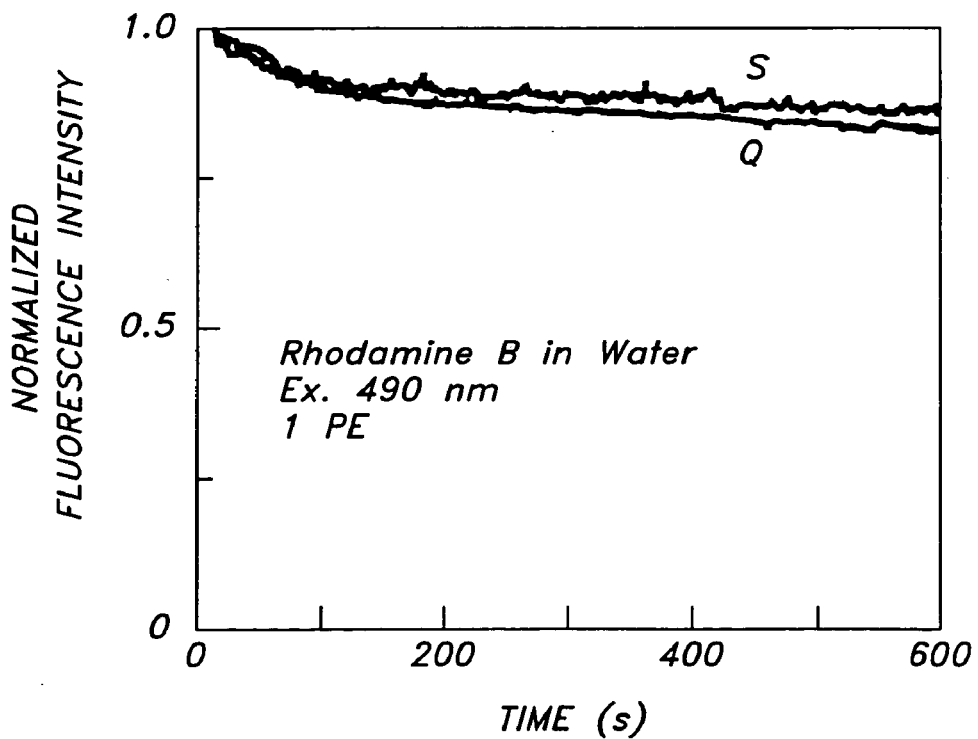

In many applications of fluorescence, photostability of the fluorophore is a primary consideration. This is particularly true in single molecule detection where it has been estimated that approximately 1,000 photons can be observed from a highly stable fluorophore like rhodamine prior to photodestruction (Ambrose et al. (1999) Chem. Rev. 99, 2929-2956). Since photochemistry occurs in the excited state, a reduction in the fluorescence lifetime is expected to result in increased photostability. The photostability of Rhodamine B between coated and uncoated quartz slides with one- and two-photon excitation was examined (FIGS. 30A-B). For one-photon excitation, the photostability was unaffected by the presence or absence of silver islands (FIG. 30B). For two-photon excitation, photostability in the presence of silver islands was enhanced (FIG. 30A). These results are consistent with the shorter lifetime observed for Rhodamine B between silver islands and with the assertion that two-photon excitation is occurring preferentially near the silver island films.

Figure 31A:
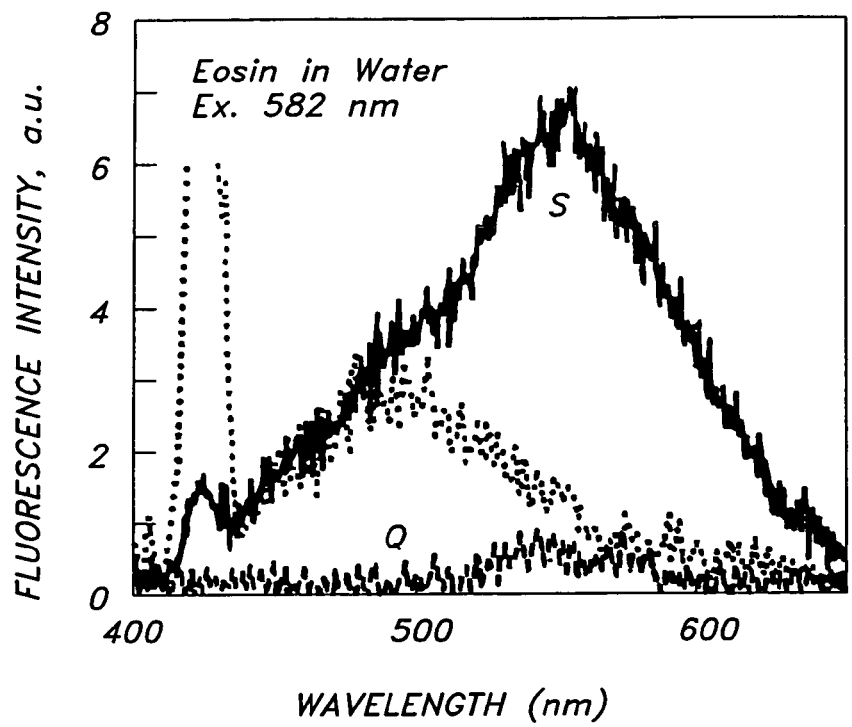
FIGS. 31A and 31B are emission spectra of eosin (31A) and rose bengal (31B) between uncoated quartz plates (Q) and between silver island films (S) using two photon excitation.
Figure 31B:
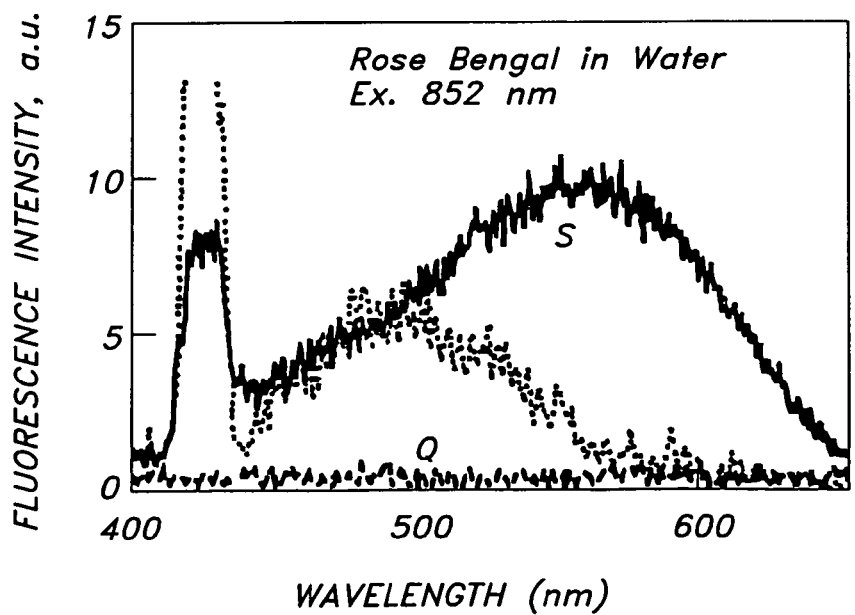

In the proceeding experiments, Rhodamine B was used which displays a quantum yield of 0.48 (Q=0.48) in bulk solution. As a result, much of the emission occurred from the bulk solution in regions unaffected by the silver islands. Multi-photon excitations occurring near the silver islands are increasing the quantum yield of the nearby fluorophores. FIG. 31A shows emission spectra for eosin (Q=0.24), and FIG. 31B shows the emission spectra for rose bengal (Q=0.02) between quartz plates and between silver island films. Excitation wavelength was 852 nm. In these spectra, the white light continuum resulting from the silver island films is more evident because of the lower overall signal. Importantly, with two-photon excitation, there is essentially no emission from eosin or rose bengal under conditions where there is substantial emission from the fluorophores between the silver islands. This result suggested selective and localized two-photon excitation near metal particles.

Figure 32A:
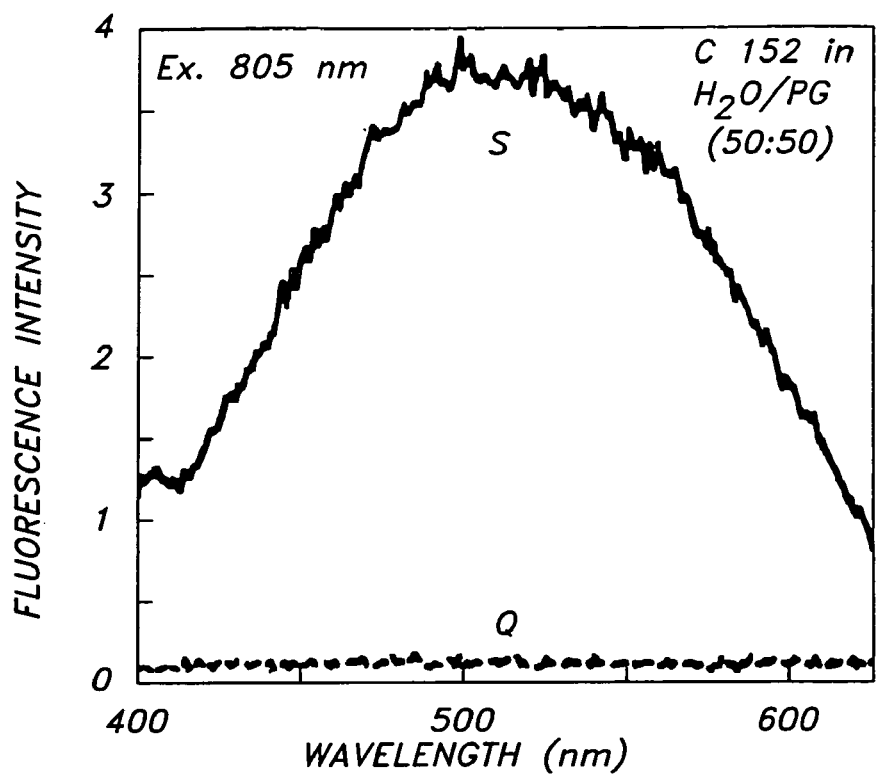
FIGS. 32A and 32B are emission spectra of coumarin (32A) between uncoated quartz plates (Q) and between silver island films (S) and ANS (32B) in a cuvette (C), between uncoated quartz plates (Q), and between silver island films (S).
Figure 32B:
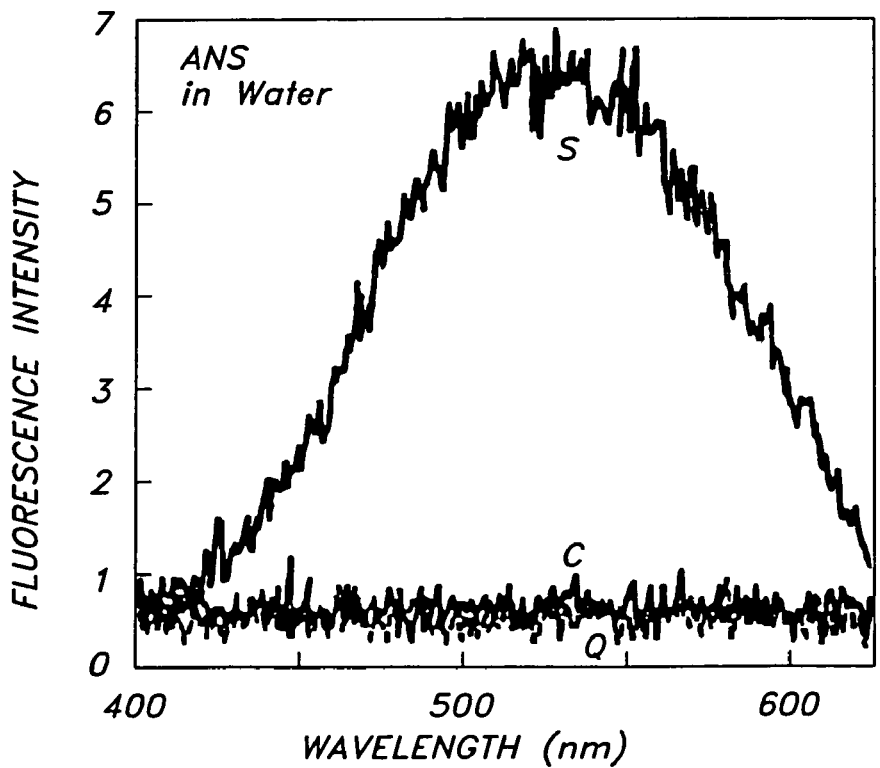

The concept of selective excitation was pursued further using biochemically relevant fluorophores such as coumarin 152 and ANS (FIG. 32A-B). In this case a remarkable enhancement of the two-photon induced emission for these fluorophores between silver island films was observed. In the case of ANS with a very low quantum yield in water (Q<0.01) there was essentially no signal seen for ANS between the uncoated slides, and even the signal observed from a bulk solution in a cuvette was insignificant compared to the two-photon induced emission in the presence of silver particles. The results shown in FIGS. 31A-B and 32A-B suggest that multi-photon excitation near silver particles is a general phenomenon which can result in highly localized excitation in regions near the metal particles.

Figure 33:
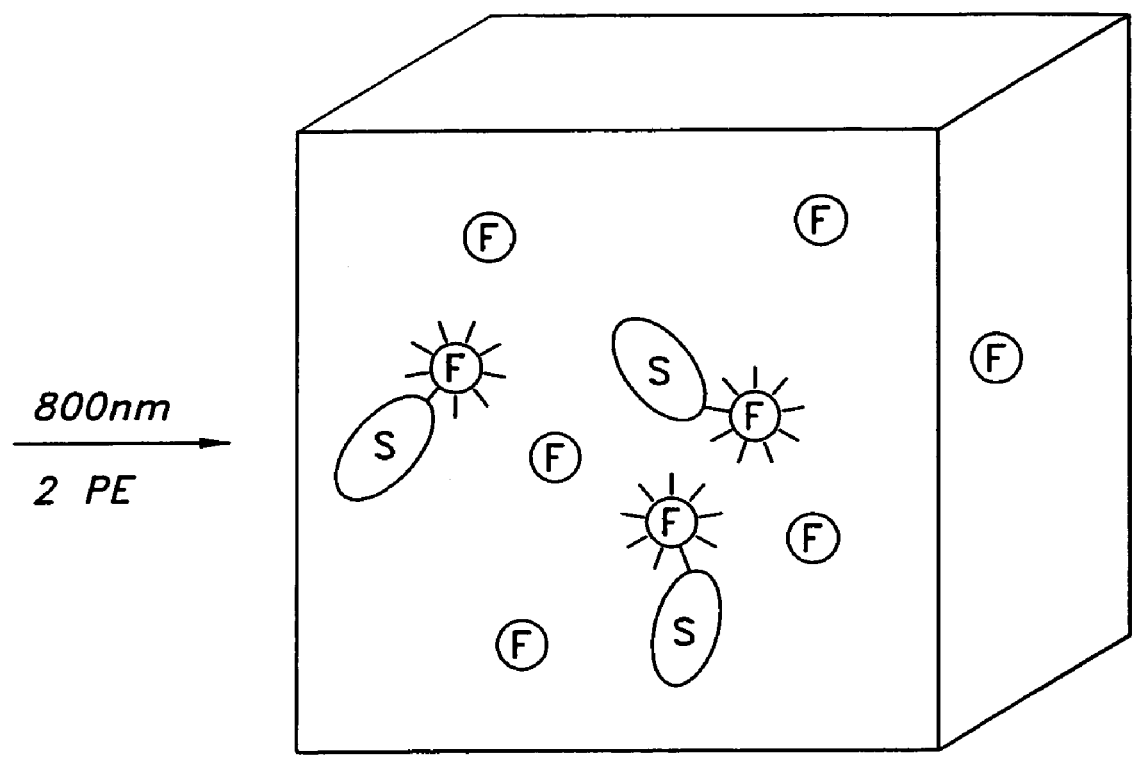
FIG. 33 is a depiction of selective multi-photon excitation of fluorophores on metal colloids in the presence of free fluorophore.

FIG. 33 is an illustration of how fluorophores on metal colloids can be selectively detected by multi-photon excitation in the presence of free fluorophore. Only the fluorophores within about 50 to about 2000 Å, preferably from about 50 Å to about 200 Å, of a metal particle will have increased fluorescence when exposed to an amount of exciting radiation. The free fluorophores will not fluoresce at detectable levels.

Figure 34:
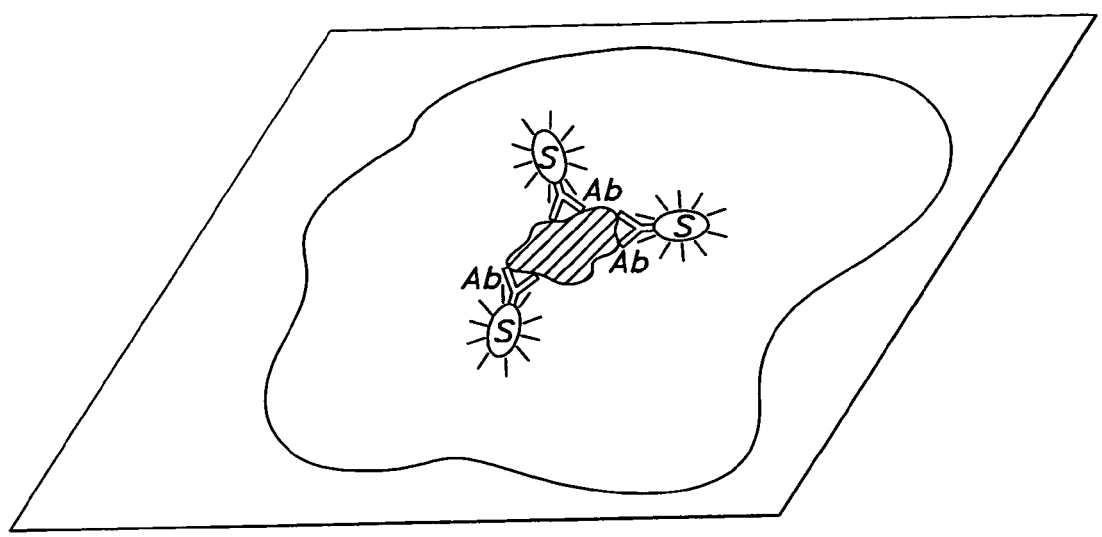
FIG. 34 is a depiction of localized multi-photon excitation of intracellular autofluorescence by metal colloids.

FIG. 34 is an illustration of localized multi-photon excitation of intracellular autofluorescence by metal colloids. In one embodiment, a metal particle, preferably a noble metal, is attached to an antibody that binds to a desired target. When the antibody binds to the desired target, the metal particle is positioned near the target at a distance sufficient to increase the fluorescence of the target, typically about 50 to about 2000 Å, preferably from about 50 Å to about 200 Å, in response to an exciting amount of fluorescence, preferably multi-photonic excitation. The antibody can be from any host animal capable of producing antibodies. Exemplary host animals include mammals, preferably rabbits, goats, horses, and humans. The antibody can also be conjugated with an extrinsic fluorophore.

Example 8

Assays

Figure 35:
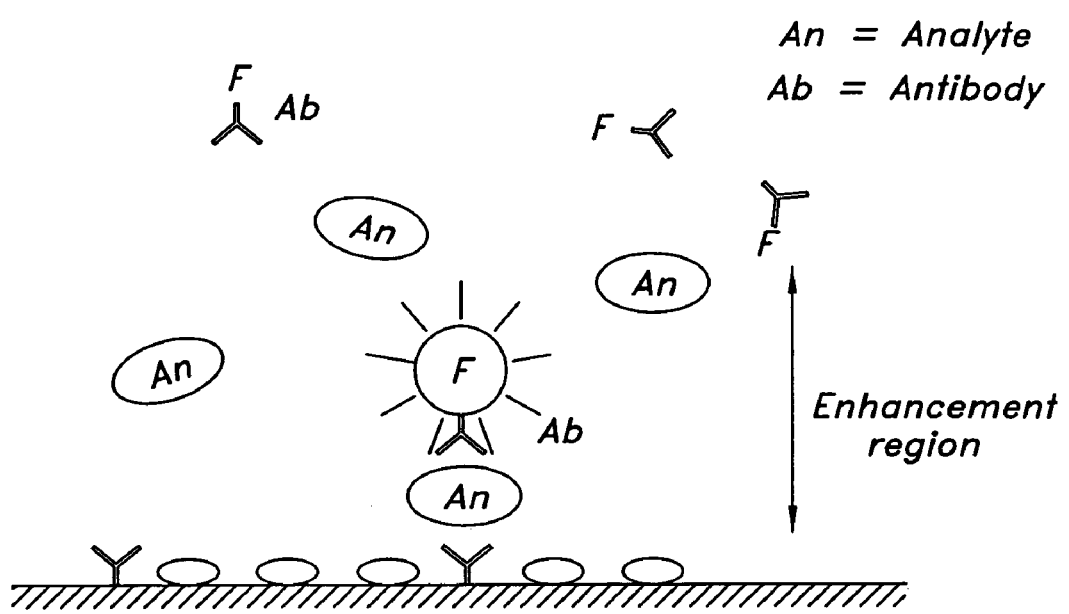
FIG. 35 is an exemplary embodiment of a sandwich immunoassay in conjunction with a silver island coated surface.

FIG. 35 depicts a schematic for an immunoassay assay. A capture antibody is covalently bound to the surface near the metal particles. The presence of the analyte (An) results in surface binding of a second antibody which is labeled with a non-fluorescent chromophore. Exemplary non-fluorescent or weakly fluorescent chromophores fluorophore include, but are not limited to, rose bengal, eosin, malachite green, and organic molecules used as dyes or stains in optical microscopy. Suitable organic molecules used as dyes or stains in optical microscopy are well known in the art and include, but are not limited to, acid fuchsin, alcian blue, alizarin red, congo red, crystal violet, eosin, evans blue, light green SF, luxol fast blue, methyl green, neutral red, nigrosin, oil red o, orange g, picric acid, pyronin y, safranine o, sirius red, sudan black b, and toluidine blue o. Upon binding to the antigen, the previously non-fluorescent species emits in response to an amount of exciting radiation due to the increased radiative rate. The unbound species more distant from the metal site will not interfere with the fluorescent signal because they do not fluoresce. The non-fluorescent species becomes a "molecular beacon" emitting only when close to the metal particles. It will be appreciated that antibodies or antibody fragments from any host capable of producing antibodies can be used. Exemplary hosts include mammals such as primates, goats, horses, rabbits, and rodents. Additionally, recombinant or chimeric antibodies can also be used. This assay can/be used to detect the presence of an analyte in biologic fluids including, but not limited to, saliva, urine, mucus, blood, plasma, and lymphatic fluid. Exemplary analytes include steroids, small molecules, proteins, peptides, bacteria, and fungi.

Figure 36A:
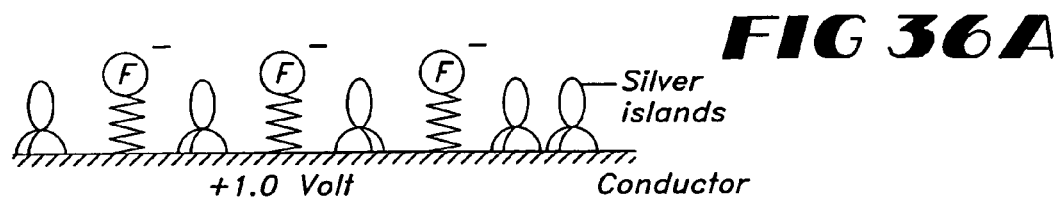
FIGS. 36A-C are an exemplary embodiment of voltage-activated fluorescence assays.
Figure 36B:
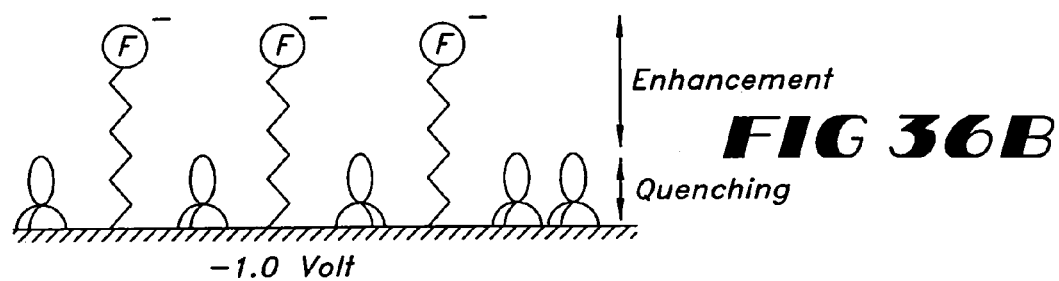
Figure 36C:
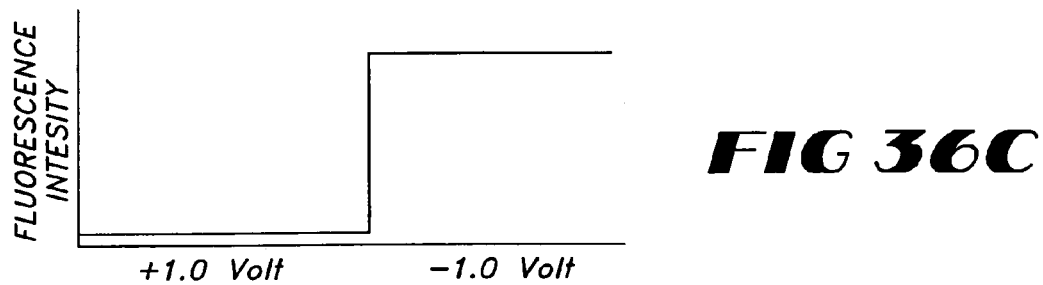

FIG. 36 depicts an assay of the present invention which uses electrical potential to gate the fluorescence on and off. A fluorophore is positioned at the end of a flexible polymer chain which is attached to a surface coated with metal particles In one embodiment, the entire chain and fluorophore are negatively charged. When the voltage or the metal is positive, the fluorophore is in the quenched zone. When the voltage is negative, the fluorophore is displaced into the enhancement zone. Alternatively, the fluorophore is moved in and out of the shorter range quenching zone of the metal. Thus, the emission is gated by the voltage. The electric potential can be generated using known techniques. Suitable sources of electric potential include devices capable of producing electricity including, but not limited to, batteries, fuel cells, and transformers. In another embodiment, a method to access array sensors using electric potential is provided using methods known for linking DNA or proteins in desired patterns on surfaces. For example, biomolecules can be linked to surfaces using adhesives, polymers, lysine, or biotin-avidin.

Another embodiment of the present invention discloses an immunoassay in wherein a first antibody is labeled with a donor molecule and a second antibody is labeled with an acceptor molecule (FIG. 37). The labeled antibodies will bind to their respective antigens to form a complex. When the complex is near a metal particle, the resonance energy transfer from donor to acceptor is enhanced such that the emission from the acceptor is detectable. The complexes can be positioned near a silver island surface using electrical potential or other attractive forces. The metal-induced increased in the transfer rate results in transfer over larger distances, and the antigen is detectable by an increase in the transfer efficiency.

FIG. 38 depicts another embodiment of the present invention, an apparatus for surface plasmon excitation. For the control surface without silver (FIG. 38B) the emission increases at the critical angle for the fluorescence. When excitation is at the plasmon resonance angle the emission is sharply distributed at the plasmon angle for the emission wavelength. A typical metallic surface for this purpose would be a continuous, semi-transparent silver coating. This coating may be further modified by binding of metallic colloids or particles to provide both enhanced and directional emission.

Various modifications may be made to the invention as described without departing from the spirit of the invention or the scope of the appended claims.

What is claimed is:

1. A method for detecting a biomolecule by increasing intrinsic fluorescence of said biomolecule, said method comprising:

positioning a metal particle and said biomolecule at a distance sufficient to increase an intrinsic fluorescent emission from said biomolecule, wherein said metal particle is a silver particle or a gold particle, and wherein said biomolecule is selected from the group consisting of a nucleic acid; NADH; FAD; tryptophan, tyrosine, phenylalanine, proteins containing tryptophan, tyrosine, phenylalanine or any combination thereof; flavins; purines; pyrimidines; formycin; and phycobiliprotein;

exposing said biomolecule to an amount of exciting radiation sufficient to produce said intrinsic fluorescent emission for detection; and detecting the intrinsic fluorescent emission from said biomolecule by a fluorescence detector.

2. A method for manipulating intrinsic fluorescent intensity of a biomolecule, said method comprising:

increasing a rate of radiative decay of the biomolecule by positioning a metal particle and the biomolecule at a distance sufficient to increase said radiative decay, said increase in said rate of radiative decay being associated with an increase in said intrinsic fluorescent intensity by intrinsic fluorescent emission of said biomolecule, wherein said metal particle is a silver particle or a gold particle, and wherein said biomolecule is selected from the group consisting of a nucleic acid; NADH; FAD; tryptophan, tyrosine, phenylalanine, proteins containing tryptophan, tyrosine, phenylalanine or any combination thereof; flavins; purines; pyrimidines; formycin; and phycobiliprotein;

exposing the biomolecule to exciting radiation; and detecting an increased rate of radiative decay from said biomolecule by frequency-domain analysis of a fluorescent spectrum detected by a fluorescence detector.

3. The method of claim 1, wherein said distance between said metal particle and said biomolecule is obtained by any of a chemical linker comprising an atom or a molecule, electromagnetic forces, charge fields, and gravity.

4. The method of claim 1, wherein said biomolecule, when positioned at a distance greater than 2000 Å from said metal particle, has a quantum yield of less than 0.8.

5. The method of claim 1, wherein said distance separating said biomolecule and said metal particle is about 50 Å to about 2000 Å.

6. The method of claim 1, wherein said metal particle is suspended in a colloid.

7. The method of claim 1, wherein said silver particle spherical dimensions of about 40 to 50 nm.

8. The method of claim 2, wherein said distance between said metal particle and said biomolecule is obtained by any of a chemical linker comprising an atom or a molecule, electromagnetic forces, charge fields, and gravity.

9. The method of claim 2, wherein said biomolecule, when positioned at a distance greater than 2000 Å from said metal particle, has a quantum yield of less than 0.8.

10. The method of claim 2, wherein said distance separating said biomolecule and said metal particles is about 50 Å to about 2000 Å.

11. The method of claim 2, wherein said metal particle is suspended in a colloid.

12. The method of claim 2, wherein said silver particle has spherical dimensions of about 40 to 50 nm.

* * * * *

UNITED STATES PATENT AND TRADEMARK OFFICE
CERTIFICATE OF CORRECTION

PATENT NO. : 7,776,528 B2  Page 1 of 1
APPLICATION NO. : 10/990549
DATED : August 17, 2010
INVENTOR(S) : Joseph R. Lakowicz It is certified that error appears in the above-identified patent and that said Letters Patent is hereby corrected as shown below:

Please replace paragraph Col. 1 lines 13-18 STATEMENT REGARDING FEDERALLY SPONSORED RESEARCH as follows:

This invention was made with government support under Grant Number RR08119 awarded by the National Institutes of Health. The government has certain rights in the invention.

Signed and Sealed this

Fifth Day of October, 2010

David J. Kappos
*Director of the United States Patent and Trademark Office*